US007015220B2

(12) United States Patent
Andrews et al.

(10) Patent No.: US 7,015,220 B2
(45) Date of Patent: Mar. 21, 2006

(54) 3-(ARYLAMINO)METHYLENE-1, 3-DIHYDRO-2H-INDOL-2-ONES AS KINASE INHIBITORS

(75) Inventors: Steven W. Andrews, Longmont, CO (US); Julie A. Wurster, Irvine, CA (US); Edward H. Wang, Dove Canyon, CA (US); Thomas Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 51 days.

(21) Appl. No.: 10/783,325

(22) Filed: Feb. 20, 2004

(65) Prior Publication Data

US 2004/0198720 A1 Oct. 7, 2004

Related U.S. Application Data

(62) Division of application No. 10/256,879, filed on Sep. 27, 2002, now Pat. No. 6,765,012.

(60) Provisional application No. 60/325,819, filed on Sep. 27, 2001, provisional application No. 60/325,815, filed on Sep. 27, 2001.

(51) Int. Cl.
A61K 31/404 (2006.01)
A61K 31/5375 (2006.01)
C07D 413/02 (2006.01)
C07D 241/04 (2006.01)
C07D 209/04 (2006.01)

(52) U.S. Cl. .................... 514/235.2; 544/106; 544/111; 544/144; 544/358; 546/184; 546/192; 548/469; 548/484; 548/486; 514/418

(58) Field of Classification Search ................ 548/469, 548/484, 486; 544/106, 111, 144, 358; 514/231.2, 514/235.2, 418
See application file for complete search history.

(56) References Cited

U.S. PATENT DOCUMENTS

| 4,966,849 | A | 10/1990 | Vallee et al. |
| 5,217,999 | A | 6/1993 | Levitzki et al. |
| 5,302,606 | A | 4/1994 | Spada et al. |
| 5,330,992 | A | 7/1994 | Eissenstat et al. |
| 5,792,783 | A | 8/1998 | Tang et al. |
| 5,834,504 | A | 11/1998 | Tang et al. |
| 5,883,113 | A | 3/1999 | Tang et al. |
| 5,883,116 | A | 3/1999 | Tang et al. |
| 5,886,020 | A | 3/1999 | Tang et al. |
| 6,316,635 | B1 | 11/2001 | Tang et al. |
| 6,762,180 | B1 * | 7/2004 | Roth et al. ................ 514/228.2 |
| 6,765,012 | B1 * | 7/2004 | Andrews et al. ............ 514/323 |
| 6,855,710 | B1 * | 2/2005 | Walter et al. ............. 514/228.2 |

FOREIGN PATENT DOCUMENTS

| DE | 19824922 | 12/1999 |
| WO | WO 91/15495 | 10/1991 |
| WO | WO 92/20642 | 11/1992 |
| WO | WO 92/21660 | 12/1992 |
| WO | WO 94/03427 | 2/1994 |
| WO | WO 94/10202 | 5/1994 |
| WO | WO 94/14808 | 7/1994 |
| WO | WO 00/12084 | 3/2000 |
| WO | WO 01/16130 | 3/2001 |

OTHER PUBLICATIONS

Walter et al (2000): STN International CAPLUS database, Columbus (Ohio), Accession No., 2000: 227630.*
Glennon et al (2000): STN International CAPLUS database, Columbus (Ohio), Accession No., 2000: 688216.*
Plowman et al, "Receptor Tyrosine Kinases as Targets for Drug Intervention", 1994, DN&P 7(6): 334-339.
Bolen, "Nonreceptor tyrosine protein kinases", 1993, Oncogen 8: 2025-2031.
Kendall et al, "Inhibition of vascular endothelial cell growth factor activity by an endogenously encoded soluble receptor", 1994, Proc. Natl'l Acad. Sci. 90:10705-10709.
Kim et al, "Inhibition of vascular endothelial growth factor-induced angiogenesis suppresses tumor growth in vivo", Nature 362, 841-844.
Jellinek et al, "Inhibition of Receptor Binding by High-Affinity RNA Ligands to Vascular Endothelial Growth Factor", Biochemistry 33: 10450-10456.
Takano et al, "Inhibition of Angiogenesis by a Novel Diaminoanthraquinone that Inhibits Protein Kinase C.", 1993, Mol. Bio. Cell 4: 2072, p. 358A.
Kinsella et al, "Protein Kinase C Regulates Endothelial Cell Tube Formation on Basement Membrane Matrix, Matrigel", 1992, Experimental Cell Research, 199: 56-62.
Wright et al, "Inibition of Angiogenesis In Vitro and In Ovo With an Inhibitor of Cellular Protein Kinases, MDL 27032", 1992, Journal of Cellular Phys. 152: 448-457.
Mariani et al, "Inhibition of angiogenesis by FCE 26806, a potent tyrosine kinase inhibitor", 1994, Proc. Am. Assoc. Cancer Res. 35:2268; p. 381.
Castro et al, "Quantitative Image Analysis of Laser-induced Choroidal Neovascularization in Rat", Exp. Eye Res. 2000; 71:523-55.
Wolfbeis, "Eine Effiziente Synthese Von Amino . . . ", vol. 112, Mar. 1, 1981, pp. 369-383.
Coda et al, "Copper (II) in Organic Synthesis . . . " vol. 117, No. 5, 1987, pp. 301-305.
Seshadn et al, "Studies on the Application of the Vilsmeier-Haack Reaction to Lactams . . . ", Indian Journal of Chemistry, vol. 7, Jul. 1969, pp. 667-671.

* cited by examiner

Primary Examiner—Golam M. M. Shameem
(74) Attorney, Agent, or Firm—Robert J. Baran; Martin A. Voet; Stephen Donovan

(57) ABSTRACT

The present invention relates to organic molecules capable of modulating tyrosine kinase signal transduction in order to regulate, modulate and/or inhibit abnormal cell proliferation.

45 Claims, No Drawings

3-(ARYLAMINO)METHYLENE-1, 3-DIHYDRO-2H-INDOL-2-ONES AS KINASE INHIBITORS

This application is a divisional application of Ser. No. 10/256,879, filed Sep. 27, 2002, now U.S. Pat. No. 6,765,012 which claims priority under 35 U.S.C. §119(e)(1) to provisional application Nos. 60/325,819 and 60/325,815, filed Sep. 27, 2001.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phophorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334–339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025–2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (PCT Application No. WO 94/10202; Kendall & Thomas, 1994, Proc. Nat'l Acad. Sci 90: 10705–09; Kim, et al, 1993, Nature 362: 841–844), RNA ligands (Jellinek, et al, Biochemistry 33: 10450–56); Takano, et al, 1993, Mol. Bio. Cell 4:358A; Kinsella, et al, 1992, Exp. Cell Res. 199: 56–62; Wright, et al, 1992, J. Cellular Phys. 152: 448–57) and tyrosine kinase inhibitors (PCT Application Nos. WO 94/03427; WO 92/21660; WO 91/15495; WO 94/14808; U.S. Pat. No. 5,330,992; Mariani, et al, 1994, Proc. Am. Assoc. Cancer Res. 35:2268).

More recently, attempts have been made to identify small molecules which act as tyrosine kinase inhibitors. For example, bis monocyclic, bicyclic or heterocyclic aryl compounds (PCT Application No. WO 92/20642), vinyleneazaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Finally, certain small compounds are disclosed in U.S. Pat. Nos. 5,792,783; 5,834,504; 5,883,113; 5,883,116 and 5,886,020 as useful for the treatment of diseases related to unregulated TKS transduction. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, autoimmune diseases and transplant rejection.

In one illustrative embodiment, the compounds of the present invention have the formula:

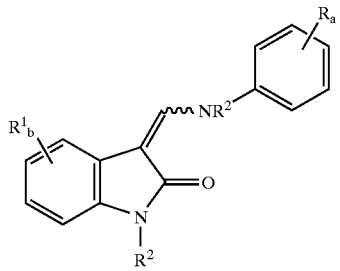

wherein $R^1$ is selected from the group consisting of halogen, $NO_2$, CN, $C_1$ to $C_4$ alkyl and aryl, e.g. phenyl; $R^2$ is selected from the group consisting of hydrogen, $C_1$ to $C_8$ alkyl, $COCH_3$, $CH_2CH_2OH$, $CH_2CH_2CH_2OH$ and phenyl; R is selected from the group consisting of D, halogen, $C_1$ to $C_8$ alkyl, $CF_3$, $OCF_3$, $OCF_2H$, $CH_2CN$, CN, $SR^2$, $(CR^7R^8)_cC(O)OR^2$, $C(O)N(R^2)_2$, $(CR^7R^8)_cOR^2$, $HNC(O)R^2$, HN—C(O)OR$^2$, $(CR^7R^8)_cN(R^2)_2$, $SO_2$ $(CR^7R^8)_cN(R^2)_2$, $OP(O)(OR^2)_2$, $OC(O)OR^2$, $OCH_2O$, HN—CH=CH, —N(COR$^2$)$CH_2CH_2$, HC=N—NH, N=CH—S, $O(CR^7R^8)_d$—$R^6$ and $(CR^7R^8)_c$—$R^6$, —$NR_2(CR^7R^8)_dR^6$ wherein $R^6$ is selected from the group consisting of halogen, 3-fluoropyrrolidinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N-BOC-pyrrolidinyl, 4-amino-1,2,2,6,6-pentamethylpiperidinyl, 4-aminomethyltetrahydropyran, ethanolamine and alkyl-substituted derivatives thereof and wherein when c is 1 said $CH_2$ may be

and $CH_2CH_2CH_2$; provided said alkyl or phenyl radicals may be substituted with one or two halo, hydroxy or lower alkyl amino radicals wherein $R^7$ and $R^8$ may be selected from the group consisting of H, F and $C_1$–$C_4$ alkyl or $CR^7R^8$ may represent selected from the group consisting of H, F and $C_1$–$C_4$ alkyl or $CR^7R^8$ may represent b is 0 or an integer of from 1 to 3;
a is 0 or an integer of from 1 to 5, preferably 1 to 3;
c is 0 or an integer of from 1 to 4,
d is an integer of from 2 to 5;
the wavy line represents a E or Z bond and pharmaceutically acceptable salts thereof.

DETAILED DESCRIPTION OF THE INVENTION

In one embodiment of the present invention $R^1$ is selected from the group consisting of H, i.e. b is 0; $CH_3$, F, Cl and phenyl.

Preferably, R is selected from the group consisting of $CH_3$, $CH_2CH_3$, $OCH_3$, OH, t-butyl, F, CN, $C(O)NH_2$, HN C(O)CH₃, CH₂C(O)OH, SO₂NH₂, C(O)OH, OCF₂H, isopropyl, C₂H₅OH, C(O)OCH₃, CH₂OH, NH—CH═CH, HC═N—N—H, N═CH—S, O(CR⁷R⁸)_dR⁶, (CR⁷R⁸)_cR⁶ and —NR²(CR⁷R⁸)_dR⁶, wherein R⁶ is selected from the group consisting of 3-fluoropyrrolidinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl) pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N-BOC-pyrrolidinyl, 4-amino-1,2,2,6,6-pentamethylpiperidinyl, 4aminomethyltetrahydropyranyl, ethanolamine and alkyl-substituted derivatives thereof, e.g. R⁶ is morpholinyl or CH₂N(CH₃)₂.

More preferably, R is selected from the group consisting of m-ethyl, p-methoxy, p-hydroxy, m-hydroxy, p-cyano, m-C(O)NH₂, p-HNC(O)CH₃, p-CH₂C(O)OH, p-SO₂NH₂, p-CH₂OH, m-methoxy, p-CH₂CH₂OH, HNCH═CH, HC═N—NH, p-morpholinyl, N═CH—S, p-OCHF₂, p-COOH, p-CH₃, p-OCH₃, m-F, m-CH₂N(C₂H₅)₂, (CR⁷R⁸)_cR⁶, O(CR⁷R⁸)_dR⁶ and NR²(CR⁷R⁸)_dR⁶.

It is noted that R may represent a condensed ring that is attached to the above phenyl ring at two positions. For example, as shown in Example 23, below, CH₂CH₂CH₂ may be attached at the 3 and 4 (or m and p) positions of the phenyl ring.

Still more preferably, R is selected from the group consisting of fluoro, methyl, (CR⁷R⁸)_cR⁶, O(CR⁷R⁸)_dR⁶ and NR²(CR⁷R⁸)_dR⁶ wherein R⁶ is selected from dimethylamino, diethylamino, 3-fluoropyrrolidinyl, 3-fluoropiperidinyl, 3-pyridinyl, 4-pyridinyl, pyrrolidinyl, morpholinyl, piperazinyl, heptamethyleneiminyl, tetrahydrofurfurylaminyl, 4-aminotetrahydropyranyl, N,N-diisopropylethylenediaminyl and 4-aminomethyltetrahydropyran.

In particular, the compounds of the present invention are selected from the compounds of Table 1, below.

TABLE 1

| Example # | R¹ | 2 | 3 | 4 | 5 | 6 |
|---|---|---|---|---|---|---|
| | | | | R Substitution | | |

Unsubstituted 4-Methyl & 5-Chloro 3-[(Substituted Phenylamino)-methylene]-1,3-dihydro-indol-2-ones.

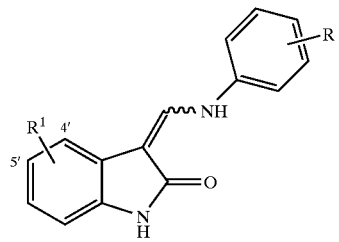

| Example # | R¹ | 2 | 3 | 4 | 5 | 6 |
|---|---|---|---|---|---|---|
| 1 | H | H | H | H | H | H |
| 2 | H | H | Br | H | H | H |
| 3 | H | H | H | Br | H | H |
| 4 | H | Br | H | H | H | H |
| 5 | H | H | H | Et | H | H |
| 6 | H | H | Et | H | H | H |
| 7 | H | H | H | OMe | H | H |
| 8 | H | H | H | CO₂Et | H | H |
| 9 | H | Et | H | H | H | H |
| 10 | H | H | F | Me | H | H |
| 11 | H | Me | F | H | H | H |
| 12 | H | H | H | OH | H | H |
| 13 | H | H | Cl | OH | H | H |
| 14 | H | Me | H | F | H | H |
| 15 | H | H | OH | H | H | H |
| 16 | H | H | OMe | H | OMe | H |
| 17 | H | H | H | tBu | H | H |
| 18 | H | H | H | Me | H | H |
| 19 | H | H | Me | H | Me | H |
| 20 | H | H | Me | Me | H | H |
| 21 | H | H | F | OMe | H | H |
| 22 | H | H | CF₃ | H | H | H |
| 23 | H | H | —CH₂CH₂CH₂— | | H | H |
| 24 | H | F | H | Cl | H | H |
| 25 | H | H | H | CF₃ | H | H |

TABLE 1-continued

| Example # | R¹ | 2 | 3 | 4 | 5 | 6 |
|---|---|---|---|---|---|---|
| 26 | H | F | H | Me | OCO$_2$Et | H |
| 27 | H | F | H | Me | OCO$_2$CH$_2$C(CH$_3$)$_3$ | H |
| 28 | H | F | H | Cl | OH | H |
| 29 | H | H | H | CN | H | H |
| 30 | H | H | H | CH$_2$CN | H | H |
| 31 | H | H | —CH=CH—NH— | | H | H |
| 32 | H | H | —NH—N=CH— | | H | H |
| 33 | H | H | H | CONH$_2$ | H | H |
| 34 | H | H | H | NHCOCH$_3$ | H | H |
| 35 | H | H | CH$_2$CO$_2$H | H | H | H |
| 36 | H | H | H | Cl | H | H |

Unsubstituted, 4-methyl & 5-Chloro 3-[(Substituted Phenylamino)-methylene]-1,3-dihydro-indol-2-ones.

| Example # | R¹ | 2 | 3 | 4 | 5 | 6 |
|---|---|---|---|---|---|---|
| 37 | H | H | CO$_2$H | Cl | H | H |
| 38 | H | H | H | SO$_2$NH$_2$ | H | H |
| 39 | H | H | H | SO$_2$NHCOCH$_3$ | H | H |
| 40 | H | H | H | N-morpholino | H | H |
| 41 | H | H | H | OPh | H | H |
| 42 | H | H | OMe | OMe | H | H |
| 43 | H | H | —S—CH=N— | | H | H |
| 44 | H | H | OH | CO$_2$H | H | H |
| 45 | H | H | CF$_3$ | Cl | H | H |
| 46 | H | H | CF$_3$ | H | CF$_3$ | H |
| 47 | H | H | CF$_3$ | F | H | H |
| 48 | H | H | OH | Me | H | H |
| 49 | H | H | OH | OMe | H | H |
| 50 | H | H | H | OCHF$_2$ | H | H |
| 51 | H | H | H | OCF$_3$ | H | H |
| 52 | H | H | H | iPr | H | H |
| 53 | H | F | H | Me | H | H |
| 54 | H | H | Me | Cl | H | H |
| 55 | H | H | CF$_3$ | OMe | H | H |
| 56 | H | H | CF$_3$ | Me | H | H |
| 57 | 5'-Cl | H | OMe | H | H | H |
| 58 | 4'-Me | H | H | H | H | H |
| 59 | 4'-Me | H | H | OMe | H | H |
| 60 | 4'-Me | H | OH | H | H | H |
| 61 | 4'-Me | H | OMe | H | OMe | H |
| 62 | 4'-Me | H | H | Me | H | H |
| 63 | 4'-Me | H | Me | H | Me | H |
| 64 | 5'-Cl | H | H | OCHF$_2$ | H | H |
| 65 | 5'-Cl | H | OH | OMe | H | H |
| 66 | 5'-Cl | H | H | OCF$_3$ | H | H |
| 67 | 5'-Cl | H | Me | OH | H | H |
| 68 | 5'-Cl | H | —OCH$_2$O— | | H | H |
| 69 | 5'-Cl | H | Me | Me | H | H |
| 70 | 5'-Cl | H | H | iPr | H | H |
| 71 | 5'-Cl | H | OH | Me | H | H |
| 72 | 5'-Cl | H | H | (CH$_2$)$_2$OH | H | H |
| 73 | 5'-Cl | H | H | OMe | H | H |
| 74 | 5'-Cl | H | H | H | H | H |
| 75 | 5'-Cl | H | OMe | H | OMe | H |
| 76 | 5'-Cl | H | OH | H | H | H |
| 77 | 5'-Cl | H | H | OH | H | H |
| 78 | 5'-Cl | H | Me | H | Me | H |
| 79 | 5'-Cl | H | H | Me | H | H |
| 80 | H | H | —OCH$_2$O— | | H | H |
| 81 | H | H | CO$_2$H | OH | H | H |

TABLE 1-continued

| Example # | R¹ | R Substitution | | | | |
|---|---|---|---|---|---|---|
| | | 2 | 3 | 4 | 5 | 6 |
| 82 | H | H | H | OEt | H | H |
| 83 | H | H | —N(COMe)—CH₂—CH₂— | | H | H |
| 84 | H | H | H | OPO(OH)₂ | H | H |
| 85 | H | H | CO₂H | CO₂H | H | H |
| 86 | H | H | H | CO₂H | H | H |
| 87 | H | H | H | (CH₂)₂OH | H | H |
| 88 | H | H | H | CH₂OH | H | H |
| 89 | H | H | OMe | CO₂CH₃ | H | H |
| 90 | 4'-Me | H | —NH—N=CH— | | H | H |
| 91 | 4'-Me | H | F | OMe | H | H |
| 92 | 4'-Me | H | —S—CH=N— | | H | H |
| 93 | 4'-Me | H | OMe | CO₂CH₃ | H | H |
| 94 | H | H | OMe | H | H | H |
| 95 | 4'-Me | H | Me | Me | H | H |
| 96 | 4'-Me | H | H | OH | H | H |
| 97 | 4'-Me | H | —CH=CH—NH— | | H | H |
| 98 | 4'-Me | H | H | t-Bu | H | H |
| 99 | 4'-Me | H | H | CH₂OH | H | H |
| 100 | 5'-Cl | H | H | t-Bu | H | H |
| 101 | 5'-Cl | H | —S—CH=N— | | H | H |
| 102 | 5'-Cl | H | OMe | OMe | H | H |
| 103 | 5'-Cl | H | —NH—N=CH— | | H | H |
| 104 | 5'-Cl | OMe | H | Cl | OMe | H |
| 105 | 5'-Cl | H | F | OMe | H | H |
| 106 | 5'-Cl | H | H | N-morpholino | H | H |
| 107 | 5'-Cl | H | H | OEt | H | H |
| 108 | 5'-Cl | H | CO₂H | OH | H | H |
| 109 | 5'-Cl | H | CH₂NEt₂ | OH | H | H |
| 110 | 5'-Cl | H | —CH=CH—NH— | | H | H |
| 111 | 5'-Cl | H | H | CH₂OH | H | H |
| 112 | 5'-Cl | H | Me | iPr | H | H |
| 113 | 4'-Me | H | H | CH₂CH₂OH | H | H |
| 114 | 5'-Cl | H | H | NHCOMe | H | H |
| 115 | 5'-Cl | H | H | CH₂CO₂H | H | H |
| 116 | 5'-Cl | H | H | SO₂NH₂ | H | H |
| 117 | 4'-Me | H | OH | OMe | H | H |
| 118 | 4'-Me | H | CO₂H | OH | H | H |
| 119 | 4'-Me | H | H | OCHF₂ | H | H |
| 120 | 4'-Me | H | H | OCF₃ | H | H |
| 121 | 4'-Me | H | CF₃ | OMe | H | H |
| 122 | 4'-Me | H | H | OEt | H | H |
| 123 | 4'-Me | H | H | iPr | H | H |
| 124 | 4'-Me | H | —O—CH₂—O— | | H | H |
| 125 | 4'-Me | H | OH | Me | H | H |
| 126 | 4'-Me | H | OMe | OMe | H | H |
| 127 | 4'-Me | Et | H | H | H | H |
| 128 | 4'-Me | H | H | CN | H | H |
| 129 | 4'-Me | H | H | CONH₂ | H | H |
| 130 | 4'-Me | H | H | NHCOCH₃ | H | H |
| 131 | 4'-Me | H | H | CH₂CO₂H | H | H |
| 132 | 4'-Me | H | Me | OH | H | H |
| 133 | H | H | Me | OH | H | H |
| 134 | H | H | OH | NHCO₂Et | H | H |
| 135 | 4'-Me | F | H | OMe | H | H |
| 136 | H | H | H | SMe | H | H |
| 137 | 4'-Me | H | H | SMe | H | H |
| 138 | 5'-Cl | H | H | SMe | H | H |
| 139 | H | H | H | —CH₂CH₂CH₂CO₂H | H | H |
| 140 | 4'-Me | H | H | —CH₂CH₂CH₂CO₂H | H | H |
| 141 | H | H | —CH₂CH₂CO₂H | H | H | H |
| 142 | 4'-Me | H | —CH₂CH₂CO₂H | H | H | H |
| 143 | 5'-Cl | H | —CH₂CH₂CO₂H | H | H | H |
| 144 | H | H | H | —CH₂CH₂CO₂H | H | H |
| 145 | 4'-Me | H | H | —CH₂CH₂CO₂H | H | H |
| 146 | 5'-Cl | H | H | —CH₂CH₂CO₂H | H | H |

TABLE 1-continued

Unsubstituted, 4-methyl, 5-Chloro & 5-Fluoro 3-[(Substituted Phenylamino)-methylene]-1,3-dihydro-indol-2-ones.

| Example # | R¹ | R Substitution | | | | |
|---|---|---|---|---|---|---|
| | | 2 | 3 | 4 | 5 | 6 |
| 147 | 4'-Me | H | Et | H | H | H |
| 148 | 5'-Cl | H | Et | H | H | H |
| 149 | 5'-Cl | H | H | Et | H | H |
| 150 | 5'-Cl | H | H | —CH$_2$CH$_2$CH$_2$CO$_2$H | H | H |
| 151 | 4'-Me | H | H | Et | H | H |
| 152 | 5'-Cl | H | H | —CN | H | H |
| 155 | 4'-Me | H | OH | CO$_2$H | H | H |
| 156 | H | H | H | N(Me)$_2$ | H | H |
| 157 | H | H | H | N-piperazine-NMe | H | H |
| 158 | H | H | H | N-piperidine | H | H |
| 159 | H | H | H | 2,6-dimethylmorpholine | H | H |
| 160 | H | H | CH$_2$N(Et)$_2$ | OH | H | H |
| 161 | 4'-Me | H | CH$_2$N(Et)$_2$ | OH | H | H |
| 162 | 5'-F | H | —CH=CH—NH— | | H | H |
| 163 | 5'-F | H | —NH—N=CH— | | H | H |
| 164 | 5'-F | H | OH | OMe | H | H |
| 165 | 5'-F | H | H | CH$_2$CH$_2$CO$_2$H | H | H |
| 166 | 5'-F | H | H | SO$_2$NH$_2$ | H | H |
| 167 | 5'-F | H | H | N-morpholine | H | H |
| 168 | 5'-F | H | H | N-piperazine-NMe | H | H |
| 169 | 5'-F | H | H | H | H | H |
| 170 | 5'-F | H | H | CONH$_2$ | H | H |
| 171 | 5'-F | H | H | SMe | H | H |
| 172 | 5'-F | H | F | OMe | H | H |
| 173 | 5'-F | H | —S—CH=N— | | H | H |
| 174 | 5'-F | H | H | CH$_2$CO$_2$H | H | H |
| 175 | 5'-F | H | CH$_2$CH$_2$CO$_2$H | H | H | H |
| 176 | 5'-F | H | Et | H | H | H |
| 177 | 5'-F | H | OH | H | H | H |
| 178 | 5'-F | H | H | CH$_2$OH | H | H |
| 179 | H | H | H | H | H | H |
| 180 | H | H | H | NH$_2$ | H | H |
| 181 | 4'-Me | H | H | NH$_2$ | H | H |

TABLE 1-continued

| Example # | R¹ | 2 | 3 | 4 | 5 | 6 |
|---|---|---|---|---|---|---|
| 182 | H | H | CH(OH)CH₃ | H | H | H |
| 183 | 4'-Me | H | CH(OH)CH₃ | H | H | H |
| 184 | H | H | CH₂OH | H | H | H |
| 185 | 4'-Me | H | CH₂OH | H | H | H |
| 186 | H | H | NHCO₂t-Bu | H | H | H |
| 187 | 4'-Me | H | NHCO₂t-Bu | H | H | H |
| 188 | H | H | H | N(Et)₂ | H | H |
| 189 | 4'-Me | H | H | N(Et)₂ | H | H |
| 190 | H | H | SO₂N(CH₂CH₂OH)₂ | H | H | H |
| 191 | 4'-Me | H | SO₂N(CH₂CH₂OH)₂ | H | H | H |
| 192 | H | H | H | SO₂NCH₂CH₂OH | H | H |
| 193 | H | H | SO₂NCH₂CH₂CH₂OH | H | H | H |
| 194 | 4'-Me | H | SO₂NCH₂CH₂CH₂OH | H | H | H |
| 195 | H | H | CO₂H | 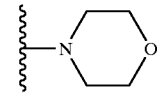 | H | H |
| 196 | 4'-Me | H | H | 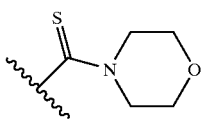 | H | H |
| 197 | 4'-Me | H | H | SO₂NCH₂CH₂OH | H | H |
| 198 | H | H | H | OCH₂CH₂CH₂Cl | H | H |
| 199 | H | H | H | OCH₂CH₂CH₂CH₂Cl | H | H |
| 200 | H | H | H | OCH₂CH₂CH₂I | H | H |
| 201 | H | H | H | OCH₂CH₂CH₂CH₂I | H | H |
| 202 | 4'-Me | D | D | D | D | D |
| 203 | H | D | D | CO₂H | D | D |
| 204 | H | D | D | NH₂ | D | D |
| 205 | 4'-Me | D | D | NH₂ | D | D |
| 206 | H | H | H | 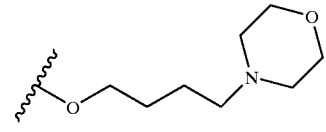 | H | H |
| 207 | H | H | H | OCH₂CH₂CH₂CH₂N(Et)₂ | H | H |
| 208 | H | H | H | 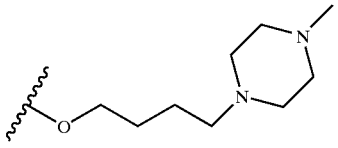 | H | H |
| 209 | H | H | H | 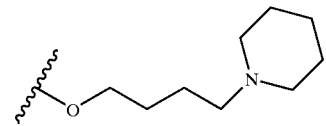 | H | H |
| 210 | 4'-Me | H | NH₂ | H | H | H |
| 211 | H | H | NH₂ | H | H | H |
| 212 | H | H | NH₂ | Me | H | H |
| 213 | 4'-Me | H | NH₂ | Me | H | H |
| 214 | H | H | H | OCH₂CH₂CH₂N(Et)₂ | H | H |
| 215 | H | H | H | 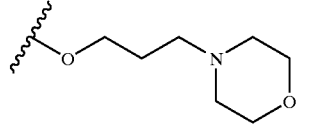 | H | H |

TABLE 1-continued
| Example # | R¹ | 2 | 3 | 4 | 5 | 6 |
|---|---|---|---|---|---|---|
| 216 | H | H | H | 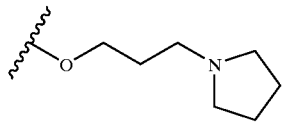 | H | H |
| 217 | H | H | H | 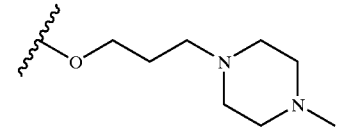 | H | H |
| 218 | H | H | H | 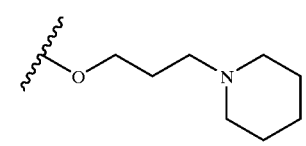 | H | H |
| 219 | 5'-F | H | H | 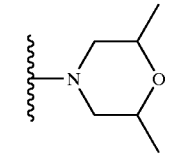 | H | H |
| 220 | 4'-Me | H | H | 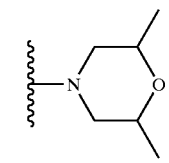 | H | H |
Unsubstituted, 4-Fluoro, 4-methyl, 5-Chloro, 5-Cyano, 5-Fluoro, 5-Nitro, 6-Fluoro & 6-Aryl 3-[(Substituted Phenylamino)-methylene]-1,3-dihydro-indol-2-ones.
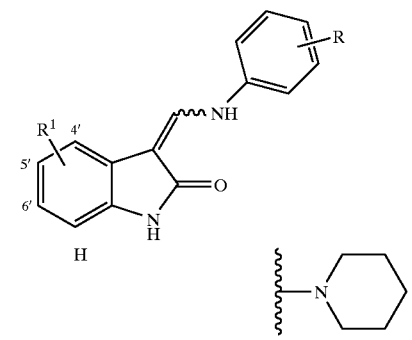
| Example # | R¹ | 2 | 3 | 4 | 5 | 6 |
|---|---|---|---|---|---|---|
| 221 | 5'-F | H | H | 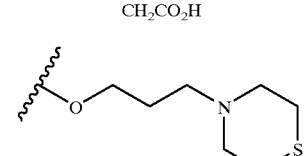 | H | H |
| 222 | 5'-F | H | H | OMe | H | H |
| 223 | H | D | D | D | D | D |
| 224 | H | H | H | CH₂CO₂H | H | H |
| 225 | H | H | H | 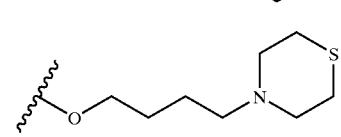 | H | H |
| 226 | H | H | H | | H | H |

TABLE 1-continued
| Example # | R¹ | 2 | 3 | 4 | 5 | 6 |
|---|---|---|---|---|---|---|
| 227 | 4'-Me | H | H | 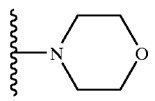 | H | H |
| 228 | 6'-F | H | H | 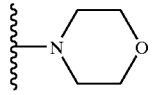 | H | H |
| 229 | 6'-F | H | H | 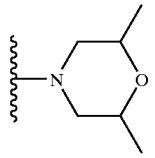 | H | H |
| 230 | 6'-F | H | H | 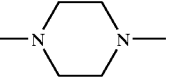 | H | H |
| 231 | 4'-Me | H | H | 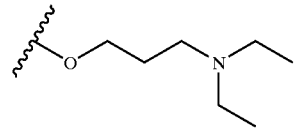 | H | H |
| 232 | 5'-Cl | H | H | 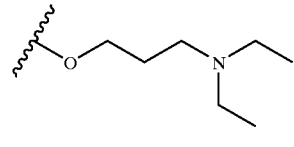 | H | H |
| 233 | 5'-F | H | H | 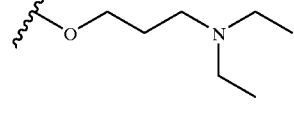 | H | H |
| 234 | 6'-F | H | H | 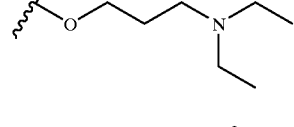 | H | H |
| 235 | H | H | H | 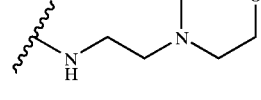 | H | H |
| 236 | 5'-NO₂ | H | H | 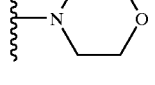 | H | H |
| 237 | 5'-CN | H | H | 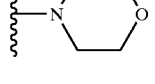 | H | H |

TABLE 1-continued
| Example # | R¹ | 2 | 3 | 4 | 5 | 6 |
|---|---|---|---|---|---|---|
| 238 | 4'-Me | H | H | 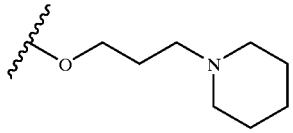 | H | H |
| 239 | 6'-F | H | H | 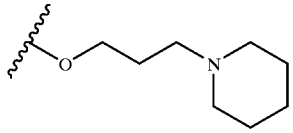 | H | H |
| 240 | 5'-F | H | H | 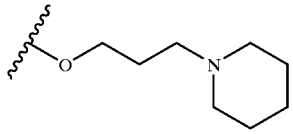 | H | H |
| 241 | 5'-Cl | H | H | 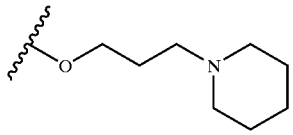 | H | H |
| 242 | 4'-Me | H | H | 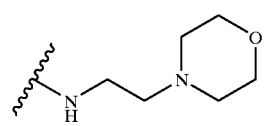 | H | H |
| 243 | 6'-F | H | H | 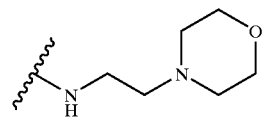 | H | H |
| 244 | 5'-F | H | H | 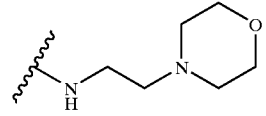 | H | H |
| 245 | 5'-Cl | H | H | 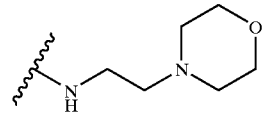 | H | H |
| 246 | 4'-Me | H | H | 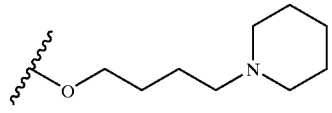 | H | H |
| 247 | 6'-F | H | H | 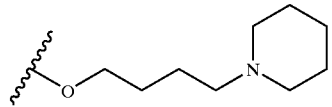 | H | H |
| 248 | H | H | F | 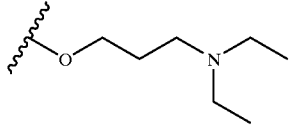 | H | H |

TABLE 1-continued
| Example # | R¹ | 2 | 3 | 4 | 5 | 6 |
|---|---|---|---|---|---|---|
| 249 | 4'-Me | H | F | 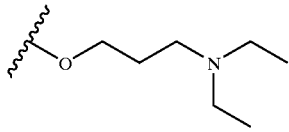 | H | H |
| 250 | 6'-F | H | F | 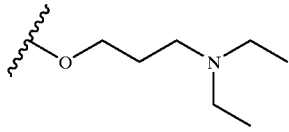 | H | H |
| 251 | H | H | H | 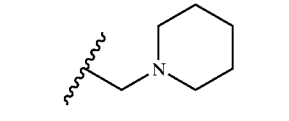 | H | H |
| 252 | 4'-Me | H | H | 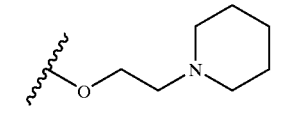 | H | H |
| 253 | 6'-F | H | H | 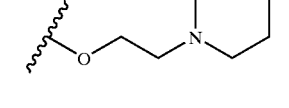 | H | H |
| 254 | H | H | H | 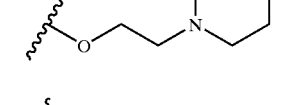 | H | H |
| 255 | 4'-F | H | H | 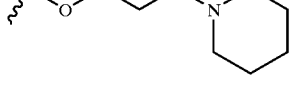 | H | H |
| 256 | 4'-Me | H | H | 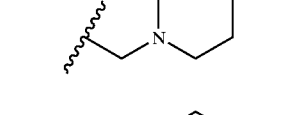 | H | H |
| 257 | 4'-F | H | H | 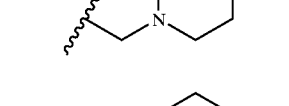 | H | H |
| 258 | 5'-F | H | H | 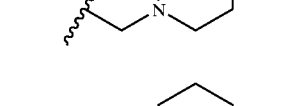 | H | H |
| 259 | 6'-F | H | H | 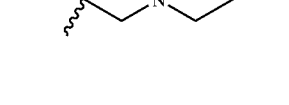 | H | H |

TABLE 1-continued
| Example # | R¹ | 2 | 3 | 4 | 5 | 6 |
|---|---|---|---|---|---|---|
| 260 | 5'-Cl | H | H | 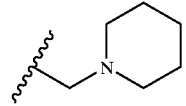 | H | H |
| 261 | 4'-F | H | H | 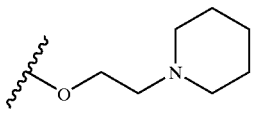 | H | H |
| 262 | 5'-Cl | H | H | 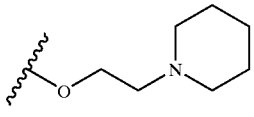 | H | H |
| 263 | 5'-F | H | H | 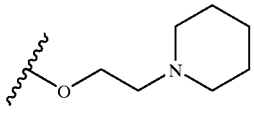 | H | H |
| 264 | 4'-Me | H | H | 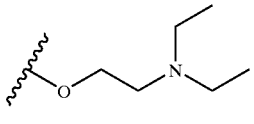 | H | H |
| 265 | H | H | H | 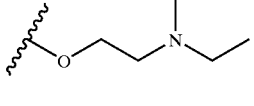 | H | H |
| 266 | 6'-F | H | H | 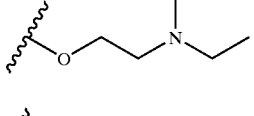 | H | H |
| 267 | 4'-F | H | H | 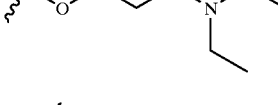 | H | H |
| 268 | 6'-(3-Methoxyphenyl) | H | H | 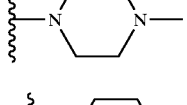 | H | H |
| 269 | 6'-(3-Methoxyphenyl) | H | H | 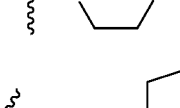 | H | H |
| 270 | 4'-Me | H | H | 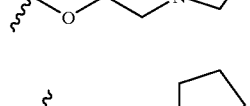 | H | H |
| 271 | 6'-F | H | H | 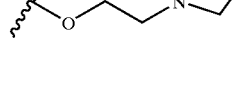 | H | H |

TABLE 1-continued
| Example # | R¹ | \multicolumn{5}{c}{R Substitution} |
| | | 2 | 3 | 4 | 5 | 6 |
|---|---|---|---|---|---|---|
| 272 | H | H | H | 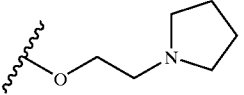 | H | H |
| 273 | 4'-F | H | H | 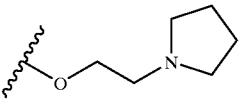 | H | H |
| 274 | 5'-F | H | H | 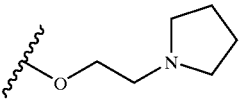 | H | H |
| 275 | 5'-Cl | H | H | 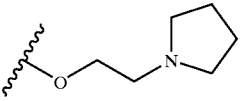 | H | H |
| 276 | 6'-(3-Methoxyphenyl) | H | H | 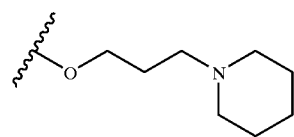 | H | H |
| 277 | 6'-(3-Methoxyphenyl) | H | H | 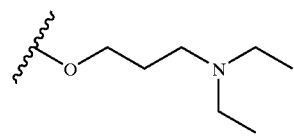 | H | H |
| 278 | 4'-Me | H | H | 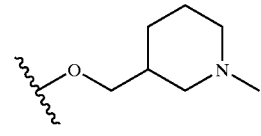 | H | H |
| 279 | 6'-F | H | H | 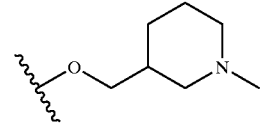 | H | H |
| 280 | H | H | H | 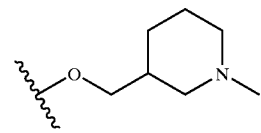 | H | H |
| 281 | 4'-F | H | H | 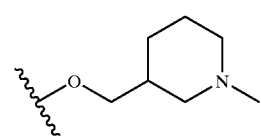 | H | H |
| 282 | 5'-F | H | H | 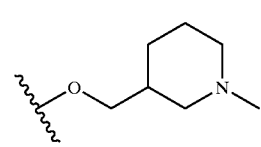 | H | H |

TABLE 1-continued
| Example # | R¹ | 2 | 3 | 4 | 5 | 6 |
|---|---|---|---|---|---|---|
| 283 | 5'-Cl | H | H | 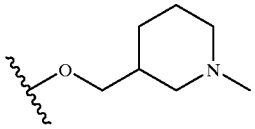 | H | H |
| 284 | H | H | H | 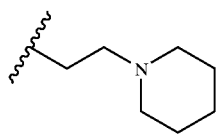 | H | H |
| 285 | 5'-Cl | H | H | 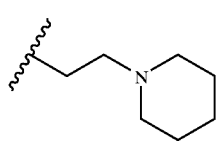 | H | H |
| 286 | 4'-Me | H | H | 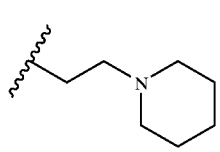 | H | H |
| 287 | 4'-F | H | H | 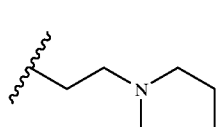 | H | H |
| 288 | 5'-F | H | H | 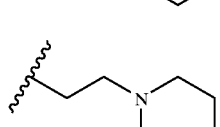 | H | H |
| 289 | 6'-F | H | H | 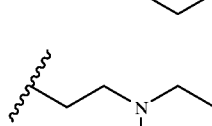 | H | H |
| 290 | H | H | H | 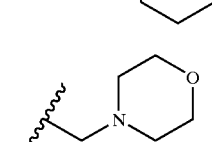 | H | H |
| 291 | 5'-Cl | H | H | 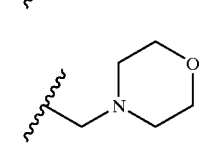 | H | H |
| 292 | 4'-Me | H | H | 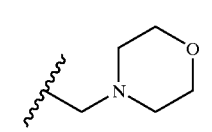 | H | H |
| 293 | 4'-F | H | H | 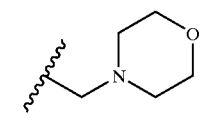 | H | H |

TABLE 1-continued

| Example # | R¹ | R Substitution | | | | |
|---|---|---|---|---|---|---|
| | | 2 | 3 | 4 | 5 | 6 |
| 294 | 5'-F | H | H | ~CH₂-morpholine | H | H |
| 295 | 6'-F | H | H | ~CH₂-morpholine | H | H |
| 296 | 4'-Me | H | H | ~NH-(CH₂)₃-morpholine | H | H |
| 297 | H | H | H | ~NH-(CH₂)₃-morpholine | H | H |
| 298 | 6'-F | H | H | ~NH-(CH₂)₃-morpholine | H | H |
| 299 | 5'-Cl | H | H | ~NH-(CH₂)₃-morpholine | H | H |
| 300 | 5'-F | H | H | ~NH-(CH₂)₃-morpholine | H | H |
| 301 | 4'-F | H | H | ~NH-(CH₂)₃-morpholine | H | H |
| 302 | H | H | H | ~NH-(CH₂)₃-(N-methylpiperazine) | H | H |
| 303 | 4'-Me | H | H | ~NH-(CH₂)₃-(N-methylpiperazine) | H | H |

TABLE 1-continued
| Example # | R¹ | 2 | 3 | 4 | 5 | 6 |
|---|---|---|---|---|---|---|
| 304 | 6'-F | H | H | 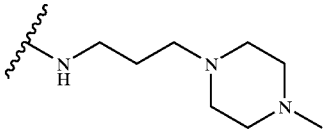 | H | H |
Unsubstituted, 4-Fluoro, 4-methyl, 5-Chloro, 5-Fluoro & 6-Fluoro 3-[(Substituted Phenylamino)-methylene]-1,3-dihydro-indol-2-ones.
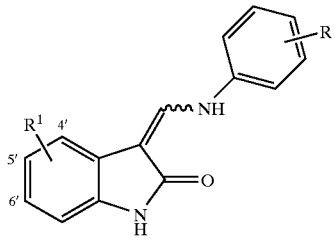
| Example # | R¹ | 2 | 3 | 4 | 5 | 6 |
|---|---|---|---|---|---|---|
| 305 | H | H | H | 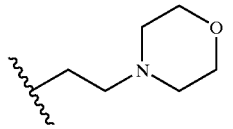 | H | H |
| 306 | H | H | H | 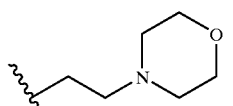 | H | H |
| 307 | 5'-Cl | H | H | 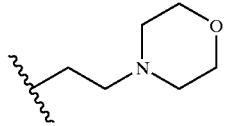 | H | H |
| 308 | 4'-Me | H | H | 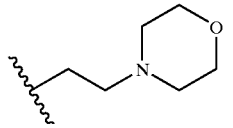 | H | H |
| 309 | 4'-F | H | H | 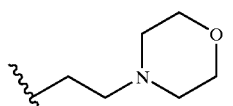 | H | H |
| 310 | 5'-F | H | H | 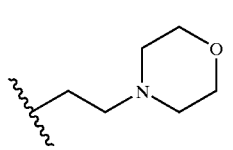 | H | H |
| 311 | 6'-F | H | H | | H | H |

TABLE 1-continued

| Example # | R¹ | R Substitution | | | | |
|---|---|---|---|---|---|---|
| | | 2 | 3 | 4 | 5 | 6 |
| 312 | H | H | H | morpholine-butyl | H | H |
| 313 | 5'-Cl | H | H | morpholine-butyl | H | H |
| 314 | 4'-Me | H | H | morpholine-butyl | H | H |
| 315 | 4'-F | H | H | morpholine-butyl | H | H |
| 316 | 5'-F | H | H | morpholine-butyl | H | H |
| 317 | 6'-F | H | H | morpholine-butyl | H | H |
| 318 | H | H | H | piperidine-butyl | H | H |
| 319 | 5'-Cl | H | H | piperidine-butyl | H | H |
| 320 | 4'-Me | H | H | piperidine-butyl | H | H |
| 321 | 4'-F | H | H | piperidine-butyl | H | H |

TABLE 1-continued

| Example # | R¹ | 2 | 3 | 4 | 5 | 6 |
|---|---|---|---|---|---|---|
| 322 | 5'-F | H | H | 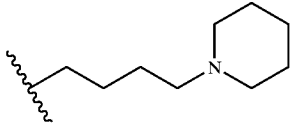 | H | H |
| 323 | 6'-F | H | H | 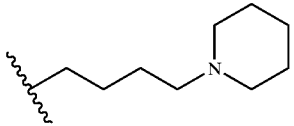 | H | H |

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The following defined terms are used throughout this specification:

"Me" refers to methyl.
"Et" refers to ethyl.
"tBu" refers to t-butyl.
"iPr" refers to i-propyl.
"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, NO$_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, =O, =S, NO$_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, =O, =S, NO$_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, NO$_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R'"', where R'"' is aryl, C(CN)=C-aryl, CH$_2$CN, alkyaryl, sulfonamide, NH-alkyl, NH-alkylaryl, or NH-aryl.

Also, alternatively the substituent on the aniline moiety is referred to as an o, m or p substituent or a 2, 3 or 4 substituent, respectively. (Obviously, the 5 substituent is also a m substituent and the 6 substituent is an o substituent.

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

Biological data for the compounds of the present invention was generated by use of the following assays.

VEGF Stimulated $Ca^{++}$ Signal in Vitro

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 96-well fibronectin coated black-walled plates overnight at 37° C./5% $CO_2$. Cells were loaded with calcium indicator Fluo-4 for 45 minutes at 37° C. Cells were washed 4 times (Original Cell Wash, Labsystems) to remove extracellular dye. Test compounds were reconstituted in 100% DMSO and added to the cells to give a final DMSO concentration of 0.1%. For screening, cells were pre-incubated with test agents for 30 minutes, at a single concentration (10 $\mu$M) or at concentrations ranging from 0.01 to 10.0 $\mu$M followed by VEGF stimulation (5 ng/1 mL). Changes in fluorescence at 516 nm were measured simultaneously in all 96 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

Protocol for KDR Assay:

KDR Assay:

The cytoplasmic domain of the human VEGF receptor (VEGFR-2) was expressed as a Histidine-tagged fusion protein following infection of insect cells using an engineered baculovirus. His-VEGFR-2 was purified to homogeneity, as determined by SDS-PAGE, using nickel resin chromatography. Kinase assays were performed in 96 well microtiter plates that were coated overnight with 30 $\mu$g of poly-Glu-Tyr (4:1) in 10 mM Phosphate Buffered Saline (PBS), pH 7.2–7.4. The plates were incubated with 1% BSA and then washed four times with PBS prior to starting the reaction. Reactions were carried out in 120 $\mu$L reaction volumes containing 3.6 $\mu$M ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 0.5 ng of purified protein. Following a ten minute incubation at 25° C., the reactions were washed four times with PBS containing 0.05% Tween-20. 100 $\mu$l of a monoclonal anti-phosphotyrosine antibody-peroxidase conjugate was diluted 1:10000 in PBS-Tween-20 and added to the wells for 30 minutes. Following four washes with PBS-Tween-20, 100%1 of O-phenylenediamine Dihydrochloride in Phosphate-citrate buffer, containing urea hydrogen peroxide, was added to the wells for 7 minutes as a colorimetric substrate for the peroxidase. The reaction was terminated by the addition of 100%1 of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

VEGF-Induced Dermal Extravasation in Guinea Pig (Miles Assay). Male Hartley guinea pigs (300–600 g) were anesthetized with isofluorane, sheared, and given a single dose of drug or the respective vehicle. The guinea pigs were dosed orally unless indicated otherwise in Table 3. Ten minutes prior to the end of drug treatment, guinea pigs were anesthetized with isofluorane, and 0.5% Evans blue dye (EBD) in PBS (13–15 mg/kg dose of EBD) was injected intravenously. After 5 minutes, triplicate intradermal injections of 100 ng rh VEGF$_{165}$ in 100 μl PBS and of 100 μl PBS alone were administered on the flank. After 20 minutes, each animal was euthanized with Pentosol, and the skin containing the intradermal injection sites was removed for image analysis.

Using an analog video camera coupled to a PC, an image of each trans-illuminated skin sample was captured, and the integrated optical density of each injection site was measured using ImagePro 4. For each skin sample, the difference between the mean optical density of the VEGF sites and mean optical density of the PBS sites is the measure of VEGF-induced EBD extravasation in that animal. These measured values were averaged per study group to determine the mean VEGF-induced EBD extravasation for each experimental condition, and the group means were then compared to assess inhibition of VEGF-induced EBD extravasation in the drug-treated groups relative to the vehicle-treated controls.

To determine the dose required for 50% inhibition (ID$_{50}$), the percent inhibition data was plotted as a function of oral dose, using the 'best-fit' analysis within MicroSoft Excel software. The ID$_{50}$ value was verified visually by using the plotted data (horizontal line from 50% y value, at intersection with best-fit line drop vertical line to x axis (dose)).

Laser-Induced Choroidal Neovascularization (CNV) in Rat (CNV Assay).

CNV was induced and quantified in this model as previously described (Edelman and Castro. *Exp. Eye Res.* 2000; 71:523–533). On day 0, male Brown Norway rats (200–300 g) were anesthetized with 100 mg/kg Ketamine and 10 mg/kg Xylazine, and pupils were dilated with 1% Tropicamide. Using the blue-green setting of a Coherent Novus Argon Laser, 3 laser burns (90 mW for 0.1 s; 100 μm diameter) were given to each eye between the retinal vessels around the optic nerve head. Rats were dosed with test compounds in their indicated vehicles orally once daily.

On day 10, rats were sacrificed with 100% CO$_2$, and blood vessels were labeled by vascular perfusion with 10 mg/ml FITC-dextran (MW 2×10$^6$). Using an epifluorescence microscope (20×) coupled to a spot digital camera and a PC, images were obtained from the flat mounts of the RPE-choroid-sclera from each eye, and the area occupied by hyperfluorescent neovessels within each laser lesion was measured using ImagePro 4 software.

To determine the dose required for 50% inhibition (ID$_{50}$), the percent inhibition data was plotted as a function of oral dose, using the 'best-fit' analysis within MicroSoft Excel software. The ID$_{50}$ value was verified visually by using the plotted data (horizontal line from 50% y value, at intersection with best-fit line drop vertical line to x axis (dose)).

The results of said assays are set forth in Tables 2, 3 and 4 below, wherein NT means not tested.

TABLE 2

| | Kinase Inhibition Data | | |
|---|---|---|---|
| Example # | VEGF Stimulated Ca$^{++}$signal assay % inhibition @ 10 μM | VEGF Stimulated Ca$^{++}$signal assay mean IC$_{50}$(μM) | KDR Assay mean IC$_{50}$(μM) |
| 1 | 92 | 4.05 | NT |
| 2 | −0.5 | NT | NT |
| 3 | 3.50 | NT | NT |
| 4 | 16.5 | NT | NT |

TABLE 2-continued

| | Kinase Inhibition Data | | |
|---|---|---|---|
| Example # | VEGF Stimulated Ca$^{++}$signal assay % inhibition @ 10 μM | VEGF Stimulated Ca$^{++}$signal assay mean IC$_{50}$(μM) | KDR Assay mean IC$_{50}$(μM) |
| 5 | 77.280 | 1.82 | 0.48 |
| 6 | 90.06 | 1.84 | 0.52 |
| 7 | 94.50 | 0.95 | 0.69 |
| 8 | 9 | NT | NT |
| 9 | 13.50 | NT | NT |
| 10 | 46.00 | 10 | NT |
| 11 | −14 | NT | NT |
| 12 | 94.25 | 1.07 | NT |
| 13 | −12.50 | NT | NT |
| 14 | −14.00 | NT | NT |
| 15 | 93.70 | 0.19 | 0.91 |
| 16 | 50 | 10 | 1.27 |
| 17 | 76.5 | 3.00 | 0.79 |
| 18 | 35.5 | NT | NT |
| 19 | 14 | NT | NT |
| 20 | 63 | 1.82 | 1.21 |
| 21 | 88 | 1.50 | 0.72 |
| 22 | 22.5 | NT | NT |
| 23 | 42 | NT | NT |
| 24 | −13.5 | NT | NT |
| 25 | −1.5 | NT | NT |
| 26 | 37.5 | NT | NT |
| 27 | −9 | NT | NT |
| 28 | 32.5 | NT | NT |
| 29 | 81.50 | 7.29 | 0.68 |
| 30 | 39.50 | NT | NT |
| 31 | 98.56 | 0.72 | 0.57 |
| 32 | 72.20 | 2.66 | 0.60 |
| 33 | 95.86 | 1.35 | 0.88 |
| 34 | 94.50 | 2.25 | 0.47 |
| 35 | 95.10 | 3.10 | 0.19 |
| 36 | 30.00 | NT | NT |
| 37 | −4.00 | NT | NT |
| 38 | 92.08 | 1.45 | 0.50 |
| 39 | −14.50 | NT | NT |
| 40 | 96.71 | 0.25 | 0.25 |
| 41 | 16.00 | NT | NT |
| 42 | 59.50 | NT | NT |
| 43 | 84.00 | 1.74 | 0.23 |
| 44 | 96.00 | 2.02 | 0.66 |
| 45 | 50.00 | NT | NT |
| 46 | −4.00 | NT | NT |
| 47 | −2.50 | NT | NT |
| 48 | 95.44 | 0.42 | 0.74 |
| 49 | 97.11 | 0.10 | 0.51 |
| 50 | 93.50 | 1.65 | 0.55 |
| 51 | 45.50 | NT | NT |
| 52 | 69.00 | 2.28 | 0.58 |
| 53 | 2.50 | NT | NT |
| 54 | 40.50 | NT | NT |
| 55 | 14.50 | NT | NT |
| 56 | 21.00 | NT | NT |
| 57 | 60.00 | 5.85 | 1.88 |
| 58 | 86.61 | 0.81 | 0.36 |
| 59 | 86.00 | 1.65 | 0.18 |
| 60 | 94.00 | 1.33 | 0.28 |
| 61 | −4.50 | NT | NT |
| 62 | 33.00 | NT | NT |
| 63 | −14.50 | NT | NT |
| 64 | 37.00 | NT | NT |
| 65 | 95.50 | 1.10 | 0.53 |
| 66 | 18.50 | NT | NT |
| 67 | 19.00 | NT | NT |
| 68 | −2.50 | NT | NT |
| 69 | −10.68 | NT | NT |
| 70 | 25.00 | NT | NT |
| 71 | 38.50 | NT | NT |
| 72 | 81.50 | 1.56 | 0.43 |
| 73 | 56.50 | 3.65 | 0.26 |
| 74 | 44.00 | NT | NT |
| 75 | −18.00 | NT | NT |
| 76 | 55.50 | NT | NT |

TABLE 2-continued

Kinase Inhibition Data

| Example # | VEGF Stimulated Ca++signal assay % inhibition @ 10 μM | VEGF Stimulated Ca++signal assay mean IC$_{50}$(μM) | KDR Assay mean IC$_{50}$(μM) |
|---|---|---|---|
| 77 | 35.00 | NT | NT |
| 78 | 8.00 | NT | NT |
| 79 | −4.00 | NT | NT |
| 80 | 3.50 | NT | NT |
| 81 | NT | NT | NT |
| 82 | NT | 2.5 | 0.38 |
| 83 | NT | NT | NT |
| 84 | 11.50 | NT | NT |
| 85 | NT | NT | NT |
| 86 | 48.50 | NT | NT |
| 87 | 79.50 | 2.25 | 0.46 |
| 88 | 97.51 | 1.00 | 0.41 |
| 89 | 39.50 | NT | NT |
| 90 | 97.81 | 0.42 | 0.22 |
| 91 | 93.50 | 3.02 | 0.24 |
| 92 | 69.00 | 1.77 | 0.15 |
| 93 | 51.50 | 6.62 | 0.63 |
| 94 | 92.50 | 3.88 | 0.64 |
| 95 | 14.00 | NT | NT |
| 96 | 97.00 | 1.68 | 0.20 |
| 97 | 96.50 | 1.86 | 0.20 |
| 98 | 47.50 | NT | NT |
| 99 | 97.80 | 0.48 | 0.21 |
| 100 | 6.00 | NT | NT |
| 101 | 22.00 | NT | NT |
| 102 | 82.50 | 5.91 | 0.65 |
| 103 | 96.59 | 1.04 | 0.48 |
| 104 | −14.50 | NT | NT |
| 105 | 17.50 | NT | NT |
| 106 | 96.59 | 0.60 | 0.23 |
| 107 | 41.50 | NT | NT |
| 108 | −14.50 | NT | NT |
| 109 | 96.50 | 1.70 | 0.60 |
| 110 | 95.00 | 1.55 | 0.57 |
| 111 | 98.50 | 1.17 | 0.43 |
| 112 | 10.50 | NT | NT |
| 113 | 97.52 | 035 | 0.20 |
| 114 | 88.96 | 1.93 | 0.92 |
| 115 | 98.23 | 3.08 | 0.47 |
| 116 | 99.37 | 1.64 | 0.98 |
| 117 | 97.72 | 0.29 | 0.31 |
| 118 | −26.96 | NT | NT |
| 119 | 89.28 | 1.34 | 0.53 |
| 120 | 12.67 | NT | NT |
| 121 | 4.86 | NT | NT |
| 122 | 71.71 | 1.54 | 0.37 |
| 123 | 49.94 | 4.43 | 0.59 |
| 124 | 71..93 | 1.96 | 0.52 |
| 125 | 96.55 | 1.86 | 0.67 |
| 126 | 95.15 | 1.22 | 0.34 |
| 127 | −11.79 | NT | NT |
| 128 | 42.88 | 8.26 | 0.46 |
| 129 | 99.00 | 1.27 | NT |
| 130 | 97.31 | 0.57 | 0.38 |
| 131 | 96.71 | 1.55 | 0.77 |
| 132 | 73 | 7.38 | NT |
| 133 | 73 | 4.91 | NT |
| 134 | 83.09 | 7.39 | 1.12 |
| 135 | 27.98 | NT | 7.77 |
| 136 | 63.74 | 2.07 | 0.49 |
| 137 | 65.36 | 1.67 | 0.27 |
| 138 | 80.90 | 7.07 | 0.73 |
| 139 | 99.26 | 1.62 | 0.53 |
| 140 | 96.89 | 0.46 | 0.40 |
| 141 | 92.56 | 2.96 | 0.51 |
| 142 | 99.27 | 4.16 | 0.21 |
| 143 | 66.92 | 7.61 | 0.52 |
| 144 | 96.51 | 2.70 | 0.46 |
| 145 | 98.73 | 0.59 | 0.19 |
| 146 | 98.38 | 2.07 | 0.51 |
| 147 | 71.57 | 5.49 | 0.15 |
| 148 | 42.22 | NT | NT |
| 149 | 17.67 | NT | 0.62 |
| 150 | 90.86 | 1.85 | 0.30 |
| 151 | 50.83 | NT | 0.46 |
| 152 | 18.73 | NT | 10 |
| 155 | 97.15 | 2.60 | 0.40 |
| 156 | 95.36 | 0.83 | 0.51 |
| 157 | 97.89 | 0.23 | 0.25 |
| 158 | 97.55 | 1.14 | 0.39 |
| 159 | 97.42 | 0.58 | 0.35 |
| 160 | 91.44 | 1.29 | 0.70 |
| 161 | 95.23 | 0.46 | 0.16 |
| 162 | 89.94 | 1.05 | 0.30 |
| 163 | 95.34 | 0.85 | 0.32 |
| 164 | 98.82 | 0.16 | 0.38 |
| 165 | 99.33 | 1.34 | 0.36 |
| 166 | 49.17 | NT | 0.66 |
| 167 | 95.67 | 0.36 | 0.19 |
| 168 | 94.33 | 0.15 | 0.14 |
| 169 | 93.44 | 1.16 | 0.61 |
| 170 | 96.67 | 0.59 | 0.41 |
| 171 | 38.07 | NT | 0.43 |
| 172 | 93.33 | 1.40 | 0.69 |
| 173 | 94.54 | 1.48 | 0.52 |
| 174 | 76.40 | 6.02 | 0.84 |
| 175 | 38.03 | NT | 0.71 |
| 176 | 67.88 | 2.54 | 0.80 |
| 177 | 98.17 | 0.74 | 0.75 |
| 178 | 98.78 | 1.06 | 0.53 |
| 179 | 97.35 | 0.64 | 0.31 |
| 180 | 98.33 | 1.03 | 0.44 |
| 181 | 97.73 | 0.49 | 0.35 |
| 182 | 99.29 | 0.95 | 1.65 |
| 183 | 98.88 | 0.75 | 0.52 |
| 184 | 98.21 | 1.56 | 0.61 |
| 185 | 98.44 | 0.87 | 0.33 |
| 186 | 99.03 | 1.92 | 0.89 |
| 187 | 96.84 | 1.67 | 0.27 |
| 188 | 98.04 | 0.53 | 0.18 |
| 189 | 98.16 | 0.34 | 0.07 |
| 190 | 54.11 | 9.99 | 6.96 |
| 191 | 98.65 | 2.41 | 0.70 |
| 192 | 98.66 | 1.53 | 0.59 |
| 193 | 81.51 | 4.77 | 2.47 |
| 194 | 96.91 | 2.67 | 0.66 |
| 195 | 91.12 | 4.67 | 0.96 |
| 196 | 73.10 | 0.77 | 0.05 |
| 197 | 98.08 | 0.32 | 0.09 |
| 198 | 56.28 | 7.92 | 0.47 |
| 199 | 32.43 | NT | 0.29 |
| 200 | 75.19 | 3.48 | 0.74 |
| 201 | 44.15 | NT | 0.91 |
| 202 | NT | NT | NT |
| 203 | NT | NT | NT |
| 204 | NT | NT | NT |
| 205 | NT | NT | NT |
| 206 | 96.28 | 0.67 | 0.24 |
| 207 | 98.64 | 0.51 | 0.24 |
| 208 | 99.04 | 0.53 | 0.26 |
| 209 | 98.61 | 0.48 | 0.24 |
| 210 | 97.40 | 0.49 | 0.17 |

TABLE 2-continued

Kinase Inhibition Data

| Example # | VEGF Stimulated Ca++ signal assay % inhibition @ 10 μM | VEGF Stimulated Ca++ signal assay mean IC$_{50}$(μM) | KDR Assay mean IC$_{50}$(μM) |
|---|---|---|---|
| 211 | 96.69 | 0.66 | 0.46 |
| 212 | 96.51 | 0.82 | 0.50 |
| 213 | 94.97 | 0.65 | 0.15 |
| 214 | 97.35 | 0.35 | 0.33 |
| 215 | 96.66 | 0.67 | 0.34 |
| 216 | 95.31 | 0.57 | 0.34 |
| 217 | 97.68 | 0.86 | 0.28 |
| 218 | 98.12 | 0.44 | 0.17 |
| 219 | 97.38 | 0.62 | 0.22 |
| 220 | 94.93 | 0.30 | 0.06 |
| 221 | 97.59 | 0.93 | 0.38 |
| 222 | 48.76 | NT | 0.47 |
| 223 | NT | NT | NT |
| 224 | 56.18 | 6.31 | 2.27 |
| 225 | 95.70 | 0.56 | 0.29 |
| 226 | 97.97 | 0.70 | 0.28 |
| 227 | 85.90 | 0.17 | 0.05 |
| 228 | 97.25 | 0.15 | 0.08 |
| 229 | 97.19 | 0.23 | 0.11 |
| 230 | 96.39 | 0.05 | 0.08 |
| 231 | 93.29 | 0.19 | 0.07 |
| 232 | 97.09 | 0.86 | 0.16 |
| 233 | 96.89 | 0.37 | 0.19 |
| 234 | 96.09 | 0.17 | 0.11 |
| 235 | 98.20 | 0.28 | 0.24 |
| 236 | 7.20 | NT | 0.97 |
| 237 | 36.44 | NT | 0.71 |
| 238 | 98.39 | 0.78 | 0.06 |
| 239 | 97.65 | 0.19 | 0.15 |
| 240 | 98.32 | 0.41 | 0.23 |
| 241 | 95.81 | 1.01 | 0.13 |
| 242 | 95.82 | 0.13 | 0.07 |
| 243 | 95.63 | 0.10 | 0.11 |
| 244 | 95.98 | 0.20 | 0.19 |
| 245 | 95.54 | 0.47 | 0.14 |
| 246 | NT | 0.36 | 0.09 |
| 247 | NT | 0.48 | 0.20 |
| 248 | NT | 0.71 | 0.63 |
| 249 | NT | 0.38 | 0.07 |
| 250 | NT | 0.30 | 0.15 |
| 251 | NT | 0.46 | 0.14 |
| 252 | NT | 0.29 | 0.15 |
| 253 | NT | 0.19 | 0.17 |
| 254 | NT | 0.47 | 0.50 |
| 255 | NT | 1.30 | 0.44 |
| 256 | NT | 0.67 | 0.19 |
| 257 | NT | 1.63 | 0.51 |
| 258 | NT | 0.72 | 0.56 |
| 259 | NT | 0.22 | 0.30 |
| 260 | NT | 0.88 | 0.30 |
| 261 | NT | 1.06 | 0.39 |
| 262 | NT | 0.87 | 0.21 |
| 263 | NT | 0.47 | 0.36 |
| 264 | NT | 0.26 | 0.07 |
| 265 | NT | 0.53 | 0.61 |
| 266 | NT | 0.12 | 0.17 |
| 267 | NT | 1.42 | 0.23 |
| 268 | NT | 10 | 0.08 |
| 269 | NT | 10 | 1.68 |
| 270 | NT | 0.28 | 0.11 |
| 271 | NT | 0.10 | 0.13 |
| 272 | NT | 0.43 | 0.46 |
| 273 | NT | 1.07 | 0.33 |
| 274 | NT | 0.45 | 0.21 |
| 275 | NT | 0.62 | 0.13 |
| 276 | NT | 8.81 | 0.22 |
| 277 | NT | 10 | 0.25 |
| 278 | NT | 0.18 | 0.08 |
| 279 | NT | 0.17 | 0.16 |
| 280 | NT | 0.42 | 0.46 |
| 281 | NT | 0.73 | 0.32 |
| 282 | NT | 0.34 | 0.33 |
| 283 | NT | 0.94 | 0.15 |
| 284 | NT | 0.25 | 0.25 |
| 285 | NT | 0.56 | 0.11 |
| 286 | NT | 0.13 | 0.04 |
| 287 | NT | 0.62 | 0.11 |
| 288 | NT | 0.30 | 0.33 |
| 289 | NT | 0.42 | 0.26 |
| 290 | NT | 0.44 | 0.58 |
| 291 | NT | 0.66 | 0.21 |
| 292 | NT | 0.14 | 0.09 |
| 293 | NT | 0.88 | 0.47 |
| 294 | NT | 0.40 | 0.38 |
| 295 | NT | 0.13 | 0.18 |
| 296 | NT | 0.16 | 0.14 |
| 297 | NT | 0.42 | 0.39 |
| 298 | NT | 0.10 | 0.34 |
| 299 | NT | 0.49 | 0.14 |
| 300 | NT | 0.29 | 0.42 |
| 301 | NT | 0.77 | 0.27 |
| 302 | NT | 0.71 | NT |
| 303 | NT | 0.52 | NT |
| 304 | NT | 0.12 | NT |
| 305 | NT | 0.55 | 0.31 |
| 306 | NT | 0.28 | 0.62 |
| 307 | NT | 0.65 | 0.27 |
| 308 | NT | 0.16 | 0.12 |
| 309 | NT | 0.68 | 0.23 |
| 310 | NT | 0.43 | 0.23 |
| 311 | NT | 0.12 | 0.10 |
| 312 | NT | 0.54 | NT |
| 313 | NT | 0.99 | NT |
| 314 | NT | 0.32 | NT |
| 315 | NT | 1.54 | NT |
| 316 | NT | 0.59 | NT |
| 317 | NT | 0.17 | NT |
| 318 | NT | NT | NT |
| 319 | NT | 0.95 | NT |
| 320 | NT | 0.33 | NT |
| 321 | NT | 1.18 | NT |
| 322 | NT | NT | NT |
| 323 | NT | NT | NT |

TABLE 3

Miles Assay Results

| Example # | Miles Assay dose (mg/kg) | Miles Assay vehicle | Miles Assay % inhibition | Miles Assay Preincubation period (h) | Miles Assay ID$_{50}$ (mg/kg) |
|---|---|---|---|---|---|
| 40 | 75 | PEG400 | 100 | | 18 |
| | 75 | corn oil | 47 | | |
| | 75 | micronized corn oil | 52 | | |
| | 75 | homogenized corn oil | 40 | | |
| | 1 | I.V. bolus in 20% methyl cyclodextrin | 0 | 0.5 | |
| | 1 | I.V. bolus in 20% methyl cyclodextrin | 0 | 1 | |
| | 1 | I.V. bolus in 20% methyl cyclodextrin | 0 | 2 | |
| | 10 | 43% methyl cyclodextrin | 6 | 1 | |
| 156 | 75 | PEG400 (po) | 100 | | |
| 157 | 75 | PEG400 (po) | 38 | | |
| 159 | 75 | PEG400 | 91 | | |
| 167 | 75 | PEG400 | 31 | | |
| 179 | 75 | PEG400 | 65 | | |
| 181 | 75 | PEG400 | 38 | | |
| 206 | 75 | corn oil | 74 | | |
| 207 | 75 | corn oil | 80 | | |
| 208 | 75 | corn oil | 32 | | |
| 209 | 75 | PEG400 | 79 | | |
| | 75 | corn oil | 84 | | |
| 211 | 75 | PEG400 | 38 | | |
| 214 | 75 | PEG400 | 61 | | |
| | 75 | corn oil | 78 | | |
| 215 | 75 | PEG400 | 53 | | |
| 216 | 75 | PEG400 | 91 | | |
| 218 | 75 | PEG400 | 99 | | |
| | 75 | corn oil | 97 | | |
| 219 | 75 | PEG400 | 28 | | |
| 220 | 75 | PEG400 | 39 | | |
| 229 | 75 | PEG400 | 97 | | |
| 231 | 75 | corn oil | 93 | | |
| 234 | 75 | corn oil | 95 | | |
| 235 | 75 | corn oil | 99 | | |
| 238 | 75 | corn oil | 60 | | |
| 239 | 75 | corn oil | 100 | | |
| 243 | 75 | corn oil | 100 | | |
| 247 | 75 | corn oil | 45 | | |
| 249 | 75 | corn oil | 29 | | |
| 250 | 75 | corn oil | 62 | | |
| 266 | 40 | corn oil | 82 | | |
| 271 | 40 | corn oil | 98 | | |

Legend:
PEG = polyethylene glycol
i.v. = intravenous dosage

TABLE 4

CNV Assay results

| Example # | CNV Assay dose (mg/kg) | CNV Assay vehicle | CNV Assay % inhibition | CNV Assay ID$_{50}$ (mg/kg) |
|---|---|---|---|---|
| 40 | 50 (bid) | corn oil | 92 | |
| | 100 (sid) | corn oil | 74 | |
| | 40 (sid) | PEG400 | 96 | ~20 |
| | 100 (sid) | PEG400 | toxic | |
| | 20 (sid) | PEG400 | 54 | |
| | 20 (bid) | PEG400 | 95 | |
| 159 | 100 (sid) | 10% DMAC, 10% NMP, 80% PEG400 | 41 | |
| 209 | 80 (sid) | corn oil | 95 | |
| 214 | 80 (sid) | corn oil | 85 | |

TABLE 4-continued

CNV Assay results

| Example # | CNV Assay dose (mg/kg) | CNV Assay vehicle | CNV Assay % inhibition | CNV Assay ID$_{50}$ (mg/kg) |
|---|---|---|---|---|
| 218 | 80 (sid) | corn oil | 99 | 17 |
|  | 38.5 (sid) | corn oil | 68 |  |
|  | 9.3 (sid) | corn oil | 33 |  |
| 231 | 80 (sid) | corn oil | 85 |  |
| 234 | 80 (sid) | corn oil | 97 | 19 |
|  | 35 (sid) | corn oil | 76 |  |
|  | 8.6 (sid) | corn oil | 18 |  |
| 235 | 40 (sid) | corn oil | 63 |  |
| 239 | 40 (sid) | corn oil | 56 |  |

Legend
sid = once daily dosing;
bid = twice daily dosing;
DMAC = dimethylacetamide;
NMP = N-methyl pyrolidinone;
PEG = polyethylene glycol As shown Table 2, above, the compounds of Examples 1, 5, 6, 7, 12, 15, 17, 21, 29, 31–35, 38, 40, 43, 44, 48–50, 52, 58–60, 65, 72, 73, 82, 87, 88, 90–94, 96, 97, 99, 102, 103, 106, 109–111, 113–117, 119, 122–126, 128–131, 134, 136, 138–147, 149–151, 155–159, 160–189, 191–201, 206–222, 225–268, 270–314, 316, 317, 319 and 320 are preferred as they show either % inhibition of VEGF >79% or VEGF IC$_{50}$<1.0 µM in either the VEGF stimulated Ca$^{++}$ signal assay or KDR assay.

As also can be seen in Table 2, above, the Compounds of Examples 7, 15, 31, 40, 48, 49, 58, 88, 90, 99, 106, 113, 117, 130, 140, 145, 156, 157, 159, 161, 163, 164, 167, 168, 170, 177, 179, 181, 183, 185, 188, 189, 196, 197 and 206–221, 225–235, 238–240, 242–254, 256, 258–260, 262–266, 270–272, 274, 275, 278–301 and 305–311 are more preferred as they show VEGF IC$_{50}$<1.0 µM in both VEGF stimulated Ca$^{++}$ signal assay and KDR assays.

Finally, as shown in Tables 2, 3 and 4, the compounds of Examples 40, 156, 157, 159, 167, 179, 181, 206–209, 211, 214–216, 218–220, 229, 231, 234, 235, 238, 239, 243, 247, 249, 250, 266 and 271 are most preferred in that they show significant in-vivo activity and therefore would be effective in oral administration.

The invention is further illustrated by the following non-limiting examples.

EXAMPLE 1

Phenylaminomethylene-1,3-dihydro-indol-2-one.

2.42 mL of ethylformate are combined with 1.33 gms of 1,3 dihydro-indol-2-one in a solution of 21%, by weight, sodium formate in ethanol. The resulting solution is allowed to stand at room temperature for 30 minutes and then refluxed for 30 minutes to yield a suspension. Once at room temperature the suspension was acidified to pH 1.0 with 10% HCl (aq), then 5 mL of H$_2$O was added. The resulting precipitate is filtered and washed with H$_2$O (4×20 mL) to provide a mixture of E & Z 3-[(hydroxy)-methylene]-1,3-dihydro-indol-2-one, as a solid.

E & Z 3-[(hydroxy)-methylene]-1,3-dihydro-indol-2-one is reacted with 0.022 gms. of aniline by refluxing in tetrahydrofuran (1.2 mL) for 12 hours to yield a quantitative amount (39 mg) of the named compound as a solid following concentration in vacuo, dilution with isopropanol and filtration.

EXAMPLE 2

(3-Bromophenylamino)-methylene]-1,3-dihydro-indol-2-one.

The named compound is prepared by substituting 3-bromoaniline for aniline in the reaction of Example 1.

The compounds of Example 3 through 198, 202–205, 210–213, 219–224, 227–230 and 236–237 are prepared by substituting the appropriate substituted aniline for aniline, or the appropriate 4'-methyl or 5'-fluoro or 5'-chloro or 6' -fluoro or 5'-nitro or 5'-cyano substituted 1,3 dihydro-indol-2-one for 1,3 dihydro-indol-2-one in the reaction of Example 1.

EXAMPLE 179

3-{[4-(4-Pyrrolidin-1-yl-butoxy)-phenylamino]-methylene}-1,3-dihydro-indol-2-one In a manner similar to that described in Example 207, 3-{[4-(4-Iodo-butoxy)-phenylamino]-methylene}-1,3-dihydro-indol-2-one and pyrrolidine are converted to the named compound

EXAMPLE 198

3-{[4-(3-Chloro-propoxy)-phenylamino]-methylene}-1,3-dihydro-indol-2-one

A solution of 3-[(4-hydroxy-phenylamino)-methylene]-1,3-dihydro-indol-2-one (0.945 g, 3.75 mmol) in 20 mL DMF is treated with potassium carbonate (777 mg, 1.5 equiv.) and 1-bromo-3-chloropropane (1.1 equiv.). The reaction mixture is heated to 40° C. for 3 h. The reaction mixture is partitioned between EtOAc and water. The organic layer is collected and washed sequentially with H$_2$O (1×), saturated aqueous NaHCO$_3$ solution (1×), and brine (1×). The organic phase was dried and concentrated to give an oil. The oil was purified by preparative chromatography (silica gel; 1:1 EtOAc:hexane) to give the named compound as a yellow solid (711 mg, 58%).

EXAMPLE 199

3-{[4-(4-Chloro-butoxy)-phenylamino]-methylene}-1,3-dihydro-indol-2-one

A solution of 3-[(4-hydroxy-phenylamino)-methylene]-1,3-dihydro-indol-2-one (0.945 g, 3.75 mmol) in 20 mL DMF is treated with potassium carbonate (777 mg, 1.5 equiv.) and 1-bromo-4-chlorobutane (1.1 equiv.). The reaction mixture is heated to 40° C. for 3 h. The reaction mixture is partitioned between EtOAc and water. The organic layer is collected and washed sequentially with H$_2$O (1 ×), saturated aqueous NaHCO$_3$ solution (1 ×), and brine (1 ×). The organic phase is dried and concentrated to give a solid. The solid is triturated with MeOH and collected by filtration to give the named compound as yellow solid (600 mg, 47%).

EXAMPLE 200

3-{[4-(3-Iodo-propoxy)-phenylamino]-methylene}-1,3-dihydro-indol-2-one

A solution of 3-{[4-(3-Chloro-propoxy)-phenylamino]-methylene}-1,3-dihydro-indol-2-one (45 mg, 0.137 mmol) and NaI (103 mg, 5 equiv.) in 1 mL acetone is heated at 80° C. overnight. The reaction mixture is cooled to room temperature and evaporated to dryness. The residue is dissolved in EtOAc and H$_2$O. The organic layer is collected and dried over anhydrous Na$_2$SO$_4$, filtered, and concentrated to give the named compound as yellow solid (100%).

EXAMPLE 201

3-{[4-(4-Iodo-butoxy)-phenylamino]-methylene}-1,3-dihydro-indol-2-one

In a manner similar to that described for Example 200, 3-{[4-(4-Chloro-butoxy)-phenylamino]-methylene}-1,3-dihydro-indol-2-one was converted to the named compound.

EXAMPLE 206

3-{[4-(4-Morpholin-4-yl-butoxy)-phenylamino]-methylene}-1,3-dihydro-indol-2-one

In a manner similar to that described in Example 207, 3-{[4-(4-Iodo-butoxy)-phenylamino]-methylene}-1,3-dihydro-indol-2-one and morpholine are converted to the named compound.

EXAMPLE 207

3-{[4-(4-Diethylamino-butoxy)-phenylamino]-methylene}-1,3-dihydro-indol-2-one

A 25 mL pressure tube is charged with 3-{[4-(4-Iodo-butoxy)-phenylamino]-methylene}-1,3-dihydro-indol-2-one (75 mg, 0.173 mmol), diethylamine (2 mL) and the reaction mixture is heated at 50° C. for 3 h. The reaction mixture is cooled to room temperature and partitioned between EtOAc and H$_2$O. The organic layer is washed with saturated aqueous NaHCO$_3$ solution, brine, and dried over anhydrous Na$_2$SO$_4$. The organic layer is collected by filtration and concentrated to give a yellow solid. The solid is broken up in MeOH and collected by filtration to give the named compound as a yellow solid.

EXAMPLE 208

3-({4-[4-(4-Methyl-piperazin-1-yl)-butoxy]-phenylamino}-methylene)-1,3-dihydro-indol-2-one In a manner similar to that described in Example 207, 3-{[4-(4-Iodo-butoxy)-phenylamino]-methylene}-1,3-dihydro-indol-2-one and N-methylpiperazine are converted to the named compound.

EXAMPLE 209

3-{[4-(4-Piperidin-1-yl-butoxy)-phenylamino]-methylene}-1,3-dihydro-indol-2-one

In a manner similar to that described in Example 207, 3-{[4-(4-Iodo-butoxy)-phenylamino]-methylene}-1,3-dihydro-indol-2-one and piperidine are converted to the named compound.

EXAMPLE 214

3-{[4-(3-Diethylamino-propoxy)-phenylamino]-methylene}-1,3-dihydro-indol-2-one

In a manner similar to that described in Example 217, 3-{[4-(3-Iodo-propoxy)-phenylamino]-methylene}-1,3-dihydro-indol-2-one and diethylamine are converted to the named compound.

EXAMPLE 215

3-{[4-(3-Morpholin-4-yl-propoxy)-phenylamino]-methylene}-1,3-dihydro-indol-2-one In a manner similar to that described in Example 217, 3-{[4-(3-Iodo-propoxy)-phenylamino]-methylene}-1,3-dihydro-indol-2-one and morpholine are converted to the named compound.

EXAMPLE 216

3-{[4-(3-Pyrrolidin-1-yl-propoxy)-phenylamino]-methylene}-1,3-dihydro-indol-2-one In a manner similar to that described in Example 217, 3-{[4-(3-Iodo-propoxy)-phenylamino]-methylene}-1,3-dihydro-indol-2-one and pyrrolidine are converted to the named compound.

EXAMPLE 217

3-({4-[3-(4-Methyl-piperazin-1-yl)-propoxy]-phenylamino}-methylene)-1,3-dihydro-indol-2-one A solution of 3-{[4-(3-Iodo-propoxy)-phenylamino]-methylene}-1,3-dihydro-indol-2-one (66 mg, 0.157 mmol) in 1 mL THF is treated with 1-methylpiperazine (37.2 μL, 2.2 equiv.) and the resulting reaction mixture is heated at 50° C. for 4 h. The reaction mixture is cooled to room temperature and concentrated under reduced pressure. The residue is partitioned between EtOAc and H$_2$O. The organic layer is collected and washed with saturated aqueous NaHCO$_3$, brine, and dried over anhydrous Na$_2$SO$_4$. The yellow solid residue obtained upon evaporation is broken up in 1:9 EtOAc:hexane and collected by filtration to give the named compound as a yellow solid.

EXAMPLE 218

3-{[4-(3-Piperidin-1-yl-propoxy)-phenylamino]-methylene}-1,3-dihydro-indol-2-one In a manner similar to that described in Example 217, 3-{[4-(3-Iodo-propoxy)-phenylamino]-methylene}-1,3-dihydro-indol-2-one and piperidine are converted to the named compound.

EXAMPLE 225

3-{[4-(3-Thiomorpholin-4-yl-propoxy)-phenylamino]-methylene}-1,3-dihydro-indol-2-one In a manner similar to that described in Example 217, 3-{[4-(3-Iodo-propoxy)-phenylamino]-methylene}-1,3-dihydro-indol-2-one and thiomorpholine are converted to the named compound.

EXAMPLE 226

3-{[4-(4-Thiomorpholin-4-yl-butoxy)-phenylamino]-methylene}-1,3-dihydro-indol-2-one In a manner similar to that described in Example 207, 3-{[4-(4-Iodo-butoxy)-phenylamino]-methylene}-1,3-dihydro-indol-2-one and thiomorpholine are converted to the named compound.

EXAMPLE 231

3-{[4-(3-Diethylamino-propoxy)-phenylamino]-methylene}-4-methyl-1,3-dihydro-indol-2-one To a solution of 4-(3-diethylamino-propoxy)-phenylamine (913 mg, 1.3 equiv.) in THF (14 mL) is added 4-methyl-3-hydroxymethylene-1,3-dihydro-indol-2-one (554 mg, 3.17 mmol) in one portion. The resulting reaction mixture is stirred and heated at 72° C. overnight. The reaction solution is cooled to room temperature and partitioned between EtOAc:H$_2$O. The organic layer is collected and washed with saturated aqueous NaHCO$_3$ and dried over anhydrous Na$_2$SO$_4$. The organic phase is filtered and concentrated. The residue obtained is triturated with 1:4 EtOAc:hexane to give the named compound as a yellow solid (625.8 mg, 52%).

EXAMPLE 231a

Diethyl-[3-(4-nitro-phenoxy)-propyl]-amine

A solution of 3-diethylamino-1-propanol (2.97 mL, 20 mmol) in THF (40 mL) at 0° C. is treated potassium tert-butoxide (2.36 g, 1.05 equiv.) in one portion. The reaction mixture is stirred at 0° C. for 5 min during which time it becomes reddish brown. Neat 1-fluoro-4-nitrobenzene (2.82 g, 1 equiv.) is added dropwise and the ice-bath is removed. The reaction mixture is stirred at room temperature for 15 min. The dark green reaction mixture is quenched with ice-water (300 mL), and extracted with EtOAc (2×200 mL). The combined organic extracts are washed with water (2×300 mL) and brine (1×300 mL) and dried over anhydrous Na$_2$SO$_4$. The oily brown residue obtained after evaporation, is purified by chromatography, (silica gel, 1:4 MeOH:CHCl$_3$) to give the named compound as a brown oil (3.59 g, 71%).

EXAMPLE 231b 4-(3-Diethylamino-propoxy)-phenylamine

A solution of diethyl-[3-(4-nitro-phenoxy)-propyl]-amine (15.2 g, 60.4 mmol) is dissolved in absolute ethanol (350 mL) and to this solution is added hydrazine monohydrate (18 mL, 6 equiv.) followed by the addition of a small portion of Raney nickel. The reaction mixture is heated to 50° C. with stirring for 3 h until all gas evolution has ceased. The reaction mixture is filtered through celite to remove the Raney nickel. The filtrate is concentrated under reduced pressure to give the named compound as a greenish brown oil (quantitative). This material is carried on in subsequent steps without purification.

EXAMPLE 232

5-Chloro-3-{[4-(3-diethylamino-propoxy)-phenylamino]-methylene}-1,3-dihydro-indol-2-one In a manner similar to that described in Example 231, 4-(3-diethylamino-propoxy)-phenylamine (911 mg, 1.3 equiv.) and 5-chloro-3-hydroxymethylene-1,3-dihydro-indol-2-one (617 mg, 3.16 mmol, 1 equiv.) are reacted to give the named compound as a yellow solid (577 mg, 46%).

EXAMPLE 233

3-{[4-(3-Diethylamino-propoxy)-phenylamino]-methylene}-5-fluoro-1,3-dihydro-indol-2-one In a manner similar to that described in Example 231, 4-(3-diethylamino-propoxy)-phenylamine (161 mg, 1.3 equiv.) and 5-fluoro-3-hydroxymethylene-1,3-dihydro-indol-2-one (100 mg, 0.56 mmol, 1 equiv.) are reacted to give the named compound as a yellow solid (88 mg, 41%).

EXAMPLE 234

3-{[4-(3-Diethylamino-propoxy)-phenylamino]-methylene}-6-fluoro-1,3-dihydro-indol-2-one In a manner similar to that described in Example 231, 4-(3-diethylamino-propoxy)-phenylamine (5 g, 1.3 equiv.) and 6-fluoro-3-hydroxymethylene-1,3-dihydro-indol-2-one (3.12 g, 17.4 mmol, 1 equiv.) are reacted to give the named compound as a yellow solid (4.1 g, 61%).

EXAMPLE 235

3-{[4-(2-Morpholin-4-yl-ethylamino)-phenylamino]-methylene}-1,3-dihydro-indol-2-one.

The named compound is prepared by refluxing 1.26 gms. E & Z 3-[(hydroxy)-methylene]-1,3-dihydro-indol-2-one, as prepared in Example 1, with 3.45 gms. of N-(2-morpholin-4-yl-ethyl)-benzene-1,4-diamine in tetrahydrofuran (34.02 mL) for 12 hours. Following concentration in vacuo, dilution with hot isopropanol and filtration provides the named compound is isolated as a yellow solid in the amount of 1.731 gms.

N-(2-Morpholin-4-yl-ethyl)-benzene-1,4-diamine is prepared from p-fluoronitrobenzene by the following method:

A mixture of 7.5 mL of p-fluoronitrobenzene, 10.25 mL 2-morpholin-4-yl-ethylamine and 15 mL N,N-diisopropylamine in 36 mL dioxane is heated at 105° C. for 2 days. The reaction mixture is cooled to room temperature, diluted with dichloromethane (360 mL) and washed with water (3×290 mL). Upon evaporation to dryness, the dichloromethane layer yields the (2-morpholin-4-yl-ethyl)-(4-nitro-phenyl)-amine product, which is recrystallized from methanol.

A suspension of 4.05 gms. of (2-morpholin-4-yl-ethyl)-(4-nitro-phenyl)-amine in 93 mL of ethanol is heated to 50° C. Once dissolution is achieved 4.8 mL hydrazine monohydrate is added to the solution. A Raney nickel 2800 slurry in water (approximately 3.5 mL) is added to the 50° C. solution dropwise, waiting after each addition for the bubbling to cease. Sufficient quantities of Raney nickel have been added when continued addition of Raney nickel causes no further gas evolution. The reaction is then maintained at 50° C. for an additional hour, and subsequently is cooled to room temperature. The reaction mixture is filtered through a pad of celite (rinsing the pad with methanol). The N-(2-morpholin-4-yl-ethyl)-benzene-1,4-diamine (3.45 gms.) is isolated upon evaporation of the filtrate, and is subsequently used without purification in the reaction of Example 235.

Examples 242, 243, 244, and 245 are prepared by substituting the appropriate 4'-methyl or 6'-fluoro or 5'-fluoro or 5'-chloro substituted 1,3-dihydro-indol-2-one for the 1,3-dihydro-indol-2-one and N-(2-morpholin-4-yl-ethyl)-benzene-1,4-diamine, used for the preparation of Example 235, for aniline in the reaction of Example 1.

EXAMPLE 238

4-Methyl-3-{[4-(3-piperidin-1-yl-propoxy)-phenylamino]-methylene}-1,3-dihydro-indol-2-one In a manner similar to that described in Example 231, 4-(3-Piperidin-1-yl-propoxy)-phenylamine (0.61 g, 1.3 equiv.) and 4-methyl-3-hydroxymethylene-1,3-dihydro-indol-2-one (0.35 g, 2 mmol, 1 equiv.) are reacted to give the named compound as a yellow solid (388 mg, 49%).

EXAMPLE 238a

1-[3-(4-Nitro-phenoxy)-propyl]-piperidine

In a manner similar to that described in Example 231a, 3-piperidino-propan-1-ol (1 g) is converted to the named compound as a light brown oil (1.85 g).

EXAMPLE 238b 4-(3-Piperidin-1-yl-propoxy)-phenylamine

In a manner similar to that described in Example 231b, 1-[3-(4-nitro-phenoxy)-propyl]-piperidine (6.99 mmol) is converted to the named compound as a brown oil (1.64 g).

EXAMPLE 239

6-Fluoro-3-{[4-(3-piperidin-1-yl-propoxy)-phenylamino]-methylene}-1,3-dihydro-indol-2-one In a manner similar to that described in Example 231, 4-(3-Piperidin-1-yl-propoxy)-phenylamine (0.61 g, 1.3 equiv.) and 6-fluoro-3-hydroxymethylene-1,3-dihydro-indol-2-one (0.358 g, 2.00 mmol, 1 equiv.) are reacted to give the named compound as a yellow solid (465 mg, 59%).

EXAMPLE 240

5-Fluoro-3-{[4-(3-piperidin-1-yl-propoxy)-phenylamino]-methylene}-1,3-dihydro-indol-2-one In a manner similar to that described in Example 231, 4-(3-piperidin-1-yl-propoxy)-phenylamine (0.57 g, 1.3 equiv.) and 5-fluoro-3-hydroxymethylene-1,3-dihydro-indol-2-one (0.363 g, 2 mmol, 1 equiv.) are reacted to give the named compound as a yellow solid (379 mg, 47%).

EXAMPLE 241

5-Chloro-3-{[4-(3-piperidin-1-yl-propoxy)-phenylamino]-methylene}-1,3-dihydro-indol-2-one In a manner similar to that described in Example 231, 4-(3-piperidin-1-yl-propoxy)-phenylamine (550 mg, 1.3 equiv.) and 5-chloro-3-hydroxymethylene-1,3-dihydro-indol-2-one (380 mg, 2.00 mmol, 1 equiv.) are reacted to give the named compound as a yellow solid (464 mg, 58%).

EXAMPLE 246

4-Methyl-3-{[4-(4-piperidin-1-yl-butoxy)-phenylamino]-methylene}-1,3-dihydro-indol-2-one In a manner similar to that described in Example 231, 4-(4-Piperidin-1-yl-butoxy)-phenylamine (1.19 g, 1.1 equiv.) and 4-methyl-3-hydroxymethylene-1,3-dihydro-indol-2-one (0.79 g, 4.5 mmol, 1 equiv.) are reacted to give the named compound as a yellow solid (0.97 g, 53%).

EXAMPLE 246a

1-[4-(4-Nitro-phenoxy)-butyl]-piperidine

In a manner similar to that described in Example 231a, 4-piperidino-butan-1-ol (36 mmol), is converted to the named compound as a light brown oil (8.61 g, 89%).

EXAMPLE 246b 4-(4-Piperidin-1-yl-butoxy)-phenylamine

In a manner similar to that described in Example 231b, 1-[4-(4-nitro-phenoxy)-butyl]-piperidine (8.12 g, 29 mmol) is converted to the named compound as a light greenish soft solid (6.46 g, 89%).

EXAMPLE 247

6-Fluoro-3-{[4-(4-piperidin-1-yl-butoxy)-phenylamino]-methylene}-1,3-dihydro-indol-2-one In a manner similar to that described in Example 231, 4-(4-piperidin-1-yl-butoxy)-phenylamine (400 mg, 1.1 equiv.) and 6-fluoro-3-hydroxymethylene-1,3-dihydro-indol-2-one (263 mg, 1.47 mmol, 1 equiv.) are reacted to give the named compound as a yellow solid (435 mg, 73%).

EXAMPLE 248

3-{[4-(3-Diethylamino-propoxy)-3-fluoro-phenylamino]-methylene}-1,3-dihydro-indol-2-one In a manner similar to that described in Example 231, 4-(3-Diethylamino-propoxy)-3-fluoro-phenylamine (400 mg, 1.1 equiv.) and 3-hydroxymethylene-1,3-dihydro-indol-2-one (242 mg, 1.5 mmol, 1 equiv.) are reacted to give the named compound as a yellow solid (135 mg, 24%).

EXAMPLE 248a

Diethyl-[3-(2-fluoro-4-nitro-phenoxy)-propyl]-amine

In a manner similar to that described in Example 231a, 3,4-difluoronitrobenzene (6.7 mL, 60.6 mmol, 1 equiv.) and 3-diethylamino-1-propanol (9 mL, 1 equiv.) are converted to the named compound as a brown oil (16.3 g).

EXAMPLE 248b 4-(3-Diethylamino-propoxy)-3-fluoro-phenylamine

In a manner similar to that described in Example 231b, diethyl-[3-(2-fluoro-4-nitro-phenoxy)-propyl]-amine (16.3 g, 60.3 mmol) is converted to the named compound as a brown oil (12.4 g, 86%).

EXAMPLE 249

3-{[4-(3-Diethylamino-propoxy)-3-fluoro-phenylamino]-methylene}-4-methyl-1,3-dihydro-indol-2-one In a manner similar to that described in Example 231, 4-(3-diethylamino-propoxy)-3-fluoro-phenylamine (400 mg, 1.1 equiv.) and 4-methyl-3-hydroxymethylene-1,3-dihydro-indol-2-one (263 mg, 1.5 mmol, 1 equiv.) are reacted to give the named compound as a yellow solid (294 mg, 49%).

EXAMPLE 250

3-{[4-(3-Diethylamino-propoxy)-3-fluoro-phenylamino]-methylene}-6-fluoro-1,3-dihydro-indol-2-one In a manner similar to that described in Example 231, 4-(3-diethylamino-propoxy)-3-fluoro-phenylamine (400 mg, 1.1 equiv.) and 6-fluoro-3-hydroxymethylene-1,3-dihydro-indol-2-one (269 mg, 1.5 mmol, 1 equiv.) are reacted to give the named compound as a yellow solid (195 mg, 32%).

EXAMPLE 251

3-[(4-Piperidin-1-ylmethyl-phenylamino)-methylene]-1,3-dihydro-indol-2-one.

The named compound is prepared by refluxing 0.025 gms. E & Z 3-[(hydroxy)-methylene]-1,3-dihydro-indol-2-one, as prepared in Example 1, with 0.036 gms. 4-piperidin-1-ylmethyl-phenylamine in tetrahydrofuran (1.5 mL) overnight. Following cooling to room temperture, solvent evaporation in vacuo, trituration with isopropanol and filtration the reaction yields the named compound as a solid in the amount of 0.038 gms.

Piperidin-1-ylmethyl-phenylamine is prepared from 4-nitro-benzoic acid by the following method:

A room temperature solution of 5.04 gms. 4-nitro-benzoic acid in tetrahydrofuran (10 mL) is treated with 5.14 gms. 1',1'-carbonyl-diimidizole and immediately immersed in an ice bath. The reaction mixture is stirred in the ice bath for 30 minutes, then it is allowed to warm to room temperature. Once at room temperature the reaction mixture is treated with 3 mL piperidine. The reaction mixture is allowed to stir at room temperature ovenight. The reaction is then made basic with the addition of saturated aqueous sodium bicarbonate solution, and the resulting mixture is extracted with ethyl acetate. The organics are separated, dried over anhydrous sodium sulfate, and subsequently evaporated to dryness in vacuo. The crude product residue is then chromatographed by flash silica gel chromatography using 50% ethyl acetate in hexanes as the eluant. Following evaporation of solvent, 1-(4-nitrobenzoyl)piperidine is isolated as a white solid in the amount of 5.87 gms.

1-(4-Nitrobenzoyl)piperidine (0.1125 gms.) is then dissolved in tetrahydrofuran (1 mL) and slowly added dropwise to a 0° C., 1.0 M solution (4 mL) of Borane in tetrahydrofuran. The reaction mixture is maintained at 0° C. for 20 minutes following the completion of the addition to the Borane/tetrahydrofuran solution. The reaction mixture is then allowed to warm to room temperature, and is subsequently heated to 60° C. using an oil bath. The reaction mixture is maintained at 60° C. overnight, then is cooled to room temperature, and quenched with the addition of concentrated HCl (added until gas evolution stops). The quenched reaction mixture is then extracted with ethyl acetate and water. The organic layer is separated, and concentrated in vacuo, while the aqueous layer is separated and made basic with the addition of aqueous 1M NaOH. The basic aqueous layer is then extracted with ethyl acetate and the ethyl acetate layer from this extraction is concentrated in vacuo. The solids isolated from both concentrated ethyl acetate layers are combined to yield 92 mg of 1-(4-nitrobenzyl)-piperidine as a white-yellow solid.

1-(4-Nitro-benzyl)-piperidine (0.5052 gms.) is suspended in 25 mL of a 1:1 (v:v) solution of acetic acid and water. The suspension is then treated with 45 mL of an ~10 wt. % solution of $TiCl_3$ in 20–30 wt. % HCl, dropwise. Over the course of the addition a color change from colorless to purple to black ensues. The reaction mixture is immersed in a 60° C. oil bath overnight following the addition of $TiCi_3$. The reaction mixture is then cooled to room temperature and made basic with the addition of a 10% aqueous solution of NaOH. The basic reaction mixture is extracted with chloroform, and the organic layer is dried over anhydrous sodium sulfate. Following evaporation of the solvent the organic layer yields 0.333 gms. of piperidin-1-ylmethyl-phenylamine.

EXAMPLE 252

4-Methyl-3-{[4-(2-piperidin-1-yl-ethoxy)-phenylamino]-methylene}-1,3-dihydro-indol-2-one In a manner similar to that described in Example 231, 4-(2-piperidin-1-yl-ethoxy)-phenylamine (754 mg, 1.2 equiv.) and 4-methyl-3-hydroxymethylene-1,3-dihydro-indol-2-one (500 mg, 2.86 mmol, 1 equiv.) are reacted to give the named compound as a yellow solid (530 mg, 49%).

EXAMPLE 252a

1-[2-(4-Nitro-phenoxy)-ethyl]-piperidine

In a manner similar to that described in Example 231a, 1-piperidine-ethanol (8.8 mL, 66 mmol, 1.1 equiv.) is converted to the named compound as a light brown solid (14.6 g, 97%).

EXAMPLE 252b 4-(2-Piperidin-1-yl-ethoxy)-phenylamine

In a manner similar to that described in Example 231b, 1-[2-(4-nitro-phenoxy)-ethyl]-piperidine (5.0 g, 20 mmol) is converted to the named compound as a light brown oil (4.4 g).

EXAMPLE 253

6-Fluoro-3-{[4-(2-piperidin-1-yl-ethoxy)-phenylamino]-methylene}-1,3-dihydro-indol-2-one In a manner similar to that described in Example 231, 4-(2-piperidin-1-yl-ethoxy)-phenylamine (737 mg, 1.2 equiv.) and 6-fluoro-3-hydroxymethylene-1,3-dihydro-indol-2-one (500 mg, 2.79 mmol, 1 equiv.) are reacted to give the named compound as a yellow solid (745 mg, 70%).

EXAMPLE 254

3-{[4-(2-Piperidin-1-yl-ethoxy)-phenylamino]-methylene}-1,3-dihydro-indol-2-one

In a manner similar to that described in Example 231, 4-(2-piperidin-1-yl-ethoxy)-phenylamine (820 mg, 1.2 equiv.) and 3-hydroxymethylene-1,3-dihydro-indol-2-one (500 mg, 3.11 mmol, 1 equiv.) are reacted to give the named compound as a yellow solid (899 mg, 80%).

EXAMPLE 255

4-Fluoro-3-{[4-(3-piperidin-1-yl-propoxy)-phenylamino]-methylene}-1,3-dihydro-indol-2-one In a manner similar to that described in Example 231, 4-(3-piperidin-1-yl-propoxy)-phenylamine (610 mg, 1.3 equiv.) and 4-fluoro-3-hydroxymethylene-1,3-dihydro-indol-2-one (360 mg, 2 mmol, 1 equiv.) are converted to the named compound as a yellow solid (625 mg, 79%).

EXAMPLE 256

4-Methyl-3-[(4-piperidin-1-ylmethyl-phenylamino)-methylene]-1,3-dihydro-indol-2-one.

The named compound is prepared by refluxing 0.045 gms E & Z-3-hydroxymethylene-4-methyl-1,3-dihydro-indol-2-one, prepared by substituting 4'-methyl-1,3 dihydro-indol-2-one for 1,3 dihydro-indol-2-one in the reaction of Example 1, with 0.064 gms. 4-piperidin-1-ylmethyl-phenylamine, prepared as in the reaction of Example 251, in tetrahydrofuran (1 mL) overnight. Following cooling to room temperature, solvent evaporation in vacuo, trituration with isopropanol and filtration the reaction yields the named compound as a solid in the amount of 0.0463 gms.

Examples 257–260 are prepared by substituting the appropriate 4'-fluoro or 5'-fluoro or 6'-fluoro or 5'-chloro substituted 1,3-dihydro-indol-2-one for the 1,3-dihydro-indol-2-one and 4-piperidin-1-ylmethyl-phenylamine (used in the preparation of Example 251) for aniline in the reaction of Example 1.

EXAMPLE 261

4-Fluoro-3-{[4-(2-piperidin-1-yl-ethoxy)-phenylamino]-methylene}-1,3-dihydro-indol-2-one In a manner similar to that described in Example 231, 4-(2-piperidin-1-yl-ethoxy)-phenylamine (600 mg, 1.2 equiv.) and 4-fluoro-3-hydroxymethylene-1,3 -dihydro-indol-2-one (407 mg, 2.27 mmol, 1 equiv.) (4-Fluorooxindole may be prepared as described in Synthesis 1991, 10, 871) are reacted to give the named compound as a yellow solid (542 mg, 63%).

EXAMPLE 262

5-Chloro-3-{[4-(2-piperidin-1-yl-ethoxy)-phenylamino]-methylene}-1,3-dihydro-indol-2-one In a manner similar to that described in Example 231, 4-(2-piperidin-1-yl-ethoxy)-phenylamine (600 mg, 1.2 equiv.) and 5-chloro-3-hydroxymethylene-1,3-dihydro-indol-2-one (444 mg, 2.27 mmol, 1 equiv.) are reacted to give the named compound as a yellow solid (513 mg, 57%).

EXAMPLE 263

5-Fluoro-3-{[4-(2-piperidin-1-yl-ethoxy)-phenylamino]-methylene}-1,3-dihydro-indol-2-one In a manner similar to that described in Example 231, 4-(2-piperidin-1-yl-ethoxy)-phenylamine (600 mg, 1.2 equiv.) and 5-fluoro-3-hydroxymethylene-1,3-dihydro-indol-2-one (407 mg, 2.27 mmol, 1 equiv.) are reacted to give the named compound as a yellow solid (644 mg, 74%).

EXAMPLE 264

3-{[4-(2-Diethylamino-ethoxy)-phenylamino]-methylene}-4-methyl-1,3-dihydro-indol-2-one In a manner similar to that describe in Example 231, 4-(2-diethylamino-ethoxy)-phenylamine (713 mg, 1.2 equiv.) and 4-methyl-3-hydroxymethylene-1,3-dihydro-indol-2-one (500 mg, 2.86 mmol, 1 equiv.) are reacted to give the named compound as a yellow solid (237 mg, 23%).

EXAMPLE 264a

Diethyl-[2-(4-nitro-phenoxy)-ethyl]-amine

In a manner similar to that described in Example 231a, N,N-diethylethanolamine (8.75 mL, 66 mmol, 1.1 equiv.) is converted to the named compound as a brown oil (14.3 g).

EXAMPLE 264b 4-(2-Diethylamino-ethoxy)-phenylamine

In a manner similar to that described in Example 231b, diethyl-[2-(4-nitro-phenoxy)-ethyl]-amine (4.77 g, 20 mmol) is converted to the named compound as a brown oil (4.16 g).

EXAMPLE 265

3-{[4-(2-Diethylamino-ethoxy)-phenylamino]-methylene}-1,3-dihydro-indol-2-one

In a manner similar to that described in Example 231, 4-(2-diethylamino-ethoxy)-phenylamine (775 mg, 1.2 equiv.) and 3-hydroxymethylene-1,3-dihydro-indol-2-one (500 mg, 3.11 mmol, 1 equiv.) are reacted to give the named compound as a yellow solid (557 mg, 51%).

EXAMPLE 266

3-{[4-(2-Diethylamino-ethoxy)-phenylamino]-methylene}-6-fluoro-1,3-dihydro-indol-2-one In a manner similar to that described in Example 231, 4-(2-Diethylamino-ethoxy)-phenylamine (697 mg, 1.2 equiv.) and 6-fluoro-3-hydroxymethylene-1,3-dihydro-indol-2-one (500 mg, 2.79 mmol, 1 equiv.) are reacted to give the named compound as a yellow solid (399 mg, 39%).

EXAMPLE 267

3-{[4-(3-Diethylamino-propoxy)-3-fluoro-phenylamino]-methylene}-4-fluoro-1,3-dihydro-indol-2-one In a manner similar to that described in Example 231, 4-(3-Diethylamino-propoxy)-3-fluoro-phenylamine (720 mg, 1.5 equiv.) and 4-fluoro-3-hydroxymethylene-1,3-dihydro-indol-2-one (358 mg, 2.00 mmol) are reacted to give the named compound as a yellow solid (541 mg, 67%).

EXAMPLE 268

6-(3-Methoxy-phenyl)-3-{[4-(4-methyl-piperazin-1-yl)-phenylamino]-methylene}-1,3-dihydro-indol-2-one The named compound is prepared by refluxing 0.020 gms E & Z 3-hydroxymethylene-6-(3-methoxy-phenyl)-1,3-dihydro-indol-2-one with 0.021 gms 4-(4-methyl-piperazin-1-yl)-phenylamine in tetrahydrofuran (0.33 mL) for 2 days. Following cooling to room temperature, solvent evaporation in vacuo, trituration with isopropanol (plus a little chloroform) and filtration the reaction yields the named compound as a solid in the amount of 16.2 mg.

E & Z 3-Hydroxymethylene-6-(3-methoxy-phenyl)-1,3-dihydro-indol-2-one is prepared in 5 steps from 4-Bromo-1-fluoro-2-nitro-benzene by the following method:

4-Bromo-1-fluoro-2-nitro-benzene (5 gms.), 3.85 gms. 3-methoxyphenylboronic acid and 22 mL of a 2M aqueous solution of sodium carbonate are suspended in 100 mL of a 1:1 (v:v) mix of toluene and ethanol. The resulting suspension is then treated with 0.8 gms. tetrakis(triphenylphosphine)palladium (0) at room temperature. The reaction mixture is then heated at reflux for 12 h. The reaction mixture is subsequently concentrated in vacuo, and the resulting residue is taken up in ethyl acetate (200 mL). The ethyl acetate solution is then washed successively with water (2×200 mL), and brine (2×200 mL). The organic layer is then dried by filtering through phase separator paper and concentrated in vacuo to yield 7.19 gms. of crude product. The crude product is then recrystallized from hot ethanol yielding 4-fluoro-3'-methoxy-3-nitro-biphenyl as a yellow-white solid in the amount of 4.767 gms.

A room temperature DMSO (50 mL) suspension of a 60% dispersion of sodium hydride in mineral oil (3.94 gms.) is treated dropwise with 10.41 mL of dimethylmalonate. The suspension is then heated to 100° C. for 35 minutes and subsequently treated with a solution of 4-fluoro-3'-methoxy-3-nitro-biphenyl (4.6138 gms.) in DMSO (55 mL). The reaction mixture is heated at 100° C. for an additional 1 h after which it is cooled to room temperature, and quenched with the addition of a saturated aqueous solution of ammonium chloride (300 mL). The quenched reaction mixture is then extracted with ethyl acetate (3×300 mL). The combined ethyl acetate washes are then washed with brine (1×500 mL), filtered through phase separator paper to dry the solution, and then concentrated in vacuo. The crude residue isolated is recrystallized from isopropanol/ethyl acetate yielding 2-(3'-methoxy-3-nitro-biphenyl-4-yl)-malonic acid dimethyl ester in the amount of 4.4023 gms.

2-(3'-Methoxy-3-nitro-biphenyl-4-yl)-malonic acid dimethyl ester (4.4023 gms.) is suspended in 45 mL of 6N HCl and heated at 110° C. for 4 days. The reaction mixture is cooled to room temperature and the precipitate is collected by filtration. As the solid material is in rather large chunks, the solid purification is simplified by first dissolving the solid chunks in an excess of hot methanol, and subsequently concentrating the solution in vacuo to get a more manageable powder. This powder is then triturated with approximately 10 mL of methanol and filtered yielding (3'-methoxy-3-nitro-biphenyl-4-yl)-acetic acid in the amount of 2.0120 gms.

A solution of (3'-Methoxy-3-nitro-biphenyl-4-yl)-acetic acid (2.0120 gms.) in 35 mL methanol is treated with 0.3123 gms. of 10% palladium on carbon. The resulting suspension is then stirred vigorously under an atmosphere of hydrogen at room temperature and atmospheric pressure for 3 h. The reaction mixture is then filtered through a pad of celite, the filtrate is treated with decolorizing charcoal and filtered a second time through celite. The filtrate is then concentrated in vacuo and purified by trituration with isopropanol yielding 0.5736 gms. of 6-(3-methoxy-phenyl)-1,3-dihydro-indol-2-one.

6-(3-Methoxy-phenyl)-1,3-dihydro-indol-2-one (0.2282 gms.) is combined with 0.23 mL of ethylformate in 0.67 mL anhydrous ethanol, and is treated with a solution of 21%, by weight, sodium formate in ethanol (0.40 mL). The resulting solution is allowed to stand at room temperature for 30 minutes, and then is refluxed for 2 h to yield a suspension. Once at room temperature the suspension is acidified to pH 1.0 with 10% HCl (aq), then diluted with 5 mL of H$_2$O. The resulting precipitate was filtered and washed with H$_2$O (4×20 mL) to provide a mixture of E & Z 3-hydroxymethylene-6-(3-methoxy-phenyl)-1,3-dihydro-indol-2-one, as a solid in the amount of 0.2064 gms.

EXAMPLE 269

6-(3-Methoxy-phenyl)-3-{[4-morpholin-4-yl-phenylamino)-methylene]-1,3-dihydro-indol-2-one.

The named compound is prepared by refluxing 0.020 gms E & Z 3-hydroxymethylene-6-(3-methoxy-phenyl)-1,3-dihydro-indol-2-one with 0.020 gms. 4-morpholin-4-yl-phenylamine in tetrahydrofuran (0.33 mL) for 2 days. Following cooling to room temperature, solvent evaporation in vacuo, trituration with isopropanol and filtration the reaction yields the named compound as a solid in the amount of 15.7 mg.

EXAMPLE 270

4-Methyl-3-{[4-(2-pyrrolidin-1-yl-ethoxy)-phenylamino]-methylene}-1,3-dihydro-indol-2-one In a manner similar to that described in Example 231, (706 mg, 1.2 equiv.) and 4-methyl-3-hydroxymethylene-1,3-dihydro-indol-2-one (500 mg, 2.86 mmol, 1 equiv.) are reacted to give the named compound as a yellow solid (478 mg, 46%).

EXAMPLE 270a

1-[2-(4-Nitro-phenoxy)-ethyl]-pyrrolidine

In a manner similar to that described in Example 231a, 1-(2-hydroxyethyl)-pyrroline (7.72 mL, 66 mmol, 1.1 equiv.) is converted to the named compound as a brown oil (14.2 g).

EXAMPLE 270b 4-(2-Pyrrolidin-1-yl-ethoxy)-phenylamine

In a manner similar to that described in Example 23 1b, 1-[2-(4-nitro-phenoxy)-ethyl]-pyrrolidine (7.5 g, 30 mmol) is converted to the named compound as a reddish oil (5.52 g, 89%).

EXAMPLE 271

6-Fluoro-3-{[4-(2-pyrrolidin-1-yl-ethoxy)-phenylamino]-methylene}-1,3-dihydro-indol-2-one In a manner similar to that described in Example 231, 4-(2-pyrrolidin-1-yl-ethoxy)-phenylamine (690 mg, 1.2 equiv.) and 6-fluoro-3-hydroxymethylene-1,3-dihydro-indol-2-one (500 mg, 2.79 mmol, 1 equiv.) are reacted to give the named compound as a yellow solid (500 mg, 48%).

EXAMPLE 272

3-{[4-(2-Pyrrolidin-1-yl-ethoxy)-phenylamino]-methylene}-1,3-dihydro-indol-2one

In a manner similar to that described in Example 231, 4-(2-pyrrolidin-1-yl-ethoxy)-phenylamine (767 mg, 1.2 equiv.) and 3-hydroxymethylene-1,3-dihydro-indol-2-one (500 mg, 3.11 mmol, 1 equiv.) are reacted to give the named compound as a yellow solid (690 mg, 64%).

EXAMPLE 273

4-Fluoro-3-{[4-(2-pyrrolidin-1-yl-ethoxy)-phenylamino]-methylene}-1,3-dihydro-indol-2-one In a manner similar to that described in Example 231, 4-(2-pyrrolidin-1-yl-ethoxy)-phenylamine (690 mg, 1.2 equiv.) and 4-fluoro-3-hydroxymethylene-1,3-dihydro-indol-2-one (500 mg, 2.79 mmol, 1 equiv.) to give the named compound as a yellow solid (790 mg, 77.0%).

EXAMPLE 274

5-Fluoro-3-{[4-(2-pyrrolidin-1-yl-ethoxy)-phenylamino]-methylene}-1,3-dihydro-indol-2-one In a manner similar to that described in Example 231, 4-(2-Pyrrolidin-1-yl-ethoxy)-phenylamine (690 mg, 1.2 equiv.) and 5-fluoro-3-hydroxymethylene-1,3-dihydro-indol-2-one (500 mg, 2.79 mmol, 1 equiv.) are reacted to give the named compound as a yellow solid (705 mg, 69%).

EXAMPLE 275

5-Chloro-3-{[4-(2-pyrrolidin-1-yl-ethoxy)-phenylamino]-methylene}-1,3-dihydro-indol-2-one In a manner similar to that described in Example 231, 4-(2-Pyrrolidin-1-yl-ethoxy)-phenylamine (632 mg, 1.2 equiv.) and 5-chloro-3-hydroxymethylene-1,3-dihydro-indol-2-one (500 mg, 2.56 mmol, 1 equiv.) are reacted to give the named compound as a yellow solid (775 mg, 79%).

EXAMPLE 276

6-(3-Methoxy-phenyl)-3-{[4-(3-piperidin-1-yl-propoxy)-phenylamino]-methylene}-1,3-dihydro-indol-2-one.

The named compound is prepared by refluxing 0.020 gms E & Z 3-hydroxymethylene-6-(3-methoxy-phenyl)-1,3-dihydro-indol-2-one (see example 268) with 0.0375 gms 4-(3-piperidin-1-yl-propoxy)-phenylamine (used in the preparation of Example 218) in tetrahydrofuran (0.33 mL) for 36 h. Following cooling to room temperature, solvent evaporation in vacuo, trituration with isopropanol and filtration the reaction yields the named compound as a solid in the amount of 16.8 mg.

EXAMPLE 277

3-{[4-(3-Diethylamino-propoxy)-phenylamino]-methylene}-6-(3-Methoxy-phenyl)-1,3-dihydro-indol-2-one.

The named compound is prepared by refluxing 0.020 gms E & Z 3-Hydroxymethylene-6-(3-methoxy-phenyl)-1,3-dihydro-indol-2-one (see example 268) with 0.0327 gms 4-(3-diethylamino-propoxy)-phenylamine (used in the preparation of Example 214) in tetrahydrofuran (0.33 mL) for 36 h. Following cooling to room temperature, solvent evaporation in vacuo, trituration with ethyl acetate/(min) hexanes and filtration the reaction yields the named compound as a solid in the amount of 9.0 mg.

EXAMPLE 278

4-Methyl-3-{[4-(1-methyl-piperidin-3-ylmethoxy)-phenylamino]-methylene}-1,3-dihydro-indol-2-one In a manner similar to that described in Example 231, 4-(1-methyl-piperidin-3-ylmethoxy)-phenylamine (603 mg, 1.2 equiv.) and 4-methyl-3-hydroxymethylene-1,3-dihydro-indol-2-one (400 mg, 2.28 mmol, 1 equiv.) are reacted to give the named compound as a yellow solid (439 mg, 51%).

EXAMPLE 278a

1-Methyl-3-(4-nitro-phenoxymethyl)-piperidine

In a manner similar to that described in Example 231a, 1-methyl-3-piperidinemethanol (8.53 g, 66 mmol, 1.1 equiv.) is converted to the named compound as a brown oil (11.5 g, 77%).

EXAMPLE 278b 4-(1-Methyl-piperidin-3-ylmethoxy)-phenylamine

In a manner similar to that described in Example 231b, 1-Methyl-3-(4-nitro-phenoxymethyl)-piperidine (7.5 g, 30 mmol) is converted to the named compound as a light brown solid (4.82 g, 73%).

EXAMPLE 279

6-Fluoro-3-{[4-(1-methyl-piperidin-3-ylmethoxy)-phenylamino]-methylene}-1,3-dihydro-indol-2-one In a manner similar to that described in Example 231, 4-(1-methyl-piperidin-3-ylmethoxy)-phenylamine (590 mg, 1.2 equiv.) and 6-fluoro-3-hydroxymethylene-1,3-dihydro-indol-2-one (400 mg, 2.23 mmol, 1 equiv.) are reacted to give the named compound as a yellow solid (466 mg, 55%).

EXAMPLE 280

3-{[4-(1-Methyl-piperidin-3-ylmethoxy)-phenylamino]-methylene}-1,3-dihydro-indol-2-one In a manner similar to that described in Example 231, 4-(1-methyl-piperidin-3-ylmethoxy)-phenylamine (656 mg, 1.2 equiv.) and 3-hydroxymethylene-1,3-dihydro-indol-2-one (400 mg, 2.48 mmol, 1 equiv.) are reacted to give the named compound as a yellow solid (732 mg, 81%).

EXAMPLE 281

4-Fluoro-3-{[4-(1-methyl-piperidin-3-ylmethoxy)-phenylamino]-methylene}-1,3-dihydro-indol-2-one In a manner similar to that described in Example 231, 4-(1-methyl-piperidin-3-ylmethoxy)-phenylamine (590 mg, 1.2 equiv.) and 4-fluoro-3-hydroxymethylene-1,3-dihydro-indol-2-one (400 mg, 2.23 mmol, 1 equiv.) are reacted to give the named compound as a yellow solid (576 mg, 68%).

EXAMPLE 282

5-Fluoro-3-{[4-(1-methyl-piperidin-3-ylmethoxy)-phenylamino]-methylene}-1,3-dihydro-indol-2-one In a manner similar to that described in Example 231, 4-(1-methyl-piperidin-3-ylmethoxy)-phenylamine hydrochloride (688 mg, 1.2 equiv.) and 5-fluoro-3-hydroxymethylene-1,3-dihydro-indol-2-one (400 mg, 2.23 mmol, 1 equiv.) with the addition of anhydrous $Et_3N$ (2.25 equiv.) are reacted to give the named compound as a yellow solid (657 mg, 77%).

EXAMPLE 283

5-Chloro-3-{[4-(1-methyl-piperidin-3-ylmethoxy)-phenylamino]-methylene}-1,3-dihydro-indol-2-one In a manner similar to that described in Example 231, 4-(1-methyl-piperidin-3-ylmethoxy)-phenylamine hydrochloride (158 mg, 1.2 equiv.) and 5-chloro-3-hydroxymethylene-1,3-dihydro-indol-2-one (100 mg, 0.51 mmol, 1 equiv.) with the addition of anhydrous $Et_3N$ (2.11 equiv.) are reacted to give the named compound as a yellow solid (100 mg, 49%).

EXAMPLE 284

3-{[4-(2-Piperidin-1-yl-ethyl)-phenylamino]-methylene}-1,3-dihydro-indol-2-one

The named compound is prepared by refluxing 0.0505 gms. E & Z 3-[(hydroxy)-methylene]-1,3-dihydro-indol-2-one, as prepared in Example 1, with 0.085 gms. 4-(2-piperidin-1-yl-ethyl)-phenylamine in tetrahydrofuran (1.0 mL) overnight. Following cooling to room temperture, solvent evaporation in vacuo, trituration with isopropanol and filtration the reaction yields the named compound in the amount of 66 mg.

4-(2-Piperidin-1-yl-ethyl)-phenylamine is prepared from (4-Nitro-phenyl)-acetic acid by the following method:

A room temperature solution of 2.53 gms. (4-Nitrophenyl)-acetic acid in tetrahydrofuran (10 mL) is treated with 2.44 gms. 1',1'-carbonyl-diimidizole and immediately immersed in an ice bath. The reaction mixture is stirred in the ice bath for 30 minutes then it is allowed to warm to room temperature. Once at room temperature the reaction mixture is treated with 1.21 mL piperidine, and then is stirred overnight at room temperature. The reaction is then made basic with the addition of saturated aqueous sodium bicarbonate, and the resulting mixture is extracted with ethyl acetate. The organics are separated, dried over anhydrous sodium sulfate, filtered, and subsequently evaporated to dryness in vacuo. The crude product residue is then chromatographed by flash silica gel chromatography using 50% ethyl acetate in hexanes as the eluant. Following evaporation of solvent, 2-(4-nitro-phenyl)-1-piperidin-1-yl-ethanone is isolated as a white solid in the amount of 3.18 gms. 2-(4-Nitro-phenyl)-1-piperidin-1-yl-ethanone (1.24 gms.) is then dissolved in tetrahydrofuran (5 mL), and slowly added dropwise to a 0° C., 1.0M solution (35 mL) of Borane in tetrahydrofuran. The reaction mixture is maintained at 0° C. for 20 minutes following the completion of the addition to the Borane/tetrahydrofuran solution. The reaction mixture is then allowed to warm to room temperature, and is subsequently refluxed using an oil bath. The reaction mixture is maintained at refluxing temperature overnight, then cooled to 0° C. and quenched with the addition of concentrated HCl (added until fizzing stops). The quenched reaction mixture is then extracted with ethyl acetate and water. The organic layer is then separated, dried over sodium sulfate and concentrated in vacuo. The solid isolated is then triturated with hexanes and a little ethyl acetate to yield 0.7563 gms. of 1-[2-(4-nitro-phenyl)-ethyl]-piperidine as a white solid following filtration.

1-[2-(4-Nitro-phenyl)-ethyl]-piperidine (0.1178 gms.) is suspended in 4.5 mL of a 1:1 (v:v) solution of acetic acid and water. The suspension is then immersed in a 65° C. oil bath and treated in dropwise fashion with 9 mL of an ~10 wt. % solution of $TiCl_3$ in 20–30 wt. % HCl. Over the course of the addition a color change from colorless to purple to black ensues. The reaction mixture is maintained in the 65° C. oil bath overnight following the addition of $TiCl_3$. The reaction mixture is then cooled to 0° C., and made basic with the addition of a 10% aqueous solution of NaOH. The basic reaction mixture is then extracted with chloroform. The emmulsion that forms is filtered through glass wool, re-extracted with chloroform, and then dried over anhydrous sodium sulfate. Following evaporation of the solvent the residue is chromatographed by flash silica gel chromatography (10% methanol in chloroform) to yield 60 mg of 4-(2-piperidin-1-yl-ethyl)-phenylamine.

EXAMPLE 286

4-Methyl-3-{[4-(2-piperidin-1-yl-ethyl)-phenylamino]-methylene}-1,3-dihydro-indol-2-one The named compound is prepared by refluxing 0.055 gms. E & Z-3-Hydroxymethylene-4-methyl-1,3-dihydro-indol-2-one, as prepared in the reaction of Example 1, with 0.085 gms. 4-(2-piperidin-1-yl-ethyl)-phenylamine (used in the preparation of Example 284) in tetrahydrofuran (1 mL) overnight. Following cooling to room temperture, solvent evaporation in vacuo, trituration with isopropanol and filtration the reaction yields the named compound as a solid in the amount of 38 mg.

Examples 285 and 287–289 are prepared by substituting the appropriate 5'-chloro or 4'-fluoro or 5'-fluoro or 6'-fluoro substituted 1,3-dihydro-indol-2-one for the 1,3-dihydro-indol-2-one and 4-(2-piperidin-1-yl-ethyl)-phenylamine (used in the preparation of Example 284) for aniline in the reaction of Example 1.

EXAMPLE 290

3-[(4-Morpholin-4-ylmethyl-phenylamino)-methylene]-1,3-dihydro-indol-2-one

The named compound is prepared by refluxing 0.051 gms. E & Z 3-[(hydroxy)-methylene]-1,3-dihydro-indol-2-one, as prepared in Example 1, with 0.085 gms. 4-morpholin-4-ylmethyl-phenylamine in tetrahydrofuran (2.0 mL) overnight. Following cooling to room temperture, solvent evaporation in vacuo, trituration with isopropanol and filtration the reaction yields the named compound as a solid in the amount of 0.070 gms.

4-Morpholin-4-ylmethyl-phenylamine is prepared from 4-Nitro-benzoic acid by the following method:

A room temperature solution of 2.49 gms. 4-nitro-benzoic acid in tetrahydrofuran (15 mL) is treated with 2.44 gms. 1',1'-carbonyl-diimidizole, and immediately immersed in an ice bath. The reaction mixture is stirred in the ice bath for 30 minutes then it is allowed to warm to room temperature. Once at room temperature the reaction mixture is treated with 1.5 mL piperidine. The reaction mixture is allowed to stir at room temperature ovenight. The reaction is then made basic with the addition of saturated aqueous sodium bicarbonate solution, and the resulting mixture is extracted with ethyl acetate. The organics are separated, dried over anhydrous sodium sulfate and subsequently evaporated to dryness in vacuo. The crude product residue is then chromatographed by flash silica gel chromatography using 50% ethyl acetate in hexanes as the eluant. Following evaporation of solvent, 1-(4-nitrobenzoyl)morpholine is isolated as a white solid in the amount of 1.679 gms.

1-(4-Nitrobenzoyl)morpholine (1.1219 gms.) is then dissolved in tetrahydrofuran (6 mL) and slowly added dropwise to a 0° C., 1.0M solution (30 mL) of Borane in tetrahydrofuran. The reaction mixture is maintained at 0° C. for 20 minutes following the completion of the addition to the Borane/tetrahydrofuran solution. The reaction mixture is then allowed to warm to room temperature, and is subsequently heated to reflux using an oil bath. The reaction mixture is maintained at refluxing temperature overnight, then cooled to room temperature and quenched with the addition of concentrated HCl (added until gas evolution stops). The quenched reaction mixture is then extracted with ethyl acetate and water. The organic layer is then separated and concentrated in vacuo to yield 0.6650 gms. of 1-(4-nitro-benzyl)-morpholine as a yellow solid.

1-(4-Nitro-benzyl)-morpholine (0.6446 gms.) is suspended in 15 mL of a 1:1 (v:v) solution of acetic acid and water. The suspension is then heated with a heat gun until a homogeneous solution forms. The solution is then treated with 35 mL of an ~10 wt. % solution of $TiCl_3$ in 20–30 wt. % HCl, dropwise. Over the course of the addition a color change from colorless to purple to black ensues. The reaction mixture is immersed in a 60° C. oil bath overnight following the addition of $TiCl_3$. The reaction mixture is then cooled to room temperature and made basic with the addition of a 10% aqueous solution of NaOH. The basic reaction mixture is then extracted with chloroform four times and the combined organic layers are dried over anhydrous sodium sulfate. Following filtration and evaporation of the solvent in vacuo, the organic layer yields 0.5112 gms. 4-morpholin-4-ylmethyl-phenylamine.

EXAMPLE 292

4-Methyl-3-[(4-morpholin-4-ylmethyl-phenylamino)-methylene]-1,3-dihydro-indol-2-one The named compound is prepared by refluxing 0.056 gms E & Z-3-hydroxymethylene-4-methyl-1,3-dihydro-indol-2-one, prepared by substituting 4'-methyl-1,3 dihydro-indol-2-one for 1,3 dihydro-indol-2-one in the reaction of Example 1, with 0.085 gms. 4-morpholin-4-ylmethyl-phenylamine, prepared as in the reaction of Example 290, in tetrahydrofuran (2.0 mL) overnight. Following cooling to room temperature, solvent evaporation in vacuo, trituration with isopropanol, and filtration the reaction yields the named compound as a solid in the amount of 12 mg.

Examples 291, and 293–295 are prepared by substituting the appropriate 5'-chloro or 4'-fluoro or 5'-fluoro or 6'-fluoro substituted 1,3-dihydro-indol-2-one for the 1,3-dihydro-indol-2-one and 4-morpholin-4-ylmethyl-phenylamine, used in the preparation of Example 290, for aniline in the reaction of Example 1.

EXAMPLE 296

4-Methyl-3-{[4-(3-morpholin-4-yl-propylamino)-phenylamino]-methylene}-1,3-dihydro-indol-2-one The named compound is prepared by substituting 4-methyl-1,3-dihydro-indol-2-one for the 1,3-dihydro-indol-2-one and N-(3-morpholin-4-yl-propyl)-benzene-1,4-diamine (used for the preparation of Example 290) for aniline in the reaction of Example 1.

EXAMPLE 297

3-{[4-(3-Morpholin-4-yl-propylamino)-phenylamino]-methylene}-1,3-dihydroindol-2-one The named compound is prepared by refluxing 0.336 gms. E & Z 3-[(hydroxy)-methylene]-1,3-dihydro-indol-2-one, as prepared in Example 1, with 0.730 gms. N-(3-morpholin-4-yl-propyl)-benzene-1,4-diamine in tetrahydrofuran (12.5 mL) for 24 hours to yield the named compound as a solid in the amount of 0.513 gms. following concentration in vacuo, recrystallization with hot isopropanol and filtration.

N-(3-Morpholin-4-yl-propyl)-benzene-1,4-diamine is prepared from p-fluoronitrobenzene by the following method:

A mixture of 4.85 mL of p-fluoronitrobenzene, 6.0 gms. 2-morpholin-4-yl-ethylamine and 8.69 mL N,N-diisopropylamine in 20.8 mL dioxane is heated at 105° C. for 2 days. The reaction mixture is cooled to room temperature, evaporated to dryness, and recrystallized from hot isopropanol yielding the (3-morpholin-4-yl-propyl)-(4-nitro-phenyl)-amine product in the amount of 5.30 gms.

A suspension of 5.00 gms. of (3-morpholin-4-yl-propyl)-(4-nitro-phenyl)-amine in 110 mL of ethanol is heated to 50° C. Once dissolution is achieved 5.49 mL hydrazine monohydrate is added to the solution. A Raney nickel slurry in water is added to the 50° C. solution dropwise, waiting after each addition for the bubbling to cease. Sufficient quantities of Raney nickel have been added when continued addition of Raney nickel causes no further gas evolution. The reaction is then maintained at 50° C. for an additional hour, and subsequently is cooled to room temperature. The reaction mixture is filtered through a pad of celite (rinsing the pad with methanol). N-(3-Morpholin-4-yl-propyl)-benzene-1,4-diamine (4.39 gms.) is isolated upon evaporation of the filtrate, and is subsequently used without purification in the reaction of Example 297.

Example 298–301 are prepared by substituting the appropriate 6'-fluoro or 5'-chloro or 5'-fluoro or 4'-fluoro substituted 1,3-dihydro-indol-2-one for the 1,3-dihydro-indol-2-one and N-(3-morpholin-4-yl-propyl)-benzene-1,4-diamine (used in the preparation of Example 297) for aniline in the reaction of Example 1.

EXAMPLE 302

3-({4-[3-(4-Methyl-piperazin-1-yl)-propylamino]-phenylamino}-methylene)-1,3-dihydro-indol-2-one The named compound is prepared by refluxing 0.135 gms. E & Z 3-[(hydroxy)-methylene]-1,3-dihydro-indol-2-one, as prepared in Example 1, with 0.035 gms. N-[3-(4-Methyl-piperazin-1-yl)-propyl]-benzene-1,4-diamine in tetrahydrofuran (1 mL) for 24 hours. Following concentration in vacuo and recrystallization from hot isopropanol and filtration the named compound is isolated as a yellow solid in the amount of 0.0151 gms.

N-[3-(4-Methyl-piperazin-1-yl)-propyl]-benzene-1,4-diamine was prepared from p-fluoronitrobenzene by the following method:

A mixture of 4.44 mL of p-fluoronitrobenzene, 6 gms. 3-(4-methyl-piperazin-1-yl)-propylamine and 6.65 mL N,N-diisopropylamine in 19 mL dioxane is heated at 105° C. for 2 days. The reaction mixture is cooled to room temperature, evaporated to dryness, and recrystallized from hot isopropanol yielding [3-(4-methyl-piperazin-1-yl)-propyl]-(4-nitro-phenyl)-amine in the amount of 0.1385 gms.

A suspension of 0.1385 gms. of [3-(4-methyl-piperazin-1-yl)-propyl]-(4-nitro-phenyl)-amine in 3 mL of ethanol is heated to 50° C. Once dissolution is achieved 0.144 mL hydrazine monohydrate is addded to the solution. A Raney nickel slurry in water is added to the 50° C. solution dropwise, waiting after each addition for the gas evolution to cease. Sufficient quantities of Raney nickel have been added when continued addition of Raney nickel causes no further gas evolution. The reaction is then maintained at 50° C. for an additional hour, and subsequently is cooled to room temperature. The reaction mixture is filtered through a pad of celite (rinsing the pad with methanol). N-[3-(4-Methyl-piperazin-1-yl)-propyl]-benzene-1,4-diamine (0.116 gms.) is isolated upon evaporation of the filtrate, and is subsequently used without purification in the reaction of Example 302.

EXAMPLE 303

4-Methyl-3-({4-[3-(4-methyl-piperazin-1-yl)-propylamino]-phenylamino}-methylene)-1,3-dihydro-indol-2-one The named compound is prepared by substituting 4-methyl-1,3-dihydro-indol-2-one for the 1,3-dihydro-indol-2-one and N-[3-(4-methyl-piperazin-1-yl)-propyl]-benzene-1,4-diamine (used for the preparation of Example 302) for aniline in the reaction of Example 1.

EXAMPLE 304

6-Fluoro-3-({4-[3-(4-methyl-piperazin-1-yl)-propylamino]-phenylamino}-methylene)-1,3-dihydro-indol-2-one The named compound is prepared by substituting 6-fluoro-1,3-dihydro-indol-2-one for the 1,3-dihydro-indol-2-one and N-[3-(4-methyl-piperazin-1-yl)-propyl]-benzene-1,4-diamine (used for the preparation of Example 302) for aniline in the reaction of Example 1.

EXAMPLE 305

3-({4-[3-(3-Fluoro-pyrrolidin-1-yl)-propoxy]-phenylamino}-methylene)-1,3-dihydro-indol-2-one In a manner similar to that described in Example 217, 3-{[4-(3-Iodo-propoxy)-phenylamino]-methylene}-1,3-dihydro-indol-2-one and 3-fluoro-pyrrolidine hydrochloride (226 mg, 1.2 equiv.) (prepared by the method of Giardina, G et al, Synlett (1995), (1), 55–7) are converted to the named compound as a slightly brownish yellow solid (258 mg, 45%).

EXAMPLE 306

3-{[4-(2-Morpholin-4-yl-ethyl)-phenylamino]-methylene}-1,3-dihydro-indol-2-one

The named compound is prepared by refluxing 0.0644 gms. E & Z 3-[(hydroxy)-methylene]-1,3-dihydro-indol-2-one, as prepared in Example 1, with 0.1088 gms. 4-(2-morpholin-4-yl-ethyl)-phenylamine in tetrahydrofuran (1.5 mL) overnight. Following cooling to room temperture, solvent evaporation in vacuo, trituration with isopropanol and filtration the reaction yields the named compound in the amount of 91.1 mg.

4-(2-Morpholin-4-yl-ethyl)-phenylamine is prepared from (4-nitro-phenyl)-acetic acid by the following method:

A room temperature solution of 1.8839 gms. (4-Nitro-phenyl)-acetic acid in tetrahydrofuran (5 mL) is treated with 1.8069 gms. 1',1'-carbonyl-diimidizole. The reaction mixture is stirred for 1 h. The reaction mixture is then treated with 1.0 mL morpholine. The reaction is heated overnight at 35° C. The reaction is then allowed to cool to room temperature, and is made basic with the addition of saturated aqueous sodium bicarbonate. The resulting mixture is extracted with ethyl acetate. The aqueous layer is re-extracted four more times with ethyl acetate. The combined organics are evaporated to dryness in vacuo. The crude product residue is then chromatographed by flash silica gel chromatography using 60% ethyl acetate in hexanes as the eluant. Following evaporation of solvent, 1-morpholin-4-yl-2-(4-nitro-phenyl)-ethanone is isolated as a white solid in the amount of 1.4009 gms.

1-Morpholin-4-yl-2-(4-nitro-phenyl)-ethanone (1.4009 gms.) is then dissolved in tetrahydrofuran (7.5 mL) and slowly added dropwise to a 0° C., 1.0M solution (40 mL) of Borane in tetrahydrofuran. The reaction mixture is maintained at 0° C. for 30 minutes following the completion of the addition to the Borane/tetrahydrofuran solution. The reaction mixture is then allowed to warm to room temperature, and is subsequently refluxed using an oil bath. The reaction mixture is maintained at refluxing temperature overnight, then cooled to 0° C., and quenched with the addition of concentrated HCl (added until fizzing stops). The quenched reaction mixture is then warmed to room temperature, and extracted with ethyl acetate and water. The organic layer is then separated, dried over sodium sulfate and concentrated in vacuo. The solid isolated is then chromatographed by flash silica gel chromatography using 30% ethyl acetate in hexanes as the eluant to yield 0.7993 gms. of 4-[2-(4-nitro-phenyl)-ethyl]-morpholine as a white solid.

4-[2-(4-Nitro-phenyl)-ethyl]-morpholine (0.7993 gms.) is suspended in 30 mL of a 1:1 (v:v) solution of acetic acid and water. The suspension is then immersed in a 60° C. oil bath and treated in dropwise fashion with 40 mL of an ~10 wt. % solution of TiCl$_3$ in 20–30 wt. % HCl. The reaction mixture is maintained in the 60° C. oil bath overnight following the addition of TiCl$_3$. The reaction mixture is then cooled to 0° C., and is made basic with the addition of a 10% aqueous solution of NaOH. The basic reaction mixture is then extracted with chloroform. The emmulsion that forms is filtered through glass wool, re-extracted with chloroform and then dried over anhydrous sodium sulfate. Following evaporation of the solvent the residue is chromatographed by flash silica gel chromatography (10% methanol in chloroform) which then yielding 0.6528 gms. of 4-(2-morpholin-4-yl-ethyl)-phenylamine.

EXAMPLE 308

4-Methyl-3-{[4-(2-morpholin-4-yl-ethyl)-phenylamino]-methylene}-1,3-dihydro-indol-2-one The named compound is prepared by refluxing 0.0707 gms. E & Z-3-Hydroxymethylene-4-methyl-1,3-dihydro-indol-2-one, as prepared in the reaction of Example 1, with 0.1088 gms. 4-(2-morpholin-4-yl-ethyl)-phenylamine (used in the preparation of Example 306) in tetrahydrofuran (1.5 mL) overnight. Following cooling to room temperture, solvent evaporation in vacuo, trituration with isopropanol and filtration the reaction yields the named compound as a solid in the amount of 77 mg.

Examples 307 and 309–311 are prepared by substituting the appropriate 5'-chloro or 4'-fluoro or 5'-fluoro or 6'-fluoro substituted 1,3-dihydro-indol-2-one for the 1,3-dihydro-indol-2-one and 4-(2-morpholin-4-yl-ethyl)-phenylamine (used in the preparation of Example 306) for aniline in the reaction of Example 1.

EXAMPLE 312

3-{[4-(4-Morpholin-4-yl-butyl)-phenylamino]-methylene}-1,3-dihydro-indol-2-one

The named compound is prepared by refluxing 0.0687 gms. E & Z 3-[(hydroxy)-methylene]-1,3-dihydro-indol-2-one, as prepared in Example 1, with 0.131 gms. 4-(4-morpholin-4-yl-butyl)-phenylamine in tetrahydrofuran (1.5 mL) overnight. Following cooling to room temperture, solvent evaporation in vacuo, trituration with isopropanol and filtration the reaction yields the named compound in the amount of 0.1165 gms.

4-(4-Morpholin-4-yl-butyl)-phenylamine is prepared from 4-(4-nitro-phenyl)-butyric acid by the following method:

A room temperature solution of 1.1180 gms. 4-(4-nitro-phenyl)-butyric acid in tetrahydrofuran (3 mL) is treated with 0.9052 gms. 1',1'-carbonyl-diimidizole using an ice bath to attenuate the intensity of the reaction. The reaction mixture is stirred for 1 h. The reaction mixture is then treated with 0.5 mL morpholine. The reaction is heated overnight at 35° C. The reaction is then allowed to cool to room temperature, and is made basic with the addition of saturated aqueous sodium bicarbonate. The resulting mixture is extracted with ethyl acetate. The organics are dried over anhydrous sodium sulfate, filtered and evaporated to dryness in vacuo. The crude product residue is then chromatographed by flash silica gel chromatography using 60% ethyl acetate in hexanes as the eluant. Following evaporation of solvent, 1-morpholin-4-yl-4-(4-nitro-phenyl)-butan-1-one is isolated as a white solid in the amount of 1.3925 gms.

1-Morpholin-4-yl-4-(4-nitro-phenyl)-butan-1-one (1.3925 gms.) is then dissolved in tetrahydrofuran (7.0 mL) and added dropwise to a 0° C., 1.0M solution (40 mL) of Borane in tetrahydrofuran. The reaction mixture is maintained at 0° C. for 1 hour following the completion of the addition to the Borane/tetrahydrofuran solution. The reaction mixture is then allowed to warm to room temperature, and is subsequently refluxed using an oil bath. The reaction mixture is maintained at refluxing temperature overnight, then is cooled to 0° C. and quenched with the addition of concentrated HCl (added until fizzing stops). The quenched reaction mixture is then warmed to room temperature, and extracted with ethyl acetate and water. The aqueous layer is then extracted twice more with ethyl acetate. The combined organic layers are concentrated in vacuo. The solid isolated is then chromatographed by flash silica gel chromatography using 50% ethyl acetate in hexanes as the eluant to yield 0.9559 gms. of 4-[4-(4-nitro-phenyl)-butyl]-morpholine as a white solid.

4-[4-(4-Nitro-phenyl)-butyl]-morpholine (0.9337 gms.) is suspended in 30 mL of a 1:1 (v:v) solution of acetic acid and water. The suspension is then immersed in a 60° C. oil bath and treated in dropwise fashion with 40 mL of an ~10 wt. % solution of $TiCl_3$ in 20–30 wt. % HCl. The reaction mixture is maintained in the 60° C. oil bath overnight following the addition of $TiCl_3$. The reaction mixture is then cooled to 0° C., and is made basic with the addition of a 10% aqueous solution of NaOH. The basic reaction mixture is then extracted with chloroform. The emulsion that forms is filtered through glass wool, and then the layers are separated. The organic layer is dried over anhydrous sodium sulfate. Following filtration and evaporation of the solvent the residue is chromatographed by flash silica gel chromatography (10% methanol in chloroform) which then yielding 0.905 gms. of 4-(4-morpholin-4-yl-butyl)-phenylamine.

EXAMPLE 314

4-Methyl-3-{[4-(4-morpholin-4-yl-butyl)-phenylamino]-methylene}-1,3-dihydro-indol-2-one The named compound is prepared by refluxing 0.131 gms. E & Z-3-hydroxymethylene-4-methyl-1,3-dihydro-indol-2-one, as prepared in the reaction of Example 1, with 0.0759 gms. 4-(4-morpholin-4-yl-butyl)-phenylamine (used in the preparation of Example 312) in tetrahydrofuran (1.5 mL) overnight. Following cooling to room temperature, solvent evaporation in vacuo, trituration with isopropanol and filtration the reaction yields the named compound as a solid in the amount of 98.0 mg.

Examples 313 and 315–317 are prepared by substituting the appropriate 5'-chloro or 4'-fluoro or 5'-fluoro or 6'-fluoro substituted 1,3-dihydro-indol-2-one for the 1,3-dihydro-indol-2-one and 4-(4-morpholin-4-yl-butyl)-phenylamine (used in the preparation of Example 312) for aniline in the reaction of Example 1.

EXAMPLE 318

3-{[4-(4-Piperidin-1-yl-butyl)-phenylamino]-methylene}-1,3-dihydro-indol-2-one

The named compound is prepared by refluxing 0.0355 gms. E & Z 3-[(hydroxy)-methylene]-1,3-dihydro-indol-2-one, as prepared in Example 1, with 0.070 gms. 4-(4-piperidin-1-yl-butyl)-phenylamine in tetrahydrofuran (1.0 mL) overnight. Following cooling to room temperature, solvent evaporation in vacuo, trituration with isopropanol and filtration the reaction yields the named compound in the amount of 52.6 mg. 4-(4-Piperidin-1-yl-butyl)-phenylamine is prepared from 4-(4-nitro-phenyl)-butyric acid by the following method:

A room temperature solution of 1.1220 gms. 4-(4-nitrophenyl)-butyric acid in tetrahydrofuran (3 mL) is treated with 0.8978 gms. 1',1'-carbonyl-diimidizole using an ice bath to attenuate the intensity of the reaction. The reaction mixture is stirred for 30 minutes in the ice bath and 30 minutes at room temperature. The reaction mixture is then treated with 0.5 mL morpholine. The reaction was heated overnight at 35° C. The reaction is then allowed to cool to room temperature, and is made basic with the addition of saturated aqueous sodium bicarbonate. The resulting mixture is extracted with ethyl acetate. The organics are dried over anhydrous sodium sulfate, filtered and evaporated to dryness in vacuo. The crude product residue is then purified by filtering it through a plug of silica gel using 50% ethyl acetate in hexanes as the eluant. Following evaporation of solvent, 4-(4-nitro-phenyl)-1-piperidin-1-yl-butan-1-one is isolated as a yellow oil in the amount of 1.47 gms.

4-(4-Nitro-phenyl)-1-piperidin-1-yl-butan-1-one (1.465 gms.) is then dissolved in tetrahydrofuran (7.0 mL) and added dropwise to a 0° C., 1.5M solution (25 mL) of Borane in tetrahydrofuran. The reaction mixture is maintained at 0° C. for 30 minutes following the completion of the addition to the Borane/tetrahydrofuran solution. The reaction mixture is then allowed to warm to room temperature for an hour, and is subsequently refluxed using an oil bath. The reaction mixture is maintained at refluxing temperature overnight, then cooled to 0° C. and quenched with the addition of concentrated HCl (added until gas evolution stops). The quenched reaction mixture is then warmed to room temperature, and extracted with ethyl acetate and water. The emulsion that forms is filtered through glass wool and the layers are separated. The aqueous layer is then extracted three additional times with ethyl acetate. The combined organic layers are concentrated in vacuo. The solid isolated is then chromatographed by flash silica gel chromatography using 30% ethyl acetate in hexanes as the eluant yielding 0.719 gms. of 1-[4-(4-nitro-phenyl)-butyl]-piperidine.

1-[4-(4-Nitro-phenyl)-butyl]-piperidine (0.719 gms.) is suspended in 30 mL of a 1:1 (v:v) solution of acetic acid and water. The suspension is then immersed in a 60° C. oil bath and treated in dropwise fashion with 40 mL of an 10 wt. % solution of $TiCl_3$ in 20–30 wt. % HCl. The reaction mixture is maintained in the 60° C. oil bath overnight following the addition of $TiCl_3$. The reaction mixture is then cooled to 0° C., and is made basic with the addition of a 10% aqueous solution of NaOH. The basic reaction mixture is then extracted with chloroform. The emulsion that forms is filtered through glass wool, and then the layers are separated. The aqueous layer is re-extracted with ethyl acetate three additional times. The combined organic layers are concentrated in vacuo and the residue is chromatographed by flash silica gel chromatography (10% methanol in chloroform) yielding 0.428 gms. of 4-(4-piperidin-1-yl-butyl)-phenylamine.

EXAMPLE 320

4-Methyl-3-{[4-(4-piperidin-1-yl-butyl)-phenylamino]-methylene}-1,3-dihydro-indol-2-one The named compound is prepared by refluxing 0.0410 gms. E & Z-3-Hydroxymethylene-4-methyl-1,3-dihydro-indol-2-one, as prepared in the reaction of Example 1, with 0.070 gms. 4-(4-piperidin-1-yl-butyl)-phenylamine (used in the preparation of Example 318) in tetrahydrofuran (1.0 mL) overnight. Following cooling to room temperature, solvent evaporation in vacuo, trituration with isopropanol and filtration the reaction yields the named compound as a solid in the amount of 38.3 mg.

Examples 319 and 321–323 are prepared by substituting the appropriate 5'-chloro or 4'-fluoro or 5'-fluoro or 6'-fluoro substituted 1,3-dihydro-indol-2-one for the 1,3-dihydro-indol-2-one and 4-(4-piperidin-1-yl-butyl)-phenylamine, used in the preparation of Example 318, for aniline in the reaction of Example 1.

Thus, in accordance with the above examples, the following compounds are synthesized:

3-Phenylaminomethylene-1,3-dihydro-indol-2-one
3-[(3-Bromo-phenylamino)-methylene]-1,3-dihydro-indol-2-one
3-[(4-Bromo-phenylamino)-methyl]-1,3-dihydro-indol-2-one
3-[(3-Bromo-phenylamino)-methyl]-1,3-dihydro-indol-2-one
3-[(4-Ethyl-phenylamino)-methylene]-1,3-dihydro-indol-2-one
3-Ethyl-phenylamino)-methylene]-1,3-dihydro-indol-2-one
3-[(4-Methoxy-phenylamino)-methylene]-1,3-dihydro-indol-2-one
4-[(2-Oxo-1,3-dihydro-indol-3-ylididenemethyl)-amino]-benzoic acid ethyl ester
3-[(2-Ethyl-phenylamino)-methylene}-1,3-dihydro-indol-2-one
3-[(3-Fluoro-4-methyl-phenylamino)-methylene]-1,3-dihydro-indol-2-one
3-[(3-Fluoro-2-methyl-phenylamino)-methylene]-1,3-dihydro-indol-2-one
3-[(4-Hydroxy-phenylamino)-methylene]-1,3-dihydro-indol-2-one
3-[(3-Chloro-4-hydroxy-phenylamino)-methylene]-1,3-dihydro-indol-2-one
3-[(4-Fluoro-2-methyl-phenylamino)-methylene]-1,3-dihydro-indol-2-one
3-[(3-Hydroxy-phenylamino)-methylene]-1,3-dihydro-indol-2-one
3-[(3,5-Dimethoxy-phenylamino)-methylene]-1,3-dihydro-indol-2-one
3-[(4-tert-Butyl-phenylamino)-methylene]-1,3-dihydro-indol-2-one
3-(p-Tolylamino-methylene)-1,3-dihydro-indol-2-one
3-[(3,5-Dimethyl-phenylamino)-methylene]-1,3-dihydro-indol-2-one
3-[(3,4-Dimethyl-phenylamino)-methylene]-1,3-dihydro-indol-2-one
3-[(3-Fluoro-4-methoxy-phenylamino)-methylene]-1,3-dihydro-indol-2-one
3-[(3-Trifluoromethyl-phenylamino)-methylene]-1,3-dihydro-indol-2-one
3-(Indan-5-ylaminomethylene)-1,3-dihydro-indol-2-one
3-[(4-Chloro-2-fluoro-phenylamino)-methylene]-1,3-dihydro-indol-2-one
3-[(4-Trifluoromethyl-phenylamino)-methylene]-1,3-dihydro-indol-2-one
Carbonic acid ethyl ester 4-fluoro-2-methyl-5-[(2-oxo-1,2-dihydro-indol-3-ylidenemethyl)-amino]-phenyl ester
Carbonic acid 2,2-dimethyl-propyl ester 4-fluoro-2-methyl-5-[(2-oxo-1,2-dihydro-indol-3-ylidenemethyl)-amino]-phenyl ester
3-[(4-Chloro-2-fluoro-5-hydroxy-phenylamino)-methylene]-1,3-dihydro-indol-2-one
3-[(4-Cyanophenylamino)-methylene]-1,3-dihydro-indol-2-one
3-[(4-Cyanomethylphenylamino)-methylene]-1,3-dihydro-indol-2-one
3-[(5-Indolylamino)-methylene]-1,3-dihydro-indol-2-one
3-[(5-Indazolylamino)-methylene]-1,3-dihydro-indol-2-one
3-[(4-Benzamidylamino)-methylene]-1,3-dihydro-indol-2-one
3-[(4-Acetanilidylamino)-methylene]-1,3-dihydro-indol-2-one
(3-[(2-Oxo-1,2-dihydro-indol-3-ylidenemethyl)-amino]-phenyl-)acetic acid
3-[(4-Chlorophenylamino)-methylene]-1,3-dihydro-indol-2-one
2-Chloro-5-[(2-oxo-1,2-dihydro-indol-3-ylidenemethyl)-amino]-benzoic acid
2-Oxo-1,2-dihydro-indol-3-ylidenemethyl-sulfanilamide
2-Oxo-1,2-dihydro-indol-3-ylidenemethyl-sulfaacetamide
3-[(4-Morpholinoamino)-methylene]-1,3-dihydro-indol-2-one
3-[(4-Phenoxyamino)-methylene]-1,3-dihydro-indol-2-one
3-[(3,4-Dimethoxyamino)-methylene]-1,3-dihydro-indol-2-one
3-[(6-Benzthioazolylamino)-methylene]-1,3-dihydro-indol-2-one
2-Hydroxy-4-[(2-oxo-1,2-dihydro-indol-3-ylidenemethyl)-amino]-benzoic acid
3-[(Chloro-trifluoromethyl-phenylamino)-methylene]-1,3-dihydro-indol-2-one
3-[(Bis-trifluoromethyl-phenylamino)-methylene]-1,3-dihydro-indol-2-one
3-[(Fluoro-trifluoromethyl-phenylamino)-methylene]-1,3-dihydro-indol-2-one
3-[(3-Hydroxy-4-methyl-phenylamino)-methylene]-1,3-dihydro-indol-2-one
3-[(3-Hydroxy-4-methoxy-phenylamino)-methylene]-1,3-dihydro-indol-2-one
3-{[4-(1,1-Difluoro-methoxy)-phenylamino]-methylene}-1,3-dihydro-indol-2-one
3-[(4-Trifluoromethoxy-phenylamino)-methylene]-1,3-dihydro-indol-2-one
3-[(4-Isopropyl-phenylamino)-methylene]-1,3-dihydro-indol-2-one
3-[(2-Fluoro-4-methyl-phenylamino)-methylene]-1,3-dihydro-indol-2-one
3-[(4-Chloro-3-methyl-phenylamino)-methylene]-1,3-dihydro-indol-2-one
3-[(4-Methoxy-3-trifluoromethyl-phenylamino)-methylene]-1,3-dihydro-indol-2-one
3-[(Methyl-trifluoromethyl-phenylamino)-methylene]-1,3-dihydro-indol-2-one
5-Chloro-3-[(3-methoxy-phenylamino)-methylene]-1,3-dihydro-indol-2-one
4-Methyl-3-phenylaminomethylene-1,3-dihydro-indol-2-one
3-[(4-Methoxy-phenylamino)-methylene]-4-methyl-1,3-dihydro-indol-2-one
3-[(3-Hydroxy-phenylamino)-methylene]-4-methyl-1,3-dihydro-indol-2-one
3-[(3,5-Dimethoxy-phenylamino)-methylene]-4-methyl-1,3-dihydro-indol-2-one
4-Methyl-3-(p-tolylamino-methylene)-1,3-dihydro-indol-2-one
3-[(3,5-Dimethyl-phenylamino)-methylene]-4-methyl-1,3-dihydro-indol-2-one
3-[(4-Difluoromethoxyphenylamino)-methylene]-5-chloro-1,3-dihydro-indol-2-one
3-[(3-Hydroxy-4-methoxyphenylamino)-methylene]-5-chloro-1,3-dihydro-indol-2-one
3-[(4-Trifluoromethoxyphenylamino)-methylene]-5-chloro-1,3-dihydro-indol-2-one
3-[(3-Methyl-4-hydroxyphenylamino)-methylene]-5-chloro-1,3-dihydro-indol-2-one
3-[(3,4-Metylenedioxyphenylamino)-methylene]-5-chloro-1,3-dihydro-indol-2-one 3-[(3,4-Dimethylphenylamino)-methylene]-5-chloro-1,3-dihydro-indol-2-one
3-[(4-i-Propylphenylamino)-methylene]-5-chloro-1,3-dihydro-indol-2-one
3-[(3-Hydroxy-4-methylphenylamino)-methylene]-5-chloro-1,3-dihydro-indol-2-one
5-Chloro-3-{[4-(1-hydroxy-ethyl)-phenylamino]-methylene}-1,3-dihydro-indol-2-one
3-[(4-Methoxyphenylamino)-methylene]-5-chloro-1,3-dihydro-indol-2-one
3-[(Phenylamino)-methylene]-5-chloro-1,3-dihydro-indol-2-one
3-[(3,5-Dimethoxyphenylamino)-methylene]-5-chloro-1,3-dihydro-indol-2-one
3-[(3-Hydroxyphenylamino)-methylene]-5-chloro-1,3-dihydro-indol-2-one
3-[(4-Hydroxyphenylamino)-methylene]-5-chloro-1,3-dihydro-indol-2-one
3-[(3,5-Dimethylphenylamino)-methylene]-5-chloro-1,3-dihydro-indol-2-one
3-[(4-Methylphenylamino)-methylene]-5-chloro-1,3-dihydro-indol-2-one
3-[(3,4-Methylenedioxyphenylamino)-methylene]-1,3-dihydro-indol-2-one
2-Hydoxy-5-[(2-oxo-1,2-dihydro-indol-3-ylidenemethyl)-amino]-benzoic acid
3-[(4-Ethoxyphenylamino)-methylene]-1,3-dihydro-indol-2-one
3-[(1-Acetyl-2,3-dihydro-1-indol-6-ylamino)-methylene]-1,3-dihydro-indol-2-one
4-[(2-Oxo-1,2-dihydro-indol-3-ylidenemethyl)-amino]-phospate
4-[(2-Oxo-1,2-dihydro-indol-3-ylidenemethyl)-amino]-phthalic acid
4-[(2-Oxo-1,2-dihydro-indol-3-ylidenemethyl)-amino]-benzoic acid
3-{[4-(2-Hydroxyethyl)phenylamino]-methylene}-1,3-dihydro-indol-2-one
3-[(4-Hydroxymethyl-phenylamino)-methylene]-1,3-dihydro-indol-2-one
2-Methoxy-4-[(2-oxo-1,2-dihydro-indol-3-ylidenemethyl)-amino]-benzoic acid methyl ester
3-[(1H-Indazol-6-ylamino)-methylene]-4-methyl-1,3-dihydro-indol-2-one
3-[(3-Fluoro-4-methoxy-phenylamino)-methylene]-4-methyl-1,3-dihydro-indol-2-one
3-(Benzothiazol-6-ylaminomethylene)-4-methyl-1,3-dihydro-indol-2-one
2-Methoxy-4-[(4-methyl-2-oxo-1,2-dihydro-indol-3-ylidenemethyl)-amino]-benzoic acid methyl ester
3-[(3-Methoxy-phenylamino)-methylene]-1,3-dihydro-indol-2-one
3-[(3,4-Dimethyl-phenylamino)-methylene]-4-methyl-1,3-dihydro-indol-2-one
3-[(4-Hydroxy-phenylamino)-methylene]-4-methyl-1,3-dihydro-indol-2-one
3-[(1H-Indol-6-ylamino)-methylene]-4-methyl-1,3-dihydro-indol-2-one
3-[(4-tert-Butyl-phenylamino)-methylene]-4-methyl-1,3-dihydro-indol-2-one
3-[(4-Hydroxymethyl-phenylamino)-methylene]-4-methyl-1,3-dihydro-indol-2-one
5-Chloro-3-[(4-t-butyl-phenylamino)-methylene]-1,3-dihydro-indol-2-one
5-Chloro-3-[(phenylamino)-methylene]-1,3-dihydro-indol-2-one benzothiazol-6-yl-amine
5-Chloro-3-[(3,4-dimethoxyphenylamino)-methylene]-1,3-dihydro-indol-2-one
4-(5-Chloro-2-oxo-1,2-dihydro-indol-3-ylidenemethyl)-6-indazolylamine
5-Chloro-3-[(4-chloro-2,5-dimethoxy-phenylamino)-methylene]-1,3-dihydro-indol-2-one
5-Chloro-3-[(3-flouro-4-methoxyphenylamino)-methylene]-1,3-dihydro-indol-2-one
5-Chloro-3-[(4-morpholinophenylamino)-methylene]-1,3-dihydro-indol-2-one
5-Chloro-3-[(4-ethoxyphenylamino)-methylene]-1,3-dihydro-indol-2-one
5-(5-Chloro-2-oxo-1,2-dihydro-indol-3-ylidenemethylamino)-2-hydroxybenzoic acid
5-Chloro-3-[(4-hydoxy-3-(diethylaminomethyl)phenylamino)-methylene]-1,3-dihydro-indol-2-one
5-(5-Chloro-2-oxo-1,2-dihydro-indol-3-ylidenemethylamino)indole
5-Chloro-3-[(4-(hydoxymethyl)phenylamino)-methylene]-1,3-dihydro-indol-2-one
5-Chloro-3-[(4–1-propyl-3-methylphenylamino)-methylene]-1,3-dihydro-indol-2-one
3-{[4-(2-Hydroxy-ethyl)-phenylamino]-methylene}-4-methyl-1,3-dihydro-indol-2-one
N-{4-[(5-Chloro-2-oxo-1,2-dihydro-indol-3-ylidenemethyl)-amino]-phenyl}-acetamide
{4-[(5-Chloro-2-oxo-1,2-dihydro-indol-3-ylidenemethyl)-amino]-phenyl}-acetic acid
4-[(5-Chloro-2-oxo-1,2-dihydro-indol-3-ylidenemethyl)-amino]-benzenesulfonamide
3-[(3-Hydroxy-4-methoxy-phenylamino)-methylene]-4-methyl-1,3-dihydro-indol-2-one
2-Hydroxy-5-[(4-methyl-2-oxo-1,2-dihydro-indol-3-ylidenemethyl)-amino]-benzoic acid
3-{[4-(1,1-Difluoro-methoxy)-phenylamino]-methylene}-4-methyl-1,3-dihydro-indol-2-one
4-Methyl-3-[(4-trifluoromethoxy-phenylamino)-methylene]-1,3-dihydro-indol-2-one
3-[(4-Methoxy-3-trifluoromethyl-phenylamino)-methylene]-4-methyl-1,3-dihydro-indol-2-one
3-[(4-Ethoxy-phenylamino)-methylene]-4-methyl-1,3-dihydro-indol-2-one
3-[(4-Isopropyl-phenylamino)-methylene]-4-methyl-1,3-dihydro-indol-2-one
3-(Benzo[1,3]dioxol-5-ylaminomethylene)-4-methyl-1,3-dihydro-indol-2-one
3-[(3-Hydroxy-4-methyl-phenylamino)-methylene]-4-methyl-1,3-dihydro-indol-2-one
3-[(3,4-Dimethoxy-phenylamino)-methylene]-4-methyl-1,3-dihydro-indol-2-one
3-[(2-Ethyl-phenylamino)-methylene]-4-methyl-1,3-dihydro-indol-2-one
4-[(4-Methyl-2-oxo-1,2-dihydro-indol-3-ylidenemethyl)-amino]-benzonitrile
4-[(4-Methyl-2-oxo-1,2-dihydro-indol-3-ylidenemethyl)-amino]-benzamide
N-{4-[(4-Methyl-2-oxo-1,2-dihydro-indol-3-ylidenemethyl)-amino]-phenyl}-acetamide
{4-[(4-Methyl-2-oxo-1,2-dihydro-indol-3-ylidenemethyl)-amino]-phenyl}-acetic acid
3-[(4-Hydroxy-3-methyl-phenylamino)-methylene]-4-methyl-1,3-dihydro-indol-2-one
3-[(4-Hydroxy-3-methyl-phenylamino)-methylene]-1,3-dihydro-indol-2-one {2-Hydroxy-4-[(2-oxo-1,2-dihydro-indol-3-ylidenemethyl)-amino]-phenyl}-carbamic acid ethyl ester 3-[(2-Fluoro-4-methoxy-phenylamino)-methylene]-4-methyl-1,3-dihydro-indol-2-one
3-[(4-Methylsulfanyl-phenylamino)-methylene]-1,3-dihydro-indol-2-one
4-Methyl-3-[(4-methylsulfanyl-phenylamino)-methylene]-1,3-dihydro-indol-2-one
5-Chloro-3-[(4-methylsulfanyl-phenylamino)-methylene]-1,3-dihydro-indol-2-one
4-{4-[(2-Oxo-1,2-dihydro-indol-3-ylidenemethyl)-amino]-phenyl}-butyric acid
4-{4-[(4-Methyl-2-oxo-1,2-dihydro-indol-3-ylidenemethyl)-amino]-phenyl}-butyric acid
3-{3-[(2-Oxo-1,2-dihydro-indol-3-ylidenemethyl)-amino]-phenyl}-propionic acid
3-{3-[(4-Methyl-2-oxo-1,2-dihydro-indol-3-ylidenemethyl)-amino]-phenyl}-propionic acid
3-{3-[(5-Chloro-2-oxo-1,2-dihydro-indol-3-ylidenemethyl)-amino]-phenyl}-propionic acid
3-{4-[(2-Oxo-1,2-dihydro-indol-3-ylidenemethyl)-amino]-phenyl}-propionic acid
3-{4-[(4-Methyl-2-oxo-1,2-dihydro-indol-3-ylidenemethyl)-amino]-phenyl}-propionic acid
3-{4-[(5-Chloro-2-oxo-1,2-dihydro-indol-3-ylidenemethyl)-amino]-phenyl}-propionic acid
3-[(3-Ethyl-phenylamino)-methylene]-4-methyl-1,3-dihydro-indol-2-one
5-Chloro-3-[(3-ethyl-phenylamino)-methylene]-1,3-dihydro-indol-2-one
5-Chloro-3-[(4-ethyl-phenylamino)-methylene]-1,3-dihydro-indol-2-one
4-{4-[(5-Chloro-2-oxo-1,2-dihydro-indol-3-ylidenemethyl)-amino]-phenyl}-butyric acid
3-[(4-Ethyl-phenylamino)-methylene]-4-methyl-1,3-dihydro-indol-2-one
4-[(5-Chloro-2-oxo-1,2-dihydro-indol-3-ylidenemethyl)-amino]-benzonitrile
2-Hydroxy-4-[(4-methyl-2-oxo-1,2-dihydro-indol-3-ylidenemethyl)-amino]-benzoic acid
3-[(4-Dimethylamino-phenylamino)-methylene]-1,3-dihydro-indol-2-one
3-{[4-(4-Methyl-piperazin-1-yl)-phenylamino]-methylene}-1,3-dihydro-indol-2-one
3-[(4-Piperidin-1-yl-phenylamino)-methylene]-1,3-dihydro-indol-2-one
3-{[4-(2,6-Dimethyl-morpholin-4-yl)-phenylamino]-methylene}-1,3-dihydro-indol-2-one
3-[(3-Diethylaminomethyl-4-hydroxy-phenylamino)-methylene]-1,3-dihydro-indol-2-one
3-[(3-Diethylaminomethyl-4-hydroxy-phenylamino)-methylene]-4-methyl-1,3-dihydro-indol-2-one
5-Fluoro-3-[(1 h-indol-5-ylamino)-methylene]-1,3-dihydro-indol-2-one
5-Fluoro-3-[(1 h-indazol-6-ylamino)-methylene]-1,3-dihydro-indol-2-one
5-Fluoro-3-[(3-hydroxy-4-methoxy-phenylamino)-methylene]-1,3-dihydro-indol-2-one
3-{4-[(5-Fluoro-2-oxo-1,2-dihydro-indol-3-ylidenemethyl)-amino]-phenyl}-propionic acid
4-[(5-Fluoro-2-oxo-1,2-dihydro-indol-3-ylidenemethyl)-amino]-benzenesulfonamide
5-Fluoro-3-[(4-morpholin-4-yl-phenylamino)-methylene]-1,3-dihydro-indol-2-one
5-Fluoro-3-{[4-(4-methyl-piperazin-1-yl)-phenylamino]-methylene}-1,3-dihydro-indol-2-one
5-Fluoro-3-phenylaminomethylene-1,3-dihydro-indol-2-one
4-[(5-Fluoro-2-oxo-1,2-dihydro-indol-3-ylidenemethyl)-amino]-benzamide
5-Fluoro-3-[(4-methylsulfanyl-phenylamino)-methylene]-1,3-dihydro-indol-2-one
5-Fluoro-3-[(3-fluoro-4-methoxy-phenylamino)-methylene]-1,3-dihydro-indol-2-one
3-(Benzothiazol-6-ylaminomethylene)-5-fluoro-1,3-dihydro-indol-2-one {4-[(5-Fluoro-2-oxo-1,2-dihydro-indol-3-ylidenemethyl)-amino]-phenyl}-acetic acid
3-{3-[(5-Fluoro-2-oxo-1,2-dihydro-indol-3-ylidenemethyl)-amino]-phenyl}-propionic acid
3-[(3-Ethyl-phenylamino)-methylene]-5-fluoro-1,3-dihydro-indol-2-one
5-Fluoro-3-[(3-hydroxy-phenylamino)-methylene]-1,3-dihydro-indol-2-one
5-Fluoro-3-[(4-hydroxymethyl-phenylamino)-methylene]-1,3-dihydro-indol-2-one
3-{[4-(4-Pyrrolidin-1-yl-butoxy)-phenylamino]-methylene}-1,3-dihydro-indol-2-one
3-[(4-Amino-phenylamino)-methylene]-1,3-dihydro-indol-2-one
3-[(4-Amino-phenylamino)-methylene]-4-methyl-1,3-dihydro-indol-2-one
3-{[3-(1-Hydroxy-ethyl)-phenylamino]-methylene}-1,3-dihydro-indol-2-one
3-{[3-(1-Hydroxy-ethyl)-phenylamino]-methylene}-4-methyl-1,3-dihydro-indol-2-one
3-[(3-Hydroxymethyl-phenylamino)-methylene]-1,3-dihydro-indol-2-one
3-[(3-Hydroxymethyl-phenylamino)-methylene]-4-methyl-1,3-dihydro-indol-2-one
{4-[(2-Oxo-1,2-dihydro-indol-3-ylidenemethyl)-amino]-phenyl}-carbamic acid tert-butyl ester
{4-[(4-Methyl-2-oxo-1,2-dihydro-indol-3-ylidenemethyl)-amino]-phenyl}-carbamic acid tert-butyl este
3-[(4-Diethylamino-phenylamino)-methylene]-1,3-dihydro-indol-2-one
3-[(4-Diethylamino-phenylamino)-methylene]-4-methyl-1,3-dihydro-indol-2-one
N,N-Bis-(2-hydroxy-ethyl)-3-[(2-oxo-1,2-dihydro-indol-3-ylidenemethyl)-amino]-benzenesulfonamide
N,N-Bis-(2-hydroxy-ethyl)-3-[(4-methyl-2-oxo-1,2-dihydro-indol-3-ylidenemethyl)-amino]-benzenesulfonamide
N-(2-Hydroxy-ethyl)-4-[(2-oxo-1,2-dihydro-indol-3-ylidenemethyl)-amino]-benzenesulfonamide
N-(3-Hydroxy-propyl)-3-[(2-oxo-1,2-dihydro-indol-3-ylidenemethyl)-amino]-benzenesulfonamide
N-(3-Hydroxy-propyl)-3-[(4-methyl-2-oxo-1,2-dihydro-indol-3-ylidenemethyl)-amino]-benzenesulfonamid
2-Morpholin-4-yl-5-[(2-oxo-1,2-dihydro-indol-3-ylidenemethyl)-amino]-benzoic acid
4-Methyl-3-{[4-(1-morpholin-4-yl-methanethioyl)-phenylamino]-methylene}-1,3-dihydro-indol-2-one
N-(2-Hydroxy-ethyl)-4-[(4-methyl-2-oxo-1,2-dihydro-indol-3-ylidenemethyl)-amino]-benzenesulfonamide
3-{[4-(3-Chloro-propoxy)-phenylamino]-methylene}-1,3-dihydro-indol-2-one
3-{[4-(4-Chloro-butoxy)-phenylamino]-methylene}-1,3-dihydro-indol-2-one
3-{[4-(3-Iodo-propoxy)-phenylamino]-methylene}-1,3-dihydro-indol-2-one
3-{[4-(4-Iodo-butoxy)-phenylamino]-methylene}-1,3-dihydro-indol-2-one.
4-Methyl-3-phenylaminomethylene-2,3,4,5,6-d4–1,3-dihydro-indol-2-one
4-[(2-Oxo-1,2-dihydro-indol-3-ylidenemethyl)-amino]-benzoic-2,3,5,6-d4 acid 3-[(4-Amino-phenylamino)-methylene]-2,3,5,6-d4–1,3-dihydro-indol-2-one
3-[(4-Amino-phenylamino)-methylene]-2,3,5,6-d4–4-methyl-1,3-dihydro-indol-2-one
3-{[4-(4-Morpholin-4-yl-butoxy)-phenylamino]-methylene}-1,3-dihydro-indol-2-one
3-{[4-(4-Diethylamino-butoxy)-phenylamino]-methylene}-1,3-dihydro-indol-2-one
3-({4-[4-(4-Methyl-piperazin-1-yl)-butoxy]-phenylamino}-methylene)-1,3-dihydro-indol-2-one
3-{[4-(4-Piperidin-1-yl-butoxy)-phenylamino]-methylene}-1,3-dihydro-indol-2-one
3-[(3-Amino-phenylamino)-methylene]-4-methyl-1,3-dihydro-indol-2-one
3-[(3-Amino-phenylamino)-methylene]-1,3-dihydro-indol-2-one
3-[(3-Amino-4-methyl-phenylamino)-methylene]-1,3-dihydro-indol-2-one
3-[(3-Amino-4-methyl-phenylamino)-methylene]-4-methyl-1,3-dihydro-indol-2-one
3-{[4-(3-Diethylamino-propoxy)-phenylamino]-methylene}-1,3-dihydro-indol-2-one
3-{[4-(3-Morpholin-4-yl-propoxy)-phenylamino]-methylene}-1,3-dihydro-indol-2-one
3-{[4-(3-Pyrrolidin-1-yl-propoxy)-phenylamino]-methylene}-1,3-dihydro-indol-2-one
3-({4-[3-(4-Methyl-piperazin-1-yl)-propoxy]-phenylamino}-methylene)-1,3-dihydro-indol-2-one
3-{[4-(3-Piperidin-1-yl-propoxy)-phenylamino]-methylene}-1,3-dihydro-indol-2-one
3-{[4-(2,6-Dimethyl-morpholin-4-yl)-phenylamino]-methylene}-5-fluoro-1,3-dihydro-indol-2-one
3-{[4-(2,6-Dimethyl-morpholin-4-yl)-phenylamino]-methylene}-4-methyl-1,3-dihydro-indol-2-one
3-Phenylaminomethylene-2,3,4,5,6-d4-1,3-dihydro-indol-2-one
5-Fluoro-3-[(4-methoxy-phenylamino)-methylene]-1,3-dihydro-indol-2-one
5-Fluoro-3-[(4-piperidin-1-yl-phenylamino)-methylene]-1,3-dihydro-indol-2-one
3-[(4-Carboxymethylphenylamino)-methylene]-1,3-dihydro-indol-2-one
3-{[4-(3-thiomorpholin-4-yl-propoxy)-phenylamino]-methylene}-1,3-dihydro-indol-2-one
3-{[4-(4-Thiomorpholin-4-yl-butoxy)-phenylamino]-methylene}-1,3-dihydro-indol-2-one
4-Methyl-3-[(4-morpholin-4-yl-phenylamino)-methylene]-1,3-dihydro-indol-2-one
6-Fluoro-3-[(4-morpholin-4-yl-phenylamino)-methylene]-1,3-dihydro-indol-2-one
3-{[4-(2,6-Dimethyl-morpholin-4-yl)-phenylamino]-methylene}-6-fluoro-1,3-dihydro-indol-2-one
6-Fluoro-3-{[4-(4-methyl-piperazin-1-yl)-phenylamino]-methylene}-1,3-dihydro-indol-2-one
3-{[4-(3-Diethylamino-propoxy)-phenylamino]-methylene}-4-methyl-1,3-dihydro-indol-2-one
5-Chloro-3-{[4-(3-diethylamino-propoxy)-phenylamino]-methylene}-1,3-dihydro-indol-2-one
3-{[4-(3-Diethylamino-propoxy)-phenylamino]-methylene}-5-fluoro-1,3-dihydro-indol-2-one
3-{[4-(3-Diethylamino-propoxy)-phenylamino]-methylene}-6-fluoro-1,3-dihydro-indol-2-one
3-{[4-(2-Morpholin-4-yl-ethylamino)-phenylamino]-methylene}-1,3-dihydro-indol-2-one
3-[(4-Morpholin-4-yl-phenylamino)-methylene]-5-nitro-1,3-dihydro-indol-2-one
3-[(4-Morpholin-4-yl-phenylamino)-methylene]-2-oxo-2,3-dihydro-1h-indole-5-carbonitrile
4-Methyl-3-{[4-(3-piperidin-1-yl-propoxy)-phenylamino]-methylene}-1,3-dihydro-indol-2-one
6-Fluoro-3-{[4-(3-piperidin-1-yl-propoxy)-phenylamino]-methylene}-1,3-dihydro-indol-2-one
5-Fluoro-3-{[4-(3-piperidin-1-yl-propoxy)-phenylamino]-methylene}-1,3-dihydro-indol-2-one
5-Chloro-3-{[4-(3-piperidin-1-yl-propoxy)-phenylamino]-methylene}-1,3-dihydro-indol-2-one
4-Methyl-3-{[4-(2-morpholin-4-yl-ethylamino)-phenylamino]-methylene}-1,3-dihydro-indol-2-one
6-Fluoro-3-{[4-(2-morpholin-4-yl-ethylamino)-phenylamino]-methylene}-1,3-dihydro-indol-2-one
5-Fluoro-3-{[4-(2-morpholin-4-yl-ethylamino)-phenylamino]-methylene}-1,3-dihydro-indol-2-one
5-Chloro-3-{[4-(2-morpholin-4-yl-ethylamino)-phenylamino]-methylene}-1,3-dihydro-indol-2-one
4-methyl-3-{[4-(4-piperidin-1-yl-butoxy)-phenylamino]-methylene}-1,3-dihydro-indol-2-one
6-Fluoro-3-{[4-(4-piperidin-1-yl-butoxy)-phenylamino]-methylene}-1,3-dihydro-indol-2-one
3-{[4-(3-Diethylamino-propoxy)-3-fluoro-phenylamino]-methylene}-1,3-dihydro-indol-2-one
3-{[4-(3-Diethylamino-propoxy)-3-fluoro-phenylamino]-methylene}-4-methyl-1,3-dihydro-indol-2-one
3-{[4-(3-Diethylamino-propoxy)-3-fluoro-phenylamino]-methylene}-6-fluoro-1,3-dihydro-indol-2-one
3-[(4-Piperidin-1-ylmethyl-phenylamino)-methylene]-1,3-dihydro-indol-2-one
4-Methyl-3-{[4-(2-piperidin-1-yl-ethoxy)-phenylamino]-methylene}-1,3-dihydro-indol-2-one
6-Fluoro-3-{[4-(2-piperidin-1-yl-ethoxy)-phenylamino]-methylene}-1,3-dihydro-indol-2-one
3-{[4-(2-Piperidin-1-yl-ethoxy)-phenylamino]-methylene}-1,3-dihydro-indol-2-one
4-Fluoro-3-{[4-(3-piperidin-1-yl-propoxy)-phenylamino]-methylene}-1,3-dihydro-indol-2-one
4-Methyl-3-[(4-piperidin-1-ylmethyl-phenylamino)-methylene]-1,3-dihydro-indol-2-one
4-Fluoro-3-[(4-piperidin-1-ylmethyl-phenylamino)-methylene]-1,3-dihydro-indol-2-one
5-Fluoro-3-[(4-piperidin-1-ylmethyl-phenylamino)-methylene]-1,3-dihydro-indol-2-one
6-Fluoro-3-[(4-piperidin-1-ylmethyl-phenylamino)-methylene]-1,3-dihydro-indol-2-one
5-Chloro-3-[(4-piperidin-1-ylmethyl-phenylamino)-methylene]-1,3-dihydro-indol-2-one
4-Fluoro-3-{[4-(2-piperidin-1-yl-ethoxy)-phenylamino]-methylene}-1,3-dihydro-indol-2-one
5-Chloro-3-{[4-(2-piperidin-1-yl-ethoxy)-phenylamino]-methylene}-1,3-dihydro-indol-2-one
5-Fluoro-3-{[4-(2-piperidin-1-yl-ethoxy)-phenylamino]-methylene}-1,3-dihydro-indol-2-one
3-{[4-(2-Diethylamino-ethoxy)-phenylamino]-methylene}-4-methyl-1,3-dihydro-indol-2-one
3-{[4-(2-Diethylamino-ethoxy)-phenylamino]-methylene}-1,3-dihydro-indol-2-one
3-{[4-(2-Diethylamino-ethoxy)-phenylamino]-methylene}-6-fluoro-1,3-dihydro-indol-2-one
3-{[4-(3-Diethylamino-propoxy)-3-fluoro-phenylamino]-methylene}-4-fluoro-1,3-dihydro-indol-2-one
6-(3-Methoxy-phenyl)-3-{[4-(4-methyl-piperazin-1-yl)-phenylamino]-methylene}-1,3-dihydro-indol-2-one
6-(3-Methoxy-phenyl)-3-{[4-morpholin-4-yl-phenylamino)-methylene]-1,3-dihydro-indol-2-one 4-Methyl-3-{[4-(2-pyrrolidin-1-yl-ethoxy)-phenylamino]-methylene}-1,3-dihydro-indol-2-one
6-Fluoro-3-{[4-(2-pyrrolidin-1-yl-ethoxy)-phenylamino]-methylene}-1,3-dihydro-indol-2-one
3-{[4-(2-Pyrrolidin-1-yl-ethoxy)-phenylamino]-methylene}-1,3-dihydro-indol-2-one
4-Fluoro-3-{[4-(2-pyrrolidin-1-yl-ethoxy)-phenylamino]-methylene}-1,3-Dihydro-indol-2-one
5-Fluoro-3-{[4-(2-pyrrolidin-1-yl-ethoxy)-phenylamino]-methylene}-1,3-dihydro-indol-2-one
5-Chloro-3-{[4-(2-pyrrolidin-1-yl-ethoxy)-phenylamino]-methylene}-1,3-dihydro-indol-2-one
6-(3-Methoxy-phenyl)-3-{[4-(3-piperidin-1-yl-propoxy)-phenylamino]-methylene}-1,3-dihydro-indol-2-one
3-{[4-(3-Diethylamino-propoxy)-phenylamino]-methylene}-6-(3-methoxy-phenyl)-1,3-dihydro-indol-2-one
4-Methyl-3-{[4-(1-methyl-piperidin-3-ylmethoxy)-phenylamino]-methylene}-1,3-dihydro-indol-2-one
6-Fluoro-3-{[4-(1-methyl-piperidin-3-ylmethoxy)-phenylamino]-methylene}-1,3-dihydro-indol-2-one
3-{[4-(1-Methyl-piperidin-3-ylmethoxy)-phenylamino]-methylene}-1,3-dihydro-indol-2-one
4-Fluoro-3-{[4-(1-methyl-piperidin-3-ylmethoxy)-phenylamino]-methylene}-1,3-dihydro-indol-2-one
5-Fluoro-3-{[4-(1-methyl-piperidin-3-ylmethoxy)-phenylamino]-methylene}-1,3-dihydro-indol-2-one
5-Chloro-3-{[4-(1-methyl-piperidin-3-ylmethoxy)-phenylamino]-methylene}-1,3-dihydro-indol-2-one
3-{[4-(2-Piperidin-1-yl-ethyl)-phenylamino]-methylene}-1,3-dihydro-indol-2-one
5-Chloro-3-{[4-(2-piperidin-1-yl-ethyl)-phenylamino]-methylene}-1,3-dihydro-indol-2-one
4-Methyl-3-{[4-(2-piperidin-1-yl-ethyl)-phenylamino]-methylene}-1,3-dihydro-indol-2-one
4-Fluoro-3-{[4-(2-piperidin-1-yl-ethyl)-phenylamino]-methylene}-1,3-dihydro-indol-2-one
5-Fluoro-3-{[4-(2-piperidin-1-yl-ethyl)-phenylamino]-methylene}-1,3-dihydro-indol-2-one
6-Fluoro-3-{[4-(2-piperidin-1-yl-ethyl)-phenylamino]-methylene}-1,3-dihydro-indol-2-one
3-[(4-Morpholin-4-ylmethyl-phenylamino)-methylene]-1,3-dihydro-indol-2-one
5-Chloro-3-[(4-morpholin-4-ylmethyl-phenylamino)-methylene]-1,3-dihydro-indol-2-one
4-Methyl-3-[(4-morpholin-4-ylmethyl-phenylamino)-methylene]-1,3-dihydro-indol-2-one
4-Fluoro-3-[(4-morpholin-4-ylmethyl-phenylamino)-methylene]-1,3-dihydro-indol-2-one
5-Fluoro-3-[(4-morpholin-4-ylmethyl-phenylamino)-methylene]-1,3-dihydro-indol-2-one
6-Fluoro-3-[(4-morpholin-4-ylmethyl-phenylamino)-methylene]-1,3-dihydro-indol-2-one
4-Methyl-3-{[4-(3-morpholin-4-yl-propylamino)-phenylamino]-methylene}-1,3-dihydro-indol-2-one
3-{[4-(3-Morpholin-4-yl-propylamino)-phenylamino]-methylene}-1,3-dihydro-indol-2-one
6-Fluoro-3-{[4-(3-morpholin-4-yl-propylamino)-phenylamino]-methylene}-1,3-dihydro-indol-2-one
5-Chloro-3-{[4-(3-morpholin-4-yl-propylamino)-phenylamino]-methylene}-1,3-dihydro-indol-2-one
5-Fluoro-3-{[4-(3-morpholin-4-yl-propylamino)-phenylamino]-methylene}-1,3-dihydro-indol-2-one
4-Fluoro-3-{[4-(3-morpholin-4-yl-propylamino)-phenylamino]-methylene}-1,3-dihydro-indol-2-one
3-({4-[3-(4-Methyl-piperazin-1-yl)-propylamino]-phenylamino}-methylene)-1,3-dihydro-indol-2-one
4-Methyl-3-({4-[3-(4-methyl-piperazin-1-yl)-propylamino]-phenylamino}-methylene)-1,3-dihydro-indol-2-one
6-Fluoro-3-({4-[3-(4-methyl-piperazin-1-yl)-propylamino]-phenylamino}-methylene)-1,3-dihydro-indol-2-one
3-({4-[3-(3-Fluoro-pyrrolidin-1-yl)-propoxy]-phenylamino}-methylene)-1,3-dihydro-indol-2-one
3-{[4-(2-morpholin-4-yl-ethyl)-phenylamino]-methylene}-1,3-dihydro-indol-2-one
5-Chloro-3-{[4-(2-morpholin-4-yl-ethyl)-phenylamino]-methylene}-1,3-dihydro-indol-2-one
4-Methyl-3-{[4-(2-morpholin-4-yl-ethyl)-phenylamino]-methylene}-1,3-dihydro-indol-2-one
4-Fluoro-3-{[4-(2-morpholin-4-yl-ethyl)-phenylamino]-methylene}-1,3-dihydro-indol-2-one
5-Fluoro-3-{[4-(2-morpholin-4-yl-ethyl)-phenylamino]-methylene}-1,3-dihydro-indol-2-one
6-Fluoro-3-{[4-(2-morpholin-4-yl-ethyl)-phenylamino]-methylene}-1,3-dihydro-indol-2-one
3-{[4-(4-Morpholin-4-yl-butyl)-phenylamino]-methylene}-1,3-dihydro-indol-2-one
5-Chloro-3-{[4-(4-morpholin-4-yl-butyl)-phenylamino]-methylene}-1,3-dihydro-indol-2-one
4-Methyl-3-{[4-(4-morpholin-4-yl-butyl)-phenylamino]-methylene}-1,3-dihydro-indol-2-one
4-Fluoro-3-{[4-(4-morpholin-4-yl-butyl)-phenylamino]-methylene}-1,3-dihydro-indol-2-one
5-Fluoro-3-{[4-(4-morpholin-4-yl-butyl)-phenylamino]-methylene}-1,3-dihydro-indol-2-one
6-Fluoro-3-{[4-(4-morpholin-4-yl-butyl)-phenylamino]-methylene}-1,3-dihydro-indol-2-one
3-{[4-(4-Piperidin-1-yl-butyl)-phenylamino]-methylene}-1,3-dihydro-indol-2-one
5-Chloro-3-{[4-(4-piperidin-1-yl-butyl)-phenylamino]-methylene}-1,3-dihydro-indol-2-one
4-Methyl-3-{[4-(4-piperidin-1-yl-butyl)-phenylamino]-methylene}-1,3-dihydro-indol-2-one
4-Fluoro-3-{[4-(4-piperidin-1-yl-butyl)-phenylamino]-methylene}-1,3-dihydro-indol-2-one
5-Fluoro-3-{[4-(4-piperidin-1-yl-butyl)-phenylamino]-methylene}-1,3-dihydro-indol-2-one
6-Fluoro-3-{[4-(4-piperidin-1-yl-butyl)-phenylamino]-methylene}-1,3-dihydro-indol-2-one Furthermore, the compounds listed below may be synthesized in accordance with the working examples, using the appropriate substitutions and/or other methods known in the art and similarly will have utility in the method of the present invention.

3-[(4-Pyrrolidin-1-yl-phenylamino)-methylene]-1,3-dihydro-indol-2-one
3-({4-[(2-Methoxy-ethyl)-methyl-amino]-phenylamino}-methylene)-1,3-dihydro-indol-2-one
3-{[4-(3,6-Dihydro-2H-pyridin-1-yl)-phenylamino]-methylene}-1,3-dihydro-indol-2-one
3-{[4-(3-Methyl-piperidin-1-yl)-phenylamino]-methylene}-1,3-dihydro-indol-2-one
3-{[4-(4-Methyl-piperidin-1-yl)-phenylamino]-methylene}-1,3-dihydro-indol-2-one
3-[(4-Azepan-1-yl-phenylamino)-methylene]-1,3-dihydro-indol-2-one
3-{[4-(3-Oxo-piperazin-1-yl)-phenylamino]-methylene}-1,3-dihydro-indol-2-one
3-[(4-Dipropylamino-phenylamino)-methylene]-1,3-dihydro-indol-2-one
3-{[4-(Butyl-ethyl-amino)-phenylamino]-methylene}-1,3-dihydro-indol-2-one 3-({4-[Ethyl-(2-methoxy-ethyl)-amino]-phenylamino}-methylene)-1,3-dihydro-indol-2-one
3-[(4-Thiomorpholin-4-yl-phenylamino)-methylene]-1,3-dihydro-indol-2-one
3-{[4-(Cyclopropylmethyl-propyl-amino)-phenylamino]-methylene}-1,3-dihydro-indol-2-one
3-[(4-Azocan-1-yl-phenylamino)-methylene]-1,3-dihydro-indol-2-one
3-{[4-(3,5-Dimethyl-piperidin-1-yl)-phenylamino]-methylene}-1,3-dihydro-indol-2-one
4-{4-[(2-Oxo-1,2-dihydro-indol-3-ylidenemethyl)-amino]-phenyl}-piperazine-1-carbaldehyde
3-{[4-(5-Oxo-[1,4]diazepan-1-yl)-phenylamino]-methylene}-1,3-dihydro-indol-2-one
3-{[4-(4-Ethyl-piperazin-1-yl)-phenylamino]-methylene}-1,3-dihydro-indol-2-one
3-{[4-(3-Dimethylamino-pyrrolidin-1-yl)-phenylamino]-methylene}-1,3-dihydro-indol-2-one
3-{[4-(Butyl-propyl-amino)-phenylamino]-methylene}-1,3-dihydro-indol-2-one
3-({4-[(2-Methoxy-ethyl)-propyl-amino]-phenylamino}-methylene)-1,3-dihydro-indol-2-one
3-{[4-(1,3-Dihydro-isoindol-2-yl)-phenylamino]-methylene}-1,3-dihydro-indol-2-one
1-{4-[(2-Oxo-1,2-dihydro-indol-3-ylidenemethyl)-amino]-phenyl}-piperidine-3-carboxylic acid amide
1-{4-[(2-Oxo-1,2-dihydro-indol-3-ylidenemethyl)-amino]-phenyl}-piperidine-4-carboxylic acid amide
3-{[4-(4-Acetyl-piperazin-1-yl)-phenylamino]-methylene}-1,3-dihydro-indol-2-one N-(1-{4-[(2-Oxo-1,2-dihydro-indol-3-ylidenemethyl)-amino]-phenyl}-pyrrolidin-3-yl)-acetamide
3-{[4-(4-Isopropyl-piperazin-1-yl)-phenylamino]-methylene}-1,3-dihydro-indol-2-one
3-{[4-(Octahydro-isoquinolin-2-yl)-phenylamino]-methylene}-1,3-dihydro-indol-2-one
3-{[4-(Octahydro-isoquinolin-2-yl)-phenylamino]-methylene}-1,3-dihydro-indol-2-one
3-{[4-(4-Butyl-piperazin-1-yl)-phenylamino]-methylene}-1,3-dihydro-indol-2-one
3-{[4-(4-sec-Butyl-piperazin-1-yl)-phenylamino]-methylene}-1,3-dihydro-indol-2-one
3-{[4-(3-Diethylamino-pyrrolidin-1-yl)-phenylamino]-methylene}-1,3-dihydro-indol-2-one
3-{[4-(1,4-Dioxa-8-aza-spiro[4.5]dec-8-yl)-phenylamino]-methylene}-1,3-dihydro-indol-2-one
3-({4-[4-(2-Methoxy-ethyl)-piperazin-1-yl]-phenylamino}-methylene)-1,3-dihydro-indol-2-one
3-{[4-(3-Pyridin-2-yl-pyrrolidin-1-yl)-phenylamino]-methylene}-1,3-dihydro-indol-2-one
3-{[4-(3-Pyridin-4-yl-pyrrolidin-1-yl)-phenylamino]-methylene}-1,3-dihydro-indol-2-one
3-{[4-(3-Methanesulfonyl-pyrrolidin-1-yl)-phenylamino]-methylene}-1,3-dihydro-indol-2-one
3-{[4-(4-Propyl-piperidin-1-yl)-phenylamino]-methylene}-1,3-dihydro-indol-2-one
3-{[4-(Methyl-pyridin-3-ylmethyl-amino)-phenylamino]-methylene}-1,3-dihydro-indol-2-one
3-({4-[Methyl-(2-pyridin-2-yl-ethyl)-amino]-phenylamino}-methylene)-1,3-dihydro-indol-2-one
3-{[4-(4-Pyrimidin-2-yl-piperazin-1-yl)-phenylamino]-methylene}-1,3-dihydro-indol-2-one
3-{[4-(2,3,5,6-Tetrahydro-[1,2']bipyrazinyl-4-yl)-phenylamino]-methylene}-1,3-dihydro-indol-2-one
3-{[4-([1,3]Dioxolan-2-ylmethyl-methyl-amino)-phenylamino]-methylene}-1,3-dihydro-indol-2-one
3-({4-[(2-[1,3]Dioxolan-2-yl-ethyl)-methyl-amino]-phenylamino}-methylene)-1,3-dihydro-indol-2-one
3-{[4-(2-Methoxy-ethylamino)-phenylamino]-methylene}-1,3-dihydro-indol-2-one
3-{[4-(Tetrahydro-pyran-4-ylamino)-phenylamino]-methylene}-1,3-dihydro-indol-2-one
3-{[4-(3-Dimethylamino-propylamino)-phenylamino]-methylene}-1,3-dihydro-indol-2-one
3-{[4-(1-Methoxymethyl-propylamino)-phenylamino]-methylene}-1,3-dihydro-indol-2-one
3-{[4-(2-Pyridin-2-yl-ethylamino)-phenylamino]-methylene}-1,3-dihydro-indol-2-one
3-{[4-(2-Pyridin-3-yl-ethylamino)-phenylamino]-methylene}-1,3-dihydro-indol-2-one
3-({4-[(Pyridin-3-ylmethyl)-amino]-phenylamino}-methylene)-1,3-dihydro-indol-2-one
3-{[4-(2-Methoxy-1-methyl-ethylamino)-phenylamino]-methylene}-1,3-dihydro-indol-2-one
3-{[4-(3-Diethylamino-propylamino)-phenylamino]-methylene}-1,3-dihydro-indol-2-one
3-{[4-(2-Diisopropylamino-ethylamino)-phenylamino]-methylene}-1,3-dihydro-indol-2-one
3-({4-[(5-Methyl-pyrazin-2-ylmethyl)-amino]-phenylamino}-methylene)-1,3-dihydro-indol-2-one
3-{[4-(1,2,2,6,6-Pentamethyl-piperidin-4-ylamino)-phenylamino]-methylene}-1,3-dihydro-indol-2-one
3-({4-[(Tetrahydro-pyran-4-ylmethyl)-amino]-phenylamino}-methylene)-1,3-dihydro-indol-2-one
3-{[4-(2-Hydroxy-ethylamino)-phenylamino]-methylene}-1,3-dihydro-indol-2-one
3-{[4-(2-Diethylamino-1-methyl-ethylamino)-phenylamino]-methylene}-1,3-dihydro-indol-2-one
4-Methyl-3-[(4-pyrrolidin-1-yl-phenylamino)-methylene]-1,3-dihydro-indol-2-one
1-{4-[(4-Methyl-2-oxo-1,2-dihydro-indol-3-ylidenemethyl)-amino]-phenyl-piperidine-4-carboxylic acid methyl ester
3-({4-[(2-Methoxy-ethyl)-methyl-amino]-phenylamino-methylene)-4-methyl-1,3-dihydro-indol-2-one
3-{[4-(3,6-Dihydro-2H-pyridin-1-yl)-phenylamino]-methylene}-4-methyl-1,3-dihydro-indol-2-one
4-Methyl-3-{[4-(3-methyl-piperidin-1-yl)-phenylamino]-methylene}-1,3-dihydro-indol-2-one
4-Methyl-3-{[4-(4-methyl-piperidin-1-yl)-phenylamino]-methylene}-1,3-dihydro-indol-2-one
3-[(4-Azepan-1-yl-phenylamino)-methylene]-4-methyl-1,3-dihydro-indol-2-one
4-Methyl-3-{[4-(4-methyl-piperazin-1-yl)-phenylamino]-methylene}-1,3-dihydro-indol-2-one
3-[(4-Dipropylamino-phenylamino)-methylene]-4-methyl-1,3-dihydro-indol-2-one
3-{[4-(Butyl-ethyl-amino)-phenylamino]-methylene}-4-methyl-1,3-dihydro-indol-2-one
3-({4-[Ethyl-(2-methoxy-ethyl)-amino]-phenylamino-methylene)-4-methyl-1,3-dihydro-indol-2-one
4-Methyl-3-[(4-thiomorpholin-4-yl-phenylamino)-methylene]-1,3-dihydro-indol-2-one
3-{[4-(Cyclopropylmethyl-propyl-amino)-phenylamino]-methylene}-4-methyl-1,3-dihydro-indol-2-one
3-[(4-Azocan-1-yl-phenylamino)-methylene]-4-methyl-1,3-dihydro-indol-2-one
4-{4-[(4-Methyl-2-oxo-1,2-dihydro-indol-3-ylidenemethyl)-amino]-phenyl}-piperazine-1-carbaldehyde
3-{[4-(4-Ethyl-piperazin-1-yl)-phenylamino]-methylene}-4-methyl-1,3-dihydro-indol-2-one
3-{[4-(3-Dimethylamino-pyrrolidin-1-yl)-phenylamino]-methylene}-4-methyl-1,3-dihydro-indol-2-one 3-{[4-(2,6-Dimethyl-morpholin-4-yl)-phenylamino]-methylene}-4-methyl-1,3-dihydro-indol-2-one
3-{([4-(Butyl-propyl-amino)-phenylamino]-methylene}-4-methyl-1,3-dihydro-indol-2-one
3-({4-[(2-Methoxy-ethyl)-propyl-amino]-phenylamino}-methylene)-4-methyl-1,3-dihydro-indol-2-one
1-{4-[(4-Methyl-2-oxo-1,2-dihydro-indol-3-ylidenemethyl)-amino]-phenyl}-piperidine-3-carboxylic acid amide
N-(1-{4-[(4-Methyl-2-oxo-1,2-dihydro-indol-3-ylidenemethyl)-amino]-phenyl}-pyrrolidin-3-yl)-acetamide
3-{[4-(4-Isopropyl-piperazin-1-yl)-phenylamino]-methylene}-4-methyl-1,3-dihydro-indol-2-one
4-Methyl-3-{[4-(octahydro-isoquinolin-2-yl)-phenylamino]-methylene-1,3-dihydro-indol-2-one
4-Methyl-3-{[4-(octahydro-isoquinolin-2-yl)-phenylamino]-methylene-1,3-dihydro-indol-2-one
3-{[4-(4-Butyl-piperazin-1-yl)-phenylamino]-methylene}-4-methyl-1,3-dihydro-indol-2-one
3-{[4-(4-sec-Butyl-piperazin-1-yl)-phenylamino]-methylene}-4-methyl-1,3-dihydro-indol-2-one
3-{[4-(3-Diethylamino-pyrrolidin-1-yl)-phenylamino]-methylene}-4-methyl-1,3-dihydro-indol-2-one
3-{[4-(1,4-Dioxa-8-aza-spiro[4.5]dec-8-yl)-phenylamino]-methylene}-4-methyl-1,3-dihydro-indol-2-one
3-({4-[4-(2-Methoxy-ethyl)-piperazin-1-yl]-phenylamino}-methylene)-4-methyl-1,3-dihydro-indol-2-one
4-Methyl-3-{([4-(3-pyridin-2-yl-pyrrolidin-1-yl)-phenylamino]-methylene)-1,3-dihydro-indol-2-one
4-Methyl-3-{[4-(3-pyridin-4-yl-pyrrolidin-1-yl)-phenylamino]-methylene}-1,3-dihydro-indol-2-one
3-{[4-(3-Methanesulfonyl-pyrrolidin-1-yl)-phenylamino]-methylene}-4-methyl-1,3-dihydro-indol-2-one
4-Methyl-3-{[4-(methyl-pyridin-3-ylmethyl-amino)-phenylamino]-methylene}-1,3-dihydro-indol-2-one
3-({4-[(2-[1,3]Dioxolan-2-yl-ethyl)-methyl-amino]-phenylamino}-methylene)-4-methyl-1,3-dihydro-indol-2-one
4-Methyl-3-{[4-(tetrahydro-pyran-4-ylamino)-phenylamino]-methylene}-1,3-dihydro-indol-2-one
4-Fluoro-3-[(4-pyrrolidin-1-yl-phenylamino)-methylene]-1,3-dihydro-indol-2-one
3-[(4-Diethylamino-phenylamino)-methylene]-4-fluoro-1,3-dihydro-indol-2-one
4-Fluoro-3-({4-[(2-methoxy-ethyl)-methyl-amino]-phenylamino}-methylene)-1,3-dihydro-indol-2-one
3-{[4-(3,6-Dihydro-2H-pyridin-1-yl)-phenylamino]-methylene}-4-fluoro-1,3-dihydro-indol-2-one
4-Fluoro-3-[(4-morpholin-4-yl-phenylamino)-methylene]-1,3-dihydro-indol-2-one
4-Fluoro-3-{[4-(3-methyl-piperidin-1-yl)-phenylamino]-methylene}-1,3-dihydro-indol-2-one
4-Fluoro-3-{[4-(4-methyl-piperidin-1-yl)-phenylamino]-methylene}-1,3-dihydro-indol-2-one
4-Fluoro-3-{[4-(4-methyl-piperazin-1-yl)-phenylamino]-methylene}-1,3-dihydro-indol-2-one
3-{[4-(Butyl-ethyl-amino)-phenylamino]-methylene}-4-fluoro-1,3-dihydro-indol-2-one
3-({4-[Ethyl-(2-methoxy-ethyl)-amino]-phenylamino}-methylene)-4-fluoro-1,3-dihydro-indol-2-one
4-Fluoro-3-[(4-thiomorpholin-4-yl-phenylamino)-methylene]-1,3-dihydro-indol-2-one
3-{[4-(Cyclopropylmethyl-propyl-amino)-phenylamino]-methylene}-4-fluoro-1,3-dihydro-indol-2-one
3-{[4-(3,5-Dimethyl-piperidin-1-yl)-phenylamino]-methylene}-4-fluoro-1,3-dihydro-indol-2-one
3-{[4-(3,5-Dimethyl-piperazin-1-yl)-phenylamino]-methylene}-4-fluoro-1,3-dihydro-indol-2-one
4-Fluoro-3-{([4-(4-methyl-[1,4]diazepan-1-yl)-phenylamino]-methylene)-1,3-dihydro-indol-2-one
3-{[4-(4-Ethyl-piperazin-1-yl)-phenylamino]-methylene}-4-fluoro-1,3-dihydro-indol-2-one
3-{[4-(3-Dimethylamino-pyrrolidin-1-yl)-phenylamino]-methylene}-4-fluoro-1,3-dihydro-indol-2-one
3-{[4-(2,6-Dimethyl-morpholin-4-yl)-phenylamino]-methylene}-4-fluoro-1,3-dihydro-indol-2-one
3-{[4-(2,6-Dimethyl-morpholin-4-yl)-phenylamino]-methylene}-4-fluoro-1,3-dihydro-indol-2-one
3-{[4-(Butyl-propyl-amino)-phenylamino]-methylene}-4-fluoro-1,3-dihydro-indol-2-one
4-Fluoro-3-((4-[(2-methoxy-ethyl)-propyl-amino]-phenylamino}-methylene)-1,3-dihydro-indol-2-one
3-{[4-(1,3-Dihydro-isoindol-2-yl)-phenylamino]-methylene}-4-fluoro-1,3-dihydro-indol-2-one
1-{4-[(4-Fluoro-2-oxo-1,2-dihydro-indol-3-ylidenemethyl)-amino]-phenyl}-piperidine-3-carboxylic acid amide
1-{4-[(4-Fluoro-2-oxo-1,2-dihydro-indol-3-ylidenemethyl)-amino]-phenyl}-piperidine-4-carboxylic acid amide
N-(1-{4-[(4-Fluoro-2-oxo-1,2-dihydro-indol-3-ylidenemethyl)-amino]-phenyl}-pyrrolidin-3-yl)-acetamide
4-Fluoro-3-{[4-(4-isopropyl-piperazin-1-yl)-phenylamino]-methylene}-1,3-dihydro-indol-2-one
4-Fluoro-3-{[4-(octahydro-isoquinolin-2-yl)-phenylamino]-methylene-1,3-dihydro-indol-2-one
4-Fluoro-3-{[4-(octahydro-isoquinolin-2-yl)-phenylamino]-methylene-1,3-dihydro-indol-2-one
3-{[4-(4-Butyl-piperazin-1-yl)-phenylamino]-methylene}-4-fluoro-1,3-dihydro-indol-2-one
3-{[4-(4-sec-Butyl-piperazin-1-yl)-phenylamino]-methylene}-4-fluoro-1,3-dihydro-indol-2-one
3-{[4-(3-Diethylamino-pyrrolidin-1-yl)-phenylamino]-methylene}-4-fluoro-1,3-dihydro-indol-2-one
3-{[4-(1,4-Dioxa-8-aza-spiro[4.5]dec-8-yl)-phenylamino]-methylene}-4-fluoro-1,3-dihydro-indol-2-one
4-Fluoro-3-({4-[4-(2-methoxy-ethyl)-piperazin-1-yl]-phenylamino}-methylene)-1,3-dihydro-indol-2-one
4-Fluoro-3-{[4-(3-pyridin-2-yl-pyrrolidin-1-yl)-phenylamino]-methylene}-1,3-dihydro-indol-2-one
4-Fluoro-3-{[4-(3-pyridin-4-yl-pyrrolidin-1-yl)-phenylamino]-methylene}-1,3-dihydro-indol-2-one
4-Fluoro-3-{[4-(4-propyl-piperidin-1-yl)-phenylamino]-methylene}-1,3-dihydro-indol-2-one
4-Fluoro-3-{[4-(methyl-pyridin-3-ylmethyl-amino)-phenylamino]-methylene}-1,3-dihydro-indol-2-one
4-Fluoro-3-({4-[methyl-(2-pyridin-2-yl-ethyl)-amino]-phenylamino}-methylene)-1,3-dihydro-indol-2-one
4-Fluoro-3-{[4-(4-pyrimidin-2-yl-piperazin-1-yl)-phenylamino]-methylene}-1,3-dihydro-indol-2-one
3-{[4-([1,3]Dioxolan-2-ylmethyl-methyl-amino)-phenylamino]-methylene}-4-fluoro-1,3-dihydro-indol-2-one
3-(4-[(2-[1,3]Dioxolan-2-yl-ethyl)-methyl-amino]-phenylamino-methylene)-4-fuoro-1,3-dihydro-indol-2-one
4-Fluoro-3-{[4-(2-methoxy-ethylamino)-phenylamino]-methylene}-1,3-dihydro-indol-2-one
4-Fluoro-3-({4-[(tetrahydro-furan-2-ylmethyl)-amino]-phenylamino}-methylene)-1,3-dihydro-indol-2-one
4-Fluoro-3-{[4-(tetrahydro-pyran-4-ylamino)-phenylamino]-methylene}-1,3-dihydro-indol-2-one
3-{[4-(3-Dimethylamino-propylamino)-phenylamino]-methylene}-4-fluoro-1,3-dihydro-indol-2-one
4-Fluoro-3-{[4-(1-methoxymethyl-propylamino)-phenylamino]-methylene}-1,3-dihydro-indol-2-one
4-Fluoro-3-{[4-(2-piperidin-1-yl-ethylamino)-phenylamino]-methylene}-1,3-dihydro-indol-2-one 3-{[4-(3-Diethylamino-propylamino)-phenylamino]-methylene}-4-fluoro-1,3-dihydro-indol-2-one
4-Fluoro-3-{[4-(1,2,2,6,6-pentamethyl-piperidin-4-ylamino)-phenylamino]-methylene}-1,3-dihydro-indol-2-one
4-Fluoro-3-({4-[(tetrahydro-pyran-4-ylmethyl)-amino]-phenylamino}-methylene)-1,3-dihydro-indol-2-one
3-{[4-(2-Diethylamino-1-methyl-ethylamino)-phenylamino]-methylene}-4-fluoro-1,3-dihydro-indol-2-one
5-Fluoro-3-[(4-pyrrolidin-1-yl-phenylamino)-methylene]-1,3-dihydro-indol-2-one
3-[(4-Diethylamino-phenylamino)-methylene]-5-fluoro-1,3-dihydro-indol-2-one
1-{4-[(5-Fluoro-2-oxo-1,2-dihydro-indol-3-ylidenemethyl)-amino]-phenyl-piperidine-4-carboxylic acid methyl ester
5-Fluoro-3-({4-[(2-methoxy-ethyl)-methyl-amino]-phenylamino}-methylene)-1,3-dihydro-indol-2-one
5-Fluoro-3-{[4-(4-methyl-piperidin-1-yl)-phenylamino]-methylene}-1,3-dihydro-indol-2-one
3-[(4-Azepan-1-yl-phenylamino)-methylene]-5-fluoro-1,3-dihydro-indol-2-one
5-Fluoro-3-{[4-(3-oxo-piperazin-1-yl)-phenylamino]-methylene}-1,3-dihydro-indol-2-one
3-[(4-Dipropylamino-phenylamino)-methylene]-5-fluoro-1,3-dihydro-indol-2-one
3-{[4-(Butyl-ethyl-amino)-phenylamino]-methylene}-5-fluoro-1,3-dihydro-indol-2-one
3-({4-[Ethyl-(2-methoxy-ethyl)-amino]-phenylamino}-methylene)-5-fluoro-1,3-dihydro-indol-2-one
5-Fluoro-3-[(4-thiomorpholin-4-yl-phenylamino)-methylene]-1,3-dihydro-indol-2-one
3-{[4-(Cyclopropylmethyl-propyl-amino)-phenylamino]-methylene}-5-fluoro-1,3-dihydro-indol-2-one
3-[(4-Azocan-1-yl-phenylamino)-methylene]-5-fluoro-1,3-dihydro-indol-2-one
3-{[4-(3,5-Dimethyl-piperidin-1-yl)-phenylamino]-methylene}-5-fluoro-1,3-dihydro-indol-2-one
4-{4-[(5-Fluoro-2-oxo-1,2-dihydro-indol-3-ylidenemethyl)-amino]-phenyl}-piperazine-1-carbaldehyde
3-{[4-(3,5-Dimethyl-piperazin-1-yl)-phenylamino]-methylene}-5-fluoro-1,3-dihydro-indol-2-one
5-Fluoro-3-{[4-(4-methyl-[1,4]diazepan-1-yl)-phenylamino]-methylene}-1,3-dihydro-indol-2-one
3-{[4-(4-Ethyl-piperazin-1-yl)-phenylamino]-methylene}-5-fluoro-1,3-dihydro-indol-2-one
3-{[4-(2,6-Dimethyl-morpholin-4-yl)-phenylamino]-methylene}-5-fluoro-1,3-dihydro-indol-2-one
3-{[4-(Butyl-propyl-amino)-phenylamino]-methylene}-5-fluoro-1,3-dihydro-indol-2-one
5-Fluoro-3-({4-[(2-methoxy-ethyl)-propyl-amino]-phenylamino}-methylene)-1,3-dihydro-indol-2-one
3-{[4-(1,3-Dihydro-isoindol-2-yl)-phenylamino]-methylene}-5-fluoro-1,3-dihydro-indol-2-one
N-(1-{4-[(5-Fluoro-2-oxo-1,2-dihydro-indol-3-ylidenemethyl)-amino]-phenyl}-pyrrolidin-3-yl)-acetamide
5-Fluoro-3-{[4-(4-isopropyl-piperazin-1-yl)-phenylamino]-methylene}-1,3-dihydro-indol-2-one
5-Fluoro-3-{[4-(octahydro-isoquinolin-2-yl)-phenylamino]-methylene-1,3-dihydro-indol-2-one
5-Fluoro-3-{[4-(octahydro-isoquinolin-2-yl)-phenylamino]-methylene-1,3-dihydro-indol-2-one
3-{[4-(4-Butyl-piperazin-1-yl)-phenylamino]-methylene}-5-fluoro-1,3-dihydro-indol-2-one
3-{[4-(4-sec-Butyl-piperazin-1-yl)-phenylamino]-methylene}-5-fluoro-1,3-dihydro-indol-2-one
3-{[4-(3-Diethylamino-pyrrolidin-1-yl)-phenylamino]-methylene}-5-fluoro-1,3-dihydro-indol-2-one
3-{[4-(1,4-Dioxa-8-aza-spiro[4.5]dec-8-yl)-phenylamino]-methylene}-5-fluoro-1,3-dihydro-indol-2-one
5-Fluoro-3-({4-[4-(2-methoxy-ethyl)-piperazin-1-yl]-phenylamino}-methylene)-1,3-dihydro-indol-2-one
5-Fluoro-3-{[4-(3-pyridin-2-yl-pyrrolidin-1-yl)-phenylamino]-methylene}-1,3-dihydro-indol-2-one
5-Fluoro-3-{[4-(3-pyridin-4-yl-pyrrolidin-1-yl)-phenylamino]-methylene}-1,3-dihydro-indol-2-one
5-Fluoro-3-{[4-(4-propyl-piperidin-1-yl)-phenylamino]-methylene}-1,3-dihydro-indol-2-one
5-Fluoro-3-{[4-(methyl-pyridin-3-ylmethyl-amino)-phenylamino]-methylene}-1,3-dihydro-indol-2-one
5-Fluoro-3-({4-[methyl-(2-pyridin-2-yl-ethyl)-amino]-phenylamino}-methylene)-1,3-dihydro-indol-2-one
5-Fluoro-3-{[4-(4-pyrimidin-2-yl-piperazin-1-yl)-phenylamino]-methylene}-1,3-dihydro-indol-2-one
5-Fluoro-3-{[4-(2,3,5,6-tetrahydro-[1,2']bipyrazinyl-4-yl)-phenylamino]-methylene}-1,3-dihydro-indol-2-one
3-{[4-([1,3]Dioxolan-2-ylmethyl-methyl-amino)-phenylamino]-methylene-5-fluoro-1,3-dihydro-indol-2-one
3-({4-[(2-[1,3]Dioxolan-2-yl-ethyl)-methyl-amino]-phenylamino}-methylene)-5-fluoro-1,3-dihydro-indol-2-one
N-(1-{4-[(5-Fluoro-2-oxo-1,2-dihydro-indol-3-ylidenemethyl)-amino]-phenyl}-pyrrolidin-3-yl)-N-methyl-acetamide
5-Fluoro-3-{[4-(2-methoxy-ethylamino)-phenylamino]-methylene}-1,3-dihydro-indol-2-one
5-Fluoro-3-({4-[(tetrahydro-furan-2-ylmethyl)-amino]-phenylamino}-methylene)-1,3-dihydro-indol-2-one
5-Fluoro-3-{[4-(tetrahydro-pyran-4-ylamino)-phenylamino]-methylene}-1,3-dihydro-indol-2-one
3-{[4-(3-Dimethylamino-propylamino)-phenylamino]-methylene}-5-fluoro-1,3-dihydro-indol-2-one
3-{[4-(2-Dimethylamino-1-methyl-ethylamino)-phenylamino]-methylene}-5-fluoro-1,3-dihydro-indol-2-one
5-Fluoro-3-{[4-(2-pyridin-2-yl-ethylamino)-phenylamino]-methylene}-1,3-dihydro-indol-2-one
5-Fluoro-3-{[4-(2-pyridin-3-yl-ethylamino)-phenylamino]-methylene}-1,3-dihydro-indol-2-one
5-Fluoro-3-{[4-(2-morpholin-4-yl-ethylamino)-phenylamino]-methylene}-1,3-dihydro-indol-2-one
5-Fluoro-3-({4-[(pyridin-2-ylmethyl)-amino]-phenylamino}-methylene)-1,3-dihydro-indol-2-one
5-Fluoro-3-({4-[(pyridin-3-ylmethyl)-amino]-phenylamino-methylene)-1,3-dihydro-indol-2-one
5-Fluoro-3-{[4-(2-methoxy-1-methyl-ethylamino)-phenylamino]-methylene}-1,3-dihydro-indol-2-one
3-{[4-(3-Diethylamino-propylamino)-phenylamino]-methylene}-5-fluoro-1,3-dihydro-indol-2-one
3-{[4-(2-Diisopropylamino-ethylamino)-phenylamino]-methylene}-5-fluoro-1,3-dihydro-indol-2-one
5-Fluoro-3-{[4-(1,2,2,6,6-pentamethyl-piperidin-4-ylamino)-phenylamino]-methylene}-1,3-dihydro-indol-2-one
5-Fluoro-3-({4-[(tetrahydro-pyran-4-ylmethyl)-amino]-phenylamino}-methylene)-1,3-dihydro-indol-2-one
6-Fluoro-3-[(4-pyrrolidin-1-yl-phenylamino)-methylene]-1,3-dihydro-indol-2-one
3-[(4-Diethylamino-phenylamino)-methylene]-6-fluoro-1,3-dihydro-indol-2-one
6-Fluoro-3-({4-[(2-methoxy-ethyl)-methyl-amino]-phenylamino}-methylene)-1,3-dihydro-indol-2-one
3-{[4-(3,6-Dihydro-2H-pyridin-1-yl)-phenylamino]-methylene}-6-fluoro-1,3-dihydro-indol-2-one
6-Fluoro-3-{[4-(3-methyl-piperidin-1-yl)-phenylamino]-methylene}-1,3-dihydro-indol-2-one 6-Fluoro-3-{[4-(4-methyl-piperidin-1-yl)-phenylamino]-methylene}-1,3-dihydro-indol-2-one
3-[(4-Azepan-1-yl-phenylamino)-methylene]-6-fluoro-1,3-dihydro-indol-2-one
3-[(4-Dipropylamino-phenylamino)-methylene]-6-fluoro-1,3-dihydro-indol-2-one
3-{[4-(Butyl-ethyl-amino)-phenylamino]-methylene}-6-fluoro-1,3-dihydro-indol-2-one
3-({4-[Ethyl-(2-methoxy-ethyl)-amino]-phenylamino}-methylene)-6-fluoro-1,3-dihydro-indol-2-one
6-Fluoro-3-[(4-thiomorpholin-4-yl-phenylamino)-methylene]-1,3-dihydro-indol-2-one
3-{[4-(Cyclopropylmethyl-propyl-amino)-phenylamino]-methylene}-6-fluoro-1,3-dihydro-indol-2-one
3-[(4-Azocan-1-yl-phenylamino)-methylene]-6-fluoro-1,3-dihydro-indol-2-one
3-{[4-(3,5-Dimethyl-piperidin-1-yl)-phenylamino]-methylene}-6-fluoro-1,3-dihydro-indol-2-one
4-{4-[(6-Fluoro-2-oxo-1,2-dihydro-indol-3-ylidenemethyl)-amino]-phenyl}-piperazine-1-carbaldehyde
3-{[4-(3,5-Dimethyl-piperazin-1-yl)-phenylamino]-methylene}-6-fluoro-1,3-dihydro-indol-2-one
3-{[4-(4-Ethyl-piperazin-1-yl)-phenylamino]-methylene}-6-fluoro-1,3-dihydro-indol-2-one
3-{[4-(2,6-Dimethyl-morpholin-4-yl)-phenylamino]-methylene}-6-fluoro-1,3-dihydro-indol-2-one
3-{[4-(2,6-Dimethyl-morpholin-4-yl)-phenylamino]-methylene}-6-fluoro-1,3-dihydro-indol-2-one
3-{[4-(Butyl-propyl-amino)-phenylamino]-methylene}-6-fluoro-1,3-dihydro-indol-2-one
6-Fluoro-3-({4-[(2-methoxy-ethyl)-propyl-amino]-phenylamino-methylene)-1,3-dihydro-indol-2-one
3-{[4-(1,3-Dihydro-isoindol-2-yl)-phenylamino]-methylene}-6-fluoro-1,3-dihydro-indol-2-one
1-{4-[(6-Fluoro-2-oxo-1,2-dihydro-indol-3-ylidenemethyl)-amino]-phenyl}-piperidine-4-carboxylic acid amide
N-(1-{4-[(6-Fluoro-2-oxo-1,2-dihydro-indol-3-ylidenemethyl)-amino]-phenyl}-pyrrolidin-3-yl)-acetamide
6-Fluoro-3-{[4-(4-isopropyl-piperazin-1-yl)-phenylamino]-methylene}-1,3-dihydro-indol-2-one
6-Fluoro-3-{[4-(octahydro-isoquinolin-2-yl)-phenylamino]-methylene-1,3-dihydro-indol-2-one
6-Fluoro-3-{[4-(octahydro-isoquinolin-2-yl)-phenylamino]-methylene-1,3-dihydro-indol-2-one
3-{[4-(4-sec-Butyl-piperazin-1-yl)-phenylamino]-methylene}-6-fluoro-1,3-dihydro-indol-2-one
3-{[4-(3-Diethylamino-pyrrolidin-1-yl)-phenylamino]-methylene}-6-fluoro-1,3-dihydro-indol-2-one
3-{[4-(1,4-Dioxa-8-aza-spiro[4.5]dec-8-yl)-phenylamino]-methylene}-6-fluoro-1,3-dihydro-indol-2-one
6-Fluoro-3-({4-[4-(2-methoxy-ethyl)-piperazin-1-yl]-phenylamino}-methylene)-1,3-dihydro-indol-2-one
6-Fluoro-3-{[4-(3-pyridin-2-yl-pyrrolidin-1-yl)-phenylamino]-methylene}-1,3-dihydro-indol-2-one
6-Fluoro-3-{[4-(3-pyridin-4-yl-pyrrolidin-1-yl)-phenylamino]-methylene}-1,3-dihydro-indol-2-one
6-Fluoro-3-{[4-(3-methanesulfonyl-pyrrolidin-1-yl)-phenylamino]-methylene}-1,3-dihydro-indol-2-one
6-Fluoro-3-{[4-(methyl-pyridin-3-ylmethyl-amino)-phenylamino]-methylene}-1,3-dihydro-indol-2-one
6-Fluoro-3-({4-[methyl-(2-pyridin-2-yl-ethyl)-amino]-phenylamino}-methylene)-1,3-dihydro-indol-2-one
6-Fluoro-3-{[4-(4-pyrimidin-2-yl-piperazin-1-yl)-phenylamino]-methylene}-1,3-dihydro-indol-2-one
6-Fluoro-3-{[4-(2,3,5,6-tetrahydro-[1,2']bipyrazinyl-4-yl)-phenylamino]-methylene}-1,3-dihydro-indol-2-one
3-({4-[(2-[1,3]Dioxolan-2-yl-ethyl)-methyl-amino]-phenylamino}-methylene)-6-fluoro-1,3-dihydro-indol-2-one
6-Fluoro-3-({4-[(tetrahydro-furan-2-ylmethyl)-amino]-phenylamino}-methylene)-1,3-dihydro-indol-2-one
3-{[4-(3-Dimethylamino-propylamino)-phenylamino]-methylene-6-fluoro-1,3-dihydro-indol-2-one
3-{[4-(2-Dimethylamino-1-methyl-ethylamino)-phenylamino]-methylene}-6-fluoro-1,3-dihydro-indol-2-one
6-Fluoro-3-{[4-(1-methoxymethyl-propylamino)-phenylamino]-methylene}-1,3-dihydro-indol-2-one
6-Fluoro-3-{[4-(2-pyridin-2-yl-ethylamino)-phenylamino]-methylene}-1,3-dihydro-indol-2-one
6-Fluoro-3-{[4-(2-pyridin-3-yl-ethylamino)-phenylamino]-methylene}-1,3-dihydro-indol-2-one
6-Fluoro-3-{[4-(2-morpholin-4-yl-ethylamino)-phenylamino]-methylene}-1,3-dihydro-indol-2-one
6-Fluoro-3-({4-[(pyridin-3-ylmethyl)-amino]-phenylamino}-methylene)-1,3-dihydro-indol-2-one
6-Fluoro-3-({4-[3-(2-methyl-piperidin-1-yl)-propylamino]-phenylamino}-methylene)-1,3-dihydro-indol-2-one
6-Fluoro-3-{[4-(2-methoxy-1-methyl-ethylamino)-phenylamino]-methylene}-1,3-dihydro-indol-2-one
3-{[4-(2-Diisopropylamino-ethylamino)-phenylamino]-methylene}-6-fluoro-1,3-dihydro-indol-2-one
3-{[4-(1-Benzyl-pyrrolidin-3-ylamino)-phenylamino]-methylene}-6-fluoro-1,3-dihydro-indol-2-one
6-Fluoro-3-({4-[(5-methyl-pyrazin-2-ylmethyl)-amino]-phenylamino}-methylene)-1,3-dihydro-indol-2-one
3-{4-[(6-Fluoro-2-oxo-1,2-dihydro-indol-3-ylidenemethyl)-amino]-phenylamino}-pyrrolidine-1-carboxylic acid tert-butyl ester
6-Fluoro-3-({4-[(tetrahydro-pyran-4-ylmethyl)-amino]-phenylamino}-methylene)-1,3-dihydro-indol-2-one
3-[(3-Fluoro-4-pyrrolidin-1-yl-phenylamino)-methylene]-1,3-dihydro-indol-2-one
3-[(4-Diethylamino-3-fluoro-phenylamino)-methylene]-1,3-dihydro-indol-2-one
1-{2-Fluoro-4-[(2-oxo-1,2-dihydro-indol-3-ylidenemethyl)-amino]-phenyl}-piperidine-4-carboxylic acid methyl ester
3-({3-Fluoro-4-[(2-methoxy-ethyl)-methyl-amino]-phenylamino}-methylene)-1,3-dihydro-indol-2-one
3-{[4-(3,6-Dihydro-2H-pyridin-1-yl)-3-fluoro-phenylamino]-methylene}-1,3-dihydro-indol-2-one
3-[(3-Fluoro-4-morpholin-4-yl-phenylamino)-methylene]-1,3-dihydro-indol-2-one
3-{[3-Fluoro-4-(3-methyl-piperidin-1-yl)-phenylamino]-methylene}-1,3-dihydro-indol-2-one
3-{[3-Fluoro-4-(4-methyl-piperidin-1-yl)-phenylamino]-methylene}-1,3-dihydro-indol-2-one
3-[(4-Azepan-1-yl-3-fluoro-phenylamino)-methylene]-1,3-dihydro-indol-2-one
3-{[3-Fluoro-4-(3-oxo-piperazin-1-yl)-phenylamino]-methylene}-1,3-dihydro-indol-2-one
3-{[3-Fluoro-4-(4-methyl-piperazin-1-yl)-phenylamino]-methylene}-1,3-dihydro-indol-2-one
3-[(4-Dipropylamino-3-fluoro-phenylamino)-methylene]-1,3-dihydro-indol-2-one
3-{[4-(Butyl-ethyl-amino)-3-fluoro-phenylamino]-methylene}-1,3-dihydro-indol-2-one
3-({4-[Ethyl-(2-methoxy-ethyl)-amino]-3-fluoro-phenylamino}-methylene)-1,3-dihydro-indol-2-one
4-{2-Fluoro-4-[(2-oxo-1,2-dihydro-indol-3-ylidenemethyl)-amino]-phenyl}-piperazine-1-carbaldehyde
3-{[3-Fluoro-4-(5-oxo-[1,4]diazepan-1-yl)-phenylamino]-methylene}-1,3-dihydro-indol-2-one 3-{[4-(3,5-Dimethyl-piperazin-1-yl)-3-fluoro-phenylamino]-methylene}-1,3-dihydro-indol-2-one
3-{[4-(3-Dimethylamino-pyrrolidin-1-yl)-3-fluoro-phenylamino]-methylene}-1,3-dihydro-indol-2-one
3-{[4-(2,6-Dimethyl-morpholin-4-yl)-3-fluoro-phenylamino]-methylene}-1,3-dihydro-indol-2-one
3-{[4-(2,6-Dimethyl-morpholin-4-yl)-3-fluoro-phenylamino]-methylene-1,3-dihydro-indol-2-one
3-{[4-(Butyl-propyl-amino)-3-fluoro-phenylamino]-methylene}-1,3-dihydro-indol-2-one
3-({3-Fluoro-4-[(2-methoxy-ethyl)-propyl-amino]-phenylamino-methylene)-1,3-dihydro-indol-2-one
3-{[4-(1,3-Dihydro-isoindol-2-yl)-3-fluoro-phenylamino]-methylene}-1,3-dihydro-indol-2-one
1-{2-Fluoro-4-[(2-oxo-1,2-dihydro-indol-3-ylidenemethyl)-amino]-phenyl}-piperidine-3-carboxylic acid amide
3-{[4-(4-Acetyl-piperazin-1-yl)-3-fluoro-phenylamino]-methylene}-1,3-dihydro-indol-2-one N-(1-{2-Fluoro-4-[(2-oxo-1,2-dihydro-indol-3-ylidenemethyl)-amino]-phenyl}-pyrrolidin-3-yl)-acetamide
3-{[3-Fluoro-4-(4-isopropyl-piperazin-1-yl)-phenylamino]-methylene}-1,3-dihydro-indol-2-one
3-{[3-Fluoro-4-(octahydro-isoquinolin-2-yl)-phenylamino]-methylene}-1,3-dihydro-indol-2-one
3-{[3-Fluoro-4-(octahydro-isoquinolin-2-yl)-phenylamino]-methylene}-1,3-dihydro-indol-2-one
3-{[4-(4-Butyl-piperazin-1-yl)-3-fluoro-phenylamino]-methylene}-1,3-dihydro-indol-2-one
3-{[4-(3-Diethylamino-pyrrolidin-1-yl)-3-fluoro-phenylamino]-methylene}-1,3-dihydro-indol-2-one
3-{[4-(1,4-Dioxa-8-aza-spiro[4.5]dec-8-yl)-3-fluoro-phenylamino]-methylene}-1,3-dihydro-indol-2-one
3-{[3-Fluoro-4-[4-(2-methoxy-ethyl)-piperazin-1-yl]-phenylamino}-methylene)-1,3-dihydro-indol-2-one
3-{[3-Fluoro-4-(3-pyridin-2-yl-pyrrolidin-1-yl)-phenylamino]-methylene}-1,3-dihydro-indol-2-one
3-{[3-Fluoro-4-(3-pyridin-4-yl-pyrrolidin-1-yl)-phenylamino]-methylene}-1,3-dihydro-indol-2-one
3-{[3-Fluoro-4-(4-propyl-piperidin-1-yl)-phenylamino]-methylene}-1,3-dihydro-indol-2-one
3-{[3-Fluoro-4-(4-pyrimidin-2-yl-piperazin-1-yl)-phenylamino]-methylene}-1,3-dihydro-indol-2-one
3-{[3-Fluoro-4-(2,3,5,6-tetrahydro-[1,2']bipyrazinyl-4-yl)-phenylamino]-methylene}-1,3-dihydro-indol-2-one
3-{[4-([1,3]Dioxolan-2-ylmethyl-methyl-amino)-3-fluoro-phenylamino]-methylene-1,3-dihydro-indol-2-one
3-({4-[(2-[1,3]Dioxolan-2-yl-ethyl)-methyl-amino]-3-fluoro-phenylamino}-methylene)-1,3-dihydro-indol-2-one
N-(1-{2-Fluoro-4-[(2-oxo-1,2-dihydro-indol-3-ylidenemethyl)-amino]-phenyl}-pyrrolidin-3-yl)-N-methyl-acetamide
3-{[3-Fluoro-4-(2-methoxy-ethylamino)-phenylamino]-methylene}-1,3-dihydro-indol-2-one
3-{[3-Fluoro-4-[(tetrahydro-furan-2-ylmethyl)-amino]-phenylamino}-methylene)-1,3-dihydro-indol-2-one
3-{[3-Fluoro-4-(tetrahydro-pyran-4-ylamino)-phenylamino]-methylene}-1,3-dihydro-indol-2-one
3-{[4-(3-Dimethylamino-propylamino)-3-fluoro-phenylamino]-methylene}-1,3-dihydro-indol-2-one
3-{[4-(2-Dimethylamino-1-methyl-ethylamino)-3-fluoro-phenylamino]-methylene}-1,3-dihydro-indol-2-one
3-{[3-Fluoro-4-(1-methoxymethyl-propylamino)-phenylamino]-methylene}-1,3-dihydro-indol-2-one
3-{[4-(2-Diethylamino-ethylamino)-3-fluoro-phenylamino]-methylene}-1,3-dihydro-indol-2-one
3-{[3-Fluoro-4-(2-pyridin-2-yl-ethylamino)-phenylamino]-methylene}-1,3-dihydro-indol-2-one
3-{[3-Fluoro-4-(2-pyridin-4-yl-ethylamino)-phenylamino]-methylene}-1,3-dihydro-indol-2-one
3-{[3-Fluoro-4-(2-pyridin-3-yl-ethylamino)-phenylamino]-methylene}-1,3-dihydro-indol-2-one
3-{[3-Fluoro-4-(2-morpholin-4-yl-ethylamino)-phenylamino]-methylene}-1,3-dihydro-indol-2-one
3-{[3-Fluoro-4-(3-morpholin-4-yl-propylamino)-phenylamino]-methylene-1,3-dihydro-indol-2-one
3-({3-Fluoro-4-[(pyridin-2-ylmethyl)-amino]-phenylamino}-methylene)-1,3-dihydro-indol-2-one
3-{[3-Fluoro-4-[(pyridin-3-ylmethyl)-amino]-phenylaminomethylene)-1,3-dihydro-indol-2-one
3-{[3-Fluoro-4-(2-methoxy-1-methyl-ethylamino)-phenylamino]-methylene}-1,3-dihydro-indol-2-one
3-{[4-(3-Diethylamino-propylamino)-3-fluoro-phenylamino]-methylene}-1,3-dihydro-indol-2-one
3-{[3-Fluoro-4-(3-imidazol-1-yl-propylamino)-phenylamino]-methylene}-1,3-dihydro-indol-2-one
3-{[4-(2-Diisopropylamino-ethylamino)-3-fluoro-phenylamino]-methylene}-1,3-dihydro-indol-2-one
3-({3-Fluoro-4-[(5-methyl-pyrazin-2-ylmethyl)-amino]-phenylamino}-methylene)-1,3-dihydro-indol-2-one
3-({4-[(2,2-Dimethyl-[1,3]dioxolan-4-ylmethyl)-amino]-3-fluoro-phenylamino}-methylene)-1,3-dihydro-indol-2-one
3-{2-Fluoro-4-[(2-oxo-1,2-dihydro-indol-3-ylidenemethyl)-amino]-phenylamino-pyrrolidine-1-carboxylic acid tert-butyl ester
3-{[3-Fluoro-4-(1,2,2,6,6-pentamethyl-piperidin-4-ylamino)-phenylamino]-methylene}-1,3-dihydro-indol-2-one
3-({3-Fluoro-4-[(tetrahydro-pyran-4-ylmethyl)-amino]-phenylamino}-methylene)-1,3-dihydro-indol-2-one
3-{[4-(2-Diethylamino-1-methyl-ethylamino)-3-fluoro-phenylamino]-methylene}-1,3-dihydro-indol-2-one
3-[(3-Fluoro-4-pyrrolidin-1-yl-phenylamino)-methylene]-4-methyl-1,3-dihydro-indol-2-one
3-[(4-Diethylamino-3-fluoro-phenylamino)-methylene]-4-methyl-1,3-dihydro-indol-2-one
1-{2-Fluoro-4-[(4-methyl-2-oxo-1,2-dihydro-indol-3-ylidenemethyl)-amino]-phenyl}-piperidine-4-carboxylic acid methyl ester
3-({3-Fluoro-4-[(2-methoxy-ethyl)-methyl-amino]-phenylamino}-methylene)-4-methyl-1,3-dihydro-indol-2-one
3-[(3-Fluoro-4-morpholin-4-yl-phenylamino)-methylene]-4-methyl-1,3-dihydro-indol-2-one
3-{[3-Fluoro-4-(3-methyl-piperidin-1-yl)-phenylamino]-methylene}-4-methyl-1,3-dihydro-indol-2-one
3-{[3-Fluoro-4-(4-methyl-piperidin-1-yl)-phenylamino]-methylene}-4-methyl-1,3-dihydro-indol-2-one
3-[(4-Azepan-1-yl-3-fluoro-phenylamino)-methylene]-4-methyl-1,3-dihydro-indol-2-one
3-{[3-Fluoro-4-(3-oxo-piperazin-1-yl)-phenylamino]-methylene}-4-methyl-1,3-dihydro-indol-2-one
3-{[3-Fluoro-4-(4-methyl-piperazin-1-yl)-phenylamino]-methylene}-4-methyl-1,3-dihydro-indol-2-one
3-[(4-Dipropylamino-3-fluoro-phenylamino)-methylene]-4-methyl-1,3-dihydro-indol-2-one
3-{[4-(Butyl-ethyl-amino)-3-fluoro-phenylamino]-methylene}-4-methyl-1,3-dihydro-indol-2-one
3-({4-[Ethyl-(2-methoxy-ethyl)-amino]-3-fluoro-phenylamino}-methylene)-4-methyl-1,3-dihydro-indol-2-one
4-{2-Fluoro-4-[(4-methyl-2-oxo-1,2-dihydro-indol-3-ylidenemethyl)-amino]-phenyl}-piperazine-1-carbaldehyde 3-{[3-Fluoro-4-(5-oxo-[1,4]diazepan-1-yl)-phenylamino]-methylene}-4-methyl-1,3-dihydro-indol-2-one
3-{[3-Fluoro-4-(4-methyl-[1,4]diazepan-1-yl)-phenylamino]-methylene}-4-methyl-1,3-dihydro-indol-2-one
3-{[4-(3-Dimethylamino-pyrrolidin-1-yl)-3-fluoro-phenylamino]-methylene}-4-methyl-1,3-dihydro-indol-2-one
3-{[4-(2,6-Dimethyl-morpholin-4-yl)-3-fluoro-phenylamino]-methylene}-4-methyl-1,3-dihydro-indol-2-one
3-{[4-(2,6-Dimethyl-morpholin-4-yl)-3-fluoro-phenylamino]-methylene-4-methyl-1,3-dihydro-indol-2-one
3-({3-Fluoro-4-[(2-methoxy-ethyl)-propyl-amino]-phenylamino}-methylene)-4-methyl-1,3-dihydro-indol-2-one
3-{[4-(4-Acetyl-piperazin-1-yl)-3-fluoro-phenylamino]-methylene}-4-methyl-1,3-dihydro-indol-2-one
3-{[3-Fluoro-4-(octahydro-isoquinolin-2-yl)-phenylamino]-methylene-4-methyl-1,3-dihydro-indol-2-one
3-{[3-Fluoro-4-(octahydro-isoquinolin-2-yl)-phenylamino]-methylene-4-methyl-1,3-dihydro-indol-2-one
3-{[4-(1,4-Dioxa-8-aza-spiro[4.5]dec-8-yl)-3-fluoro-phenylamino]-methylene-4-methyl-1,3-dihydro-indol-2-one
3-({3-Fluoro-4-[4-(2-methoxy-ethyl)-piperazin-1-yl]-phenylamino}-methylene)-4-methyl-1,3-dihydro-indol-2-one
3-{[3-Fluoro-4-(3-pyridin-2-yl-pyrrolidin-1-yl)-phenylamino]-methylene}-4-methyl-1,3-dihydro-indol-2-one
3-{[3-Fluoro-4-(3-pyridin-4-yl-pyrrolidin-1-yl)-phenylamino]-methylene}-4-methyl-1,3-dihydro-indol-2-one
3-{[3-Fluoro-4-(4-propyl-piperidin-1-yl)-phenylamino]-methylene}-4-methyl-1,3-dihydro-indol-2-one
3-{[3-Fluoro-4-(methyl-pyridin-3-ylmethyl-amino)-phenylamino]-methylene-4-methyl-1,3-dihydro-indol-2-one
3-({3-Fluoro-4-[methyl-(2-pyridin-2-yl-ethyl)-amino]-phenylamino-methylene)-4-methyl-1,3-dihydro-indol-2-one
3-{[3-Fluoro-4-(4-pyrimidin-2-yl-piperazin-1-yl)-phenylamino]-methylene}-4-methyl-1,3-dihydro-indol-2-one
3-{[3-Fluoro-4-(2,3,5,6-tetrahydro-[1,2']bipyrazinyl-4-yl)-phenylamino]-methylene}-4-methyl-1,3-dihydro-indol-2-one
3-{[4-([1,3]Dioxolan-2-ylmethyl-methyl-amino)-3-fluoro-phenylamino]-methylene-4-methyl-1,3-dihydro-indol-2-one
3-({4-[(2-[1,3]Dioxolan-2-yl-ethyl)-methyl-amino]-3-fluoro-phenylamino}-methylene)-4-methyl-1,3-dihydro-indol-2-one N-(1-{2-Fluoro-4-[(4-methyl-2-oxo-1,2-dihydro-indol-3-ylidenemethyl)-amino]-phenyl}-pyrrolidin-3-yl)-N-methyl-acetamide
3-{[3-Fluoro-4-(2-methoxy-ethylamino)-phenylamino]-methylene}-4-methyl-1,3-dihydro-indol-2-one
3-({3-Fluoro-4-[(tetrahydro-furan-2-ylmethyl)-amino]-phenylamino}-methylene)-4-methyl-1,3-dihydro-indol-2-one
3-{[4-(3-Dimethylamino-propylamino)-3-fluoro-phenylamino]-methylene-4-methyl-1,3-dihydro-indol-2-one
3-{[4-(2-Dimethylamino-1-methyl-ethylamino)-3-fluoro-phenylamino]-methylene}-4-methyl-1,3-dihydro-indol-2-one
3-{([3-Fluoro-4-(1-methoxymethyl-propylamino)-phenylamino]-methylene}-4-methyl-1,3-dihydro-indol-2-one
3-{[3-Fluoro-4-(2-pyridin-2-yl-ethylamino)-phenylamino]-methylene}-4-methyl-1,3-dihydro-indol-2-one
3-{[3-Fluoro-4-(2-pyridin-4-yl-ethylamino)-phenylamino]-methylene}-4-methyl-1,3-dihydro-indol-2-one
3-{[3-Fluoro-4-(3-morpholin-4-yl-propylamino)-phenylamino]-methylene}-4-methyl-1,3-dihydro-indol-2-one
3-({3-Fluoro-4-[(pyridin-2-ylmethyl)-amino]-phenylamino}-methylene)-4-methyl-1,3-dihydro-indol-2-one
3-({3-Fluoro-4-[(pyridin-3-ylmethyl)-amino]-phenylamino}-methylene)-4-methyl-1,3-dihydro-indol-2-one
3-({3-Fluoro-4-[(pyridin-4-ylmethyl)-amino]-phenylamino}-methylene)-4-methyl-1,3-dihydro-indol-2-one
3-{[3-Fluoro-4-(2-methoxy-1-methyl-ethylamino)-phenylamino]-methylene}-4-methyl-1,3-dihydro-indol-2-one
3-{[4-(2-Dimethylamino-ethylamino)-3-fluoro-phenylamino]-methylene}-4-methyl-1,3-dihydro-indol-2-one
3-({3-Fluoro-4-[(5-methyl-pyrazin-2-ylmethyl)-amino]-phenylamino}-methylene)-4-methyl-1,3-dihydro-indol-2-one
3-({4-[(2,2-Dimethyl-[1,3]dioxolan-4-ylmethyl)-amino]-3-fluoro-phenylamino}-methylene)-4-methyl-1,3-dihydro-indol-2-one
3-{2-Fluoro-4-[(4-methyl-2-oxo-1,2-dihydro-indol-3-ylidenemethyl)-amino]-phenylamino}-pyrrolidine-1-carboxylic acid tert-butyl ester
3-({3-Fluoro-4-[(tetrahydro-pyran-4-ylmethyl)-amino]-phenylamino}-methylene)-4-methyl-1,3-dihydro-indol-2-one
3-{[3-Fluoro-4-(2-hydroxy-ethylamino)-phenylamino]-methylene-4-methyl-1,3-dihydro-indol-2-one
4-Fluoro-3-[(3-fluoro-4-pyrrolidin-1-yl-phenylamino)-methylene]-1,3-dihydro-indol-2-one
3-[(4-Diethylamino-3-fluoro-phenylamino)-methylene]-4-fluoro-1,3-dihydro-indol-2-one
1-{2-Fluoro-4-[(4-fluoro-2-oxo-1,2-dihydro-indol-3-ylidenemethyl)-amino]-phenyl}-piperidine-4-carboxylic acid methyl ester
4-Fluoro-3-({3-fluoro-4-[(2-methoxy-ethyl)-methyl-amino]-phenylamino}-methylene)-1,3-dihydro-indol-2-one
4-Fluoro-3-[(3-fluoro-4-morpholin-4-yl-phenylamino)-methylene]-1,3-dihydro-indol-2-one
4-Fluoro-3-{[3-fluoro-4-(3-methyl-piperidin-1-yl)-phenylamino]-methylene}-1,3-dihydro-indol-2-one
4-Fluoro-3-{[3-fluoro-4-(4-methyl-piperidin-1-yl)-phenylamino]-methylene}-1,3-dihydro-indol-2-one
3-[(4-Azepan-1-yl-3-fluoro-phenylamino)-methylene]-4-fluoro-1,3-dihydro-indol-2-one
4-Fluoro-3-{[3-fluoro-4-(3-oxo-piperazin-1-yl)-phenylamino]-methylene}-1,3-dihydro-indol-2-one
4-Fluoro-3-{[3-fluoro-4-(4-methyl-piperazin-1-yl)-phenylamino]-methylene}-1,3-dihydro-indol-2-one
3-[(4-Dipropylamino-3-fluoro-phenylamino)-methylene]-4-fluoro-1,3-dihydro-indol-2-one
3-{[4-(Butyl-ethyl-amino)-3-fluoro-phenylamino]-methylene}-4-fluoro-1,3-dihydro-indol-2-one
3-({4-[Ethyl-(2-methoxy-ethyl)-amino]-3-fluoro-phenylamino}-methylene)-4-fluoro-1,3-dihydro-indol-2-one
4-Fluoro-3-[(3-fluoro-4-thiomorpholin-4-yl-phenylamino)-methylene]-1,3-dihydro-indol-2-one
3-{[4-(Cyclopropylmethyl-propyl-amino)-3-fluoro-phenylamino]-methylene}-4-fluoro-1,3-dihydro-indol-2-one
3-{[4-(3,5-Dimethyl-piperidin-1-yl)-3-fluoro-phenylamino]-methylene}-4-fluoro-1,3-dihydro-indol-2-one
4-{2-Fluoro-4-[(4-fluoro-2-oxo-1,2-dihydro-indol-3-ylidenemethyl)-amino]-phenyl}-piperazine-1-carbaldehyde
4-Fluoro-3-{[3-fluoro-4-(5-oxo-[1,4]diazepan-1-yl)-phenylamino]-methylene}-1,3-dihydro-indol-2-one
3-{[4-(3,5-Dimethyl-piperazin-1-yl)-3-fluoro-phenylamino]-methylene}-4-fluoro-1,3-dihydro-indol-2-one
4-Fluoro-3-{[3-fluoro-4-(4-methyl-[1,4]diazepan-1-yl)-phenylamino]-methylene}-1,3-dihydro-indol-2-one
3-{[4-(4-Ethyl-piperazin-1-yl)-3-fluoro-phenylamino]-methylene}-4-fluoro-1,3-dihydro-indol-2-one 3-{[4-(3-Dimethylamino-pyrrolidin-1-yl)-3-fluoro-phenylamino]-methylene}-4-fluoro-1,3-dihydro-indol-2-one
3-{[4-(2,6-Dimethyl-morpholin-4-yl)-3-fluoro-phenylamino]-methylene-4-fluoro-1,3-dihydro-indol-2-one
3-{[4-(2,6-Dimethyl-morpholin-4-yl)-3-fluoro-phenylamino]-methylene-4-fluoro-1,3-dihydro-indol-2-one
3-{[4-(Butyl-propyl-amino)-3-fluoro-phenylamino]-methylene}-4-fluoro-1,3-dihydro-indol-2-one
4-Fluoro-3-({3-fluoro-4-[(2-methoxy-ethyl)-propyl-amino]-phenylamino}-methylene)-1,3-dihydro-indol-2-one
1-{2-Fluoro-4-[(4-fluoro-2-oxo-1,2-dihydro-indol-3-ylidenemethyl)-amino]-phenyl}-piperidine-3-carboxylic acid amide
1-{2-Fluoro-4-[(4-fluoro-2-oxo-1,2-dihydro-indol-3-ylidenemethyl)-amino]-phenyl}-piperidine-4-carboxylic acid amide
3-{[4-(4-Acetyl-piperazin-1-yl)-3-fluoro-phenylamino]-methylene}-4-fluoro-1,3-dihydro-indol-2-one
4-Fluoro-3-{[3-fluoro-4-(4-isopropyl-piperazin-1-yl)-phenylamino]-methylene}-1,3-dihydro-indol-2-one
4-Fluoro-3-{[3-fluoro-4-(octahydro-isoquinolin-2-yl)-phenylamino]-methylene}-1,3-dihydro-indol-2-one
3-{[4-(4-Butyl-piperazin-1-yl)-3-fluoro-phenylamino]-methylene}-4-fluoro-1,3-dihydro-indol-2-one
3-{[4-(4-sec-Butyl-piperazin-1-yl)-3-fluoro-phenylamino]-methylene}-4-fluoro-1,3-dihydro-indol-2-one
3-{[4-(3-Diethylamino-pyrrolidin-1-yl)-3-fluoro-phenylamino]-methylene}-4-fluoro-1,3-dihydro-indol-2-one
3-{[4-(1,4-Dioxa-8-aza-spiro[4.5]dec-8-yl)-3-fluoro-phenylamino]-methylene}-4-fluoro-1,3-dihydro-indol-2-one
4-Fluoro-3-({3-fluoro-4-[4-(2-methoxy-ethyl)-piperazin-1-yl]-phenylamino}-methylene)-1,3-dihydro-indol-2-one
4-Fluoro-3-{[3-fluoro-4-(3-pyridin-2-yl-pyrrolidin-1-yl)-phenylamino]-methylene}-1,3-dihydro-indol-2-one
4-Fluoro-3-{[3-fluoro-4-(3-pyridin-4-yl-pyrrolidin-1-yl)-phenylamino]-methylene}-1,3-dihydro-indol-2-one
4-Fluoro-3-{[3-fluoro-4-(4-propyl-piperidin-1-yl)-phenylamino]-methylene}-1,3-dihydro-indol-2-one
4-Fluoro-3-{[3-fluoro-4-(methyl-pyridin-3-ylmethyl-amino)-phenylamino]-methylene}-1,3-dihydro-indol-2-one
4-Fluoro-3-({3-fluoro-4-[methyl-(2-pyridin-2-yl-ethyl)-amino]-phenylamino}-methylene)-1,3-dihydro-indol-2-one
4-Fluoro-3-{[3-fluoro-4-(4-pyrimidin-2-yl-piperazin-1-yl)-phenylamino]-methylene}-1,3-dihydro-indol-2-one
4-Fluoro-3-{[3-fluoro-4-(2,3,5,6-tetrahydro-[1,2']bipyrazinyl-4-yl)-phenylamino]-methylene}-1,3-dihydro-indol-2-one
3-{[4-([1,3]Dioxolan-2-ylmethyl-methyl-amino)-3-fluoro-phenylamino]-methylene}-4-fluoro-1,3-dihydro-indol-2-one
3-({4-[(2-[1,3]Dioxolan-2-yl-ethyl)-methyl-amino]-3-fluoro-phenylamino}-methylene)-4-fluoro-1,3-dihydro-indol-2-one
4-Fluoro-3-{[3-fluoro-4-(2-methoxy-ethylamino)-phenylamino]-methylene}-1,3-dihydro-indol-2-one
4-Fluoro-3-({3-fluoro-4-[(tetrahydro-furan-2-ylmethyl)-amino]-phenylamino}-methylene)-1,3-dihydro-indol-2-one
4-Fluoro-3-{[3-fluoro-4-(tetrahydro-pyran-4-ylamino)-phenylamino]-methylene}-1,3-dihydro-indol-2-one
3-{[4-(3-Dimethylamino-propylamino)-3-fluoro-phenylamino]-methylene}-4-fluoro-1,3-dihydro-indol-2-one
3-{[4-(2-Dimethylamino-1-methyl-ethylamino)-3-fluoro-phenylamino]-methylene}-4-fluoro-1,3-dihydro-indol-2-one
4-Fluoro-3-{[3-fluoro-4-(1-methoxymethyl-propylamino)-phenylamino]-methylene}-1,3-dihydro-indol-2-one
3-{[4-(2-Diethylamino-ethylamino)-3-fluoro-phenylamino]-methylene}-4-fluoro-1,3-dihydro-indol-2-one
4-Fluoro-3-{[3-fluoro-4-(2-pyridin-2-yl-ethylamino)-phenylamino]-methylene}-1,3-dihydro-indol-2-one
4-Fluoro-3-{[3-fluoro-4-(2-pyridin-4-yl-ethylamino)-phenylamino]-methylene}-1,3-dihydro-indol-2-one
4-Fluoro-3-{[3-fluoro-4-(2-morpholin-4-yl-ethylamino)-phenylamino]-methylene-1,3-dihydro-indol-2-one
4-Fluoro-3-{[3-fluoro-4-(3-morpholin-4-yl-propylamino)-phenylamino]-methylene}-1,3-dihydro-indol-2-one
4-Fluoro-3-({3-fluoro-4-[(pyridin-4-ylmethyl)-amino]-phenylamino}-methylene)-1,3-dihydro-indol-2-one
4-Fluoro-3-{[3-fluoro-4-(2-piperidin-1-yl-ethylamino)-phenylamino]-methylene}-1,3-dihydro-indol-2-one
4-Fluoro-3-({3-fluoro-4-[3-(2-methyl-piperidin-1-yl)-propylamino]-phenylamino}-methylene)-1,3-dihydro-indol-2-one
4-Fluoro-3-{[3-fluoro-4-(2-methoxy-1-methyl-ethylamino)-phenylamino]-methylene}-1,3-dihydro-indol-2-one
3-{[4-(2-Dimethylamino-ethylamino)-3-fluoro-phenylamino]-methylene}-4-fluoro-1,3-dihydro-indol-2-one
3-{[4-(3-Diethylamino-propylamino)-3-fluoro-phenylamino]-methylene}-4-fluoro-1,3-dihydro-indol-2-one
4-Fluoro-3-{[3-fluoro-4-(3-imidazol-1-yl-propylamino)-phenylamino]-methylene}-1,3-dihydro-indol-2-one
3-{[4-(2-Diisopropylamino-ethylamino)-3-fluoro-phenylamino]-methylene}-4-fluoro-1,3-dihydro-indol-2-one
3-{[4-(1-Benzyl-pyrrolidin-3-ylamino)-3-fluoro-phenylamino]-methylene}-4-fluoro-1,3-dihydro-indol-2-one
4-Fluoro-3-({3-fluoro-4-[(5-methyl-pyrazin-2-ylmethyl)-amino]-phenylamino}-methylene)-1,3-dihydro-indol-2-one
3-({4-[(2,2-Dimethyl-[1,3]dioxolan-4-ylmethyl)-amino]-3-fluoro-phenylamino}-methylene)-4-fluoro-1,3-dihydro-indol-2-one
3-{2-Fluoro-4-[(4-fluoro-2-oxo-1,2-dihydro-indol-3-ylidenemethyl)-amino]-phenylamino}-pyrrolidine-1-carboxylic acid tert-butyl ester
4-Fluoro-3-{[3-fluoro-4-(1,2,2,6,6-pentamethyl-piperidin-4-ylamino)-phenylamino]-methylene}-1,3-dihydro-indol-2-one
4-Fluoro-3-({3-fluoro-4-[(tetrahydro-pyran-4-ylmethyl)-amino]-phenylamino}-methylene)-1,3-dihydro-indol-2-one
4-Fluoro-3-[([3-fluoro-4-(2-hydroxy-ethylamino)-phenylamino]-methylene}-1,3-dihydro-indol-2-one
3-{[4-(2-Diethylamino-1-methyl-ethylamino)-3-fluoro-phenylamino]-methylene}-4-fluoro-1,3-dihydro-indol-2-one
3-[([4-(2,5-Dihydro-pyrrol-1-yl)-3-fluoro-phenylamino]-methylene}-5-fluoro-1,3-dihydro-indol-2-one
5-Fluoro-3-[(3-fluoro-4-pyrrolidin-1-yl-phenylamino)-methylene]-1,3-dihydro-indol-2-one
3-[(4-Diethylamino-3-fluoro-phenylamino)-methylene]-5-fluoro-1,3-dihydro-indol-2-one
1-{2-Fluoro-4-[(5-fluoro-2-oxo-1,2-dihydro-indol-3-ylidenemethyl)-amino]-phenyl}-piperidine-4-carboxylic acid methyl ester
5-Fluoro-3-({3-fluoro-4-[(2-methoxy-ethyl)-methyl-amino]-phenylamino}-methylene)-1,3-dihydro-indol-2-one 3-{[4-(3,6-Dihydro-2H-pyridin-1-yl)-3-fluoro-phenylamino]-methylene}-5-fluoro-1,3-dihydro-indol-2-one 5-Fluoro-3-[(3-fluoro-4-morpholin-4-yl-phenylamino)-methylene]-1,3-dihydro-indol-2-one 5-Fluoro-3-{[3-fluoro-4-(3-methyl-piperidin-1-yl)-phenylamino]-methylene}-1,3-dihydro-indol-2-one 5-Fluoro-3-{[3-fluoro-4-(4-methyl-piperidin-1-yl)-phenylamino]-methylene}-1,3-dihydro-indol-2-one 5-Fluoro-3-{[3-fluoro-4-(4-methyl-piperazin-1-yl)-phenylamino]-methylene}-1,3-dihydro-indol-2-one 3-{[4-(Butyl-ethyl-amino)-3-fluoro-phenylamino]-methylene}-5-fluoro-1,3-dihydro-indol-2-one 4-{2-Fluoro-4-[(5-fluoro-2-oxo-1,2-dihydro-indol-3-ylidenemethyl)-amino]-phenyl}-piperazine-1-carbaldehyde 3-{[4-(3,5-Dimethyl-piperazin-1-yl)-3-fluoro-phenylamino]-methylene}-5-fluoro-1,3-dihydro-indol-2-one 5-Fluoro-3-{[3-fluoro-4-(4-methyl-[1,4]diazepan-1-yl)-phenylamino]-methylene}-1,3-dihydro-indol-2-one 3-{[4-(4-Ethyl-piperazin-1-yl)-3-fluoro-phenylamino]-methylene}-5-fluoro-1,3-dihydro-indol-2-one 3-{[4-(3-Dimethylamino-pyrrolidin-1-yl)-3-fluoro-phenylamino]-methylene}-5-fluoro-1,3-dihydro-indol-2-one 3-{[4-(2,6-Dimethyl-morpholin-4-yl)-3-fluoro-phenylamino]-methylene}-5-fluoro-1,3-dihydro-indol-2-one 3-{[4-(2,6-Dimethyl-morpholin-4-yl)-3-fluoro-phenylamino]-methylene}-5-fluoro-1,3-dihydro-indol-2-one 5-Fluoro-3-({3-fluoro-4-[(2-methoxy-ethyl)-propyl-amino]-phenylamino}-methylene)-1,3-dihydro-indol-2-one 3-{[4-(1,3-Dihydro-isoindol-2-yl)-3-fluoro-phenylamino]-methylene)-5-fluoro-1,3-dihydro-indol-2-one 1-{2-Fluoro-4-[(5-fluoro-2-oxo-1,2-dihydro-indol-3-ylidenemethyl)-amino]-phenyl}-piperidine-3-carboxylic acid amide 1-{2-Fluoro-4-[(5-fluoro-2-oxo-1,2-dihydro-indol-3-ylidenemethyl)-amino]-phenyl}-piperidine-4-carboxylic acid amide 5-Fluoro-3-{[3-fluoro-4-(4-isopropyl-piperazin-1-yl)-phenylamino]-methylene}-1,3-dihydro-indol-2-one 5-Fluoro-3-{[3-fluoro-4-(octahydro-isoquinolin-2-yl)-phenylamino]-methylene}-1,3-dihydro-indol-2-one 5-Fluoro-3-{[3-fluoro-4-(octahydro-isoquinolin-2-yl)-phenylamino]-methylene}-1,3-dihydro-indol-2-one 3-{[4-(4-Acetyl-[1,4]diazepan-1-yl)-3-fluoro-phenylamino]-methylene}-5-fluoro-1,3-dihydro-indol-2-one 3-{[4-(4-Butyl-piperazin-1-yl)-3-fluoro-phenylamino]-methylene}-5-fluoro-1,3-dihydro-indol-2-one 3-{[4-(4-sec-Butyl-piperazin-1-yl)-3-fluoro-phenylamino]-methylene}-5-fluoro-1,3-dihydro-indol-2-one 3-{[4-(3-Diethylamino-pyrrolidin-1-yl)-3-fluoro-phenylamino]-methylene}-5-fluoro-1,3-dihydro-indol-2-one 3-{[4-(1,4-Dioxa-8-aza-spiro[4.5]dec-8-yl)-3-fluoro-phenylamino]-methylene}-5-fluoro-1,3-dihydro-indol-2-one 5-Fluoro-3-({3-fluoro-4-[4-(2-methoxy-ethyl)-piperazin-1-yl]-phenylamino}-methylene)-1,3-dihydro-indol-2-one 5-Fluoro-3-{[3-fluoro-4-(3-pyridin-2-yl-pyrrolidin-1-yl)-phenylamino]-methylene}-1,3-dihydro-indol-2-one 5-Fluoro-3-{[3-fluoro-4-(3-pyridin-4-yl-pyrrolidin-1-yl)-phenylamino]-methylene}-1,3-dihydro-indol-2-one 5-Fluoro-3-{([3-fluoro-4-(methyl-pyridin-3-ylmethyl-amino)-phenylamino]-methylene}-1,3-dihydro-indol-2-one 5-Fluoro-3-(3-fluoro-4-[methyl-(2-pyridin-2-yl-ethyl)-amino]-phenylamino}-methylene)-1,3-dihydro-indol-2-one 5-Fluoro-3-{[3-fluoro-4-(2,3,5,6-tetrahydro-[1,2']bipyrazinyl-4-yl)-phenylamino]-methylene}-1,3-dihydro-indol-2-one 3-{[4-([1,3]Dioxolan-2-ylmethyl-methyl-amino)-3-fluoro-phenylamino]-methylene}-5-fluoro-1,3-dihydro-indol-2-one 3-({4-[(2-[1,3]Dioxolan-2-yl-ethyl)-methyl-amino]-3-fluoro-phenylamino}-methylene)-5-fluoro-1,3-dihydro-indol-2-one N-(1-{2-Fluoro-4-[(5-fluoro-2-oxo-1,2-dihydro-indol-3-ylidenemethyl)-amino]-phenyl}-pyrrolidin-3-yl)-N-methyl-acetamide 5-Fluoro-3-{[3-fluoro-4-(2-methoxy-ethylamino)-phenylamino]-methylene}-1,3-dihydro-indol-2-one 5-Fluoro-3-({3-fluoro-4-[(tetrahydro-furan-2-ylmethyl)-amino]-phenylamino}-methylene)-1,3-dihydro-indol-2-one 5-Fluoro-3-{[3-fluoro-4-(tetrahydro-pyran-4-ylamino)-phenylamino]-methylene}-1,3-dihydro-indol-2-one 5-Fluoro-3-{[3-fluoro-4-(tetrahydro-pyran-4-ylamino)-phenylamino]-methylene}-1,3-dihydro-indol-2-one 3-{[4-(2-Dimethylamino-1-methyl-ethylamino)-3-fluoro-phenylamino]-methylene}-5-fluoro-1,3-dihydro-indol-2-one 5-Fluoro-3-{[3-fluoro-4-(1-methoxymethyl-propylamino)-phenylamino]-methylene}-1,3-dihydro-indol-2-one 3-{[4-(2-Diethylamino-ethylamino)-3-fluoro-phenylamino]-methylene}-5-fluoro-1,3-dihydro-indol-2-one 5-Fluoro-3-{[3-fluoro-4-(2-pyridin-4-yl-ethylamino)-phenylamino]-methylene}-1,3-dihydro-indol-2-one 5-Fluoro-3-{[3-fluoro-4-(2-pyridin-3-yl-ethylamino)-phenylamino]-methylene}-1,3-dihydro-indol-2-one 5-Fluoro-3-{[3-fluoro-4-(3-morpholin-4-yl-propylamino)-phenylamino]-methylene}-1,3-dihydro-indol-2-one 5-Fluoro-3-{[3-fluoro-4-[3-(2-methyl-piperidin-1-yl)-propylamino]-phenylamino}-methylene)-1,3-dihydro-indol-2-one 5-Fluoro-3-{[3-fluoro-4-(2-methoxy-1-methyl-ethylamino)-phenylamino]-methylene}-1,3-dihydro-indol-2-one 3-{[4-(3-Diethylamino-propylamino)-3-fluoro-phenylamino]-methylene}-5-fluoro-1,3-dihydro-indol-2-one 5-Fluoro-3-{[3-fluoro-4-(3-imidazol-1-yl-propylamino)-phenylamino]-methylene}-1,3-dihydro-indol-2-one 3-{[4-(1-Benzyl-pyrrolidin-3-ylamino)-3-fluoro-phenylamino]-methylene-5-fluoro-1,3-dihydro-indol-2-one 5-Fluoro-3-({3-fluoro-4-[(5-methyl-pyrazin-2-ylmethyl)-amino]-phenylamino}-methylene)-1,3-dihydro-indol-2-one 3-({4-[(2,2-Dimethyl-[1,3]dioxolan-4-ylmethyl)-amino]-3-fluoro-phenylamino-methylene)-5-fluoro-1,3-dihydro-indol-2-one 3-{2-Fluoro-4-[(5-fluoro-2-oxo-1,2-dihydro-indol-3-ylidenemethyl)-amino]-phenylamino}-pyrrolidine-1-carboxylic acid tert-butyl ester 5-Fluoro-3-{[3-fluoro-4-(1,2,2,6,6-pentamethyl-piperidin-4-ylamino)-phenylamino]-methylene}-1,3-dihydro-indol-2-one 5-Fluoro-3-{[3-fluoro-4-[(tetrahydro-pyran-4-ylmethyl)-amino]-phenylamino}-methylene)-1,3-dihydro-indol-2-one 5-Fluoro-3-{[3-fluoro-4-(2-hydroxy-ethylamino)-phenylamino]-methylene}-1,3-dihydro-indol-2-one 3-{[4-(2-Diethylamino-1-methyl-ethylamino)-3-fluoro-phenylamino]-methylene}-5-fluoro-1,3-dihydro-indol-2-one 3-{[4-(2,5-Dihydro-pyrrol-1-yl)-3-fluoro-phenylamino]-methylene}-6-fluoro-1,3-dihydro-indol-2-one 6-Fluoro-3-[(3-fluoro-4-pyrrolidin-1-yl-phenylamino)-methylene]-1,3-dihydro-indol-2-one
3-[(4-Diethylamino-3-fluoro-phenylamino)-methylene]-6-fluoro-1,3-dihydro-indol-2-one
1-{2-Fluoro-4-[(6-fluoro-2-oxo-1,2-dihydro-indol-3-ylidenemethyl)-amino]-phenyl}-piperidine-4-carboxylic acid methyl ester
6-Fluoro-3-({3-fluoro-4-[(2-methoxy-ethyl)-methyl-amino]-phenylamino}-methylene)-1,3-dihydro-indol-2-one
3-{[4-(3,6-Dihydro-2H-pyridin-1-yl)-3-fluoro-phenylamino]-methylene}-6-fluoro-1,3-dihydro-indol-2-one
6-Fluoro-3-[(3-fluoro-4-morpholin-4-yl-phenylamino)-methylene]-1,3-dihydro-indol-2-one
6-Fluoro-3-{[3-fluoro-4-(3-methyl-piperidin-1-yl)-phenylamino]-methylene}-1,3-dihydro-indol-2-one
6-Fluoro-3-{[3-fluoro-4-(4-methyl-piperidin-1-yl)-phenylamino]-methylene}-1,3-dihydro-indol-2-one
6-Fluoro-3-{[3-fluoro-4-(3-oxo-piperazin-1-yl)-phenylamino]-methylene}-1,3-dihydro-indol-2-one
6-Fluoro-3-{[3-fluoro-4-(4-methyl-piperazin-1-yl)-phenylamino]-methylene}-1,3-dihydro-indol-2-one
3-[(4-Dipropylamino-3-fluoro-phenylamino)-methylene]-6-fluoro-1,3-dihydro-indol-2-one
3-{([4-(Butyl-ethyl-amino)-3-fluoro-phenylamino]-methylene}-6-fluoro-1,3-dihydro-indol-2-one
3-({4-[Ethyl-(2-methoxy-ethyl)-amino]-3-fluoro-phenylamino}-methylene)-6-fluoro-1,3-dihydro-indol-2-one
6-Fluoro-3-[(3-fluoro-4-thiomorpholin-4-yl-phenylamino)-methylene]-1,3-dihydro-indol-2-one
3-{[4-(Cyclopropylmethyl-propyl-amino)-3-fluoro-phenylamino]-methylene}-6-fluoro-1,3-dihydro-indol-2-one
4-[(2-Fluoro-4-[(6-fluoro-2-oxo-1,2-dihydro-indol-3-ylidenemethyl)-amino]-phenyl}-piperazine-1-carbaldehyde
6-Fluoro-3-{[3-fluoro-4-(5-oxo-[1,4]diazepan-1-yl)-phenylamino]-methylene}-1,3-dihydro-indol-2-one
3-{([4-(3,5-Dimethyl-piperazin-1-yl)-3-fluoro-phenylamino]-methylene}-6-fluoro-1,3-dihydro-indol-2-one
3-{[4-(4-Ethyl-piperazin-1-yl)-3-fluoro-phenylamino]-methylene}-6-fluoro-1,3-dihydro-indol-2-one
3-{[4-(3-Dimethylamino-pyrrolidin-1-yl)-3-fluoro-phenylamino]-methylene}-6-fluoro-1,3-dihydro-indol-2-one
3-{[4-(Butyl-propyl-amino)-3-fluoro-phenylamino]-methylene}-6-fluoro-1,3-dihydro-indol-2-one
6-Fluoro-3-{[3-fluoro-4-[(2-methoxy-ethyl)-propyl-amino]-phenylamino}-methylene)-1,3-dihydro-indol-2-one
3-{[4-(1,3-Dihydro-isoindol-2-yl)-3-fluoro-phenylamino]-methylene-6-fluoro-1,3-dihydro-indol-2-one
1-{2-Fluoro-4-[(6-fluoro-2-oxo-1,2-dihydro-indol-3-ylidenemethyl)-amino]-phenyl}-piperidine-3-carboxylic acid amide
1-{2-Fluoro-4-[(6-fluoro-2-oxo-1,2-dihydro-indol-3-ylidenemethyl)-amino]-phenyl}-piperidine-4-carboxylic acid amide
6-Fluoro-3-{[3-fluoro-4-(4-isopropyl-piperazin-1-yl)-phenylamino]-methylene}-1,3-dihydro-indol-2-one
6-Fluoro-3-[([3-fluoro-4-(octahydro-isoquinolin-2-yl)-phenylamino]-methylene)-1,3-dihydro-indol-2-one
3-{[4-(4-Butyl-piperazin-1-yl)-3-fluoro-phenylamino]-methylene}-6-fluoro-1,3-dihydro-indol-2-one
3-{[4-(4-sec-Butyl-piperazin-1-yl)-3-fluoro-phenylamino]-methylene}-6-fluoro-1,3-dihydro-indol-2-one
3-{[4-(3-Diethylamino-pyrrolidin-1-yl)-3-fluoro-phenylamino]-methylene}-6-fluoro-1,3-dihydro-indol-2-one
3-{[4-(1,4-Dioxa-8-aza-spiro[4.5]dec-8-yl)-3-fluoro-phenylamino]-methylene}-6-fluoro-1,3-dihydro-indol-2-one
6-Fluoro-3-({3-fluoro-4-[4-(2-methoxy-ethyl)-piperazin-1-yl]-phenylamino}-methylene)-1,3-dihydro-indol-2-one
6-Fluoro-3-{[3-fluoro-4-(3-pyridin-2-yl-pyrrolidin-1-yl)-phenylamino]-methylene}-1,3-dihydro-indol-2-one
6-Fluoro-3-{[3-fluoro-4-(3-pyridin-4-yl-pyrrolidin-1-yl)-phenylamino]-methylene}-1,3-dihydro-indol-2-one
6-Fluoro-3-{[3-fluoro-4-(4-propyl-piperidin-1-yl)-phenylamino]-methylene}-1,3-dihydro-indol-2-one
6-Fluoro-3-{[3-fluoro-4-(methyl-pyridin-3-ylmethyl-amino)-phenylamino]-methylene}-1,3-dihydro-indol-2-one
6-Fluoro-3-{[3-fluoro-4-(4-pyrimidin-2-yl-piperazin-1-yl)-phenylamino]-methylene}-1,3-dihydro-indol-2-one
6-Fluoro-3-{[3-fluoro-4-(2,3,5,6-tetrahydro-[1,2']bipyrazinyl-4-yl)-phenylamino]-methylene}-1,3-dihydro-indol-2-one
3-{[4-([1,3]Dioxolan-2-ylmethyl-methyl-amino)-3-fluoro-phenylamino]-methylene-6-fluoro-1,3-dihydro-indol-2-one
3-({4-[(2-[1,3]Dioxolan-2-yl-ethyl)-methyl-amino]-3-fluoro-phenylamino}-methylene)-6-fluoro-1,3-dihydro-indol-2-one
N-(1-{2-Fluoro-4-[(6-fluoro-2-oxo-1,2-dihydro-indol-3-ylidenemethyl)-amino]-phenyl}-pyrrolidin-3-yl)-N-methyl-acetamide
6-Fluoro-3-({3-fluoro-4-(2-methoxy-ethylamino)-phenylamino}-methylene}-1,3-dihydro-indol-2-one
6-Fluoro-3-({3-fluoro-4-[(tetrahydro-furan-2-ylmethyl)-amino]-phenylamino}-methylene)-1,3-dihydro-indol-2-one
6-Fluoro-3-{[3-fluoro-4-(tetrahydro-pyran-4-ylamino)-phenylamino]-methylene}-1,3-dihydro-indol-2-one
3-{[4-(3-Dimethylamino-propylamino)-3-fluoro-phenylamino]-methylene}-6-fluoro-1,3-dihydro-indol-2-one
3-{[4-(2-Dimethylamino-1-methyl-ethylamino)-3-fluoro-phenylamino]-methylene}-6-fluoro-1,3-dihydro-indol-2-one
6-Fluoro-3-{[3-fluoro-4-(1-methoxymethyl-propylamino)-phenylamino]-methylene}-1,3-dihydro-indol-2-one
6-Fluoro-3-{[3-fluoro-4-(2-pyridin-2-yl-ethylamino)-phenylamino]-methylene}-1,3-dihydro-indol-2-one
6-Fluoro-3-{[3-fluoro-4-(2-pyridin-4-yl-ethylamino)-phenylamino]-methylene}-1,3-dihydro-indol-2-one
6-Fluoro-3-{[3-fluoro-4-(2-pyridin-3-yl-ethylamino)-phenylamino]-methylene}-1,3-dihydro-indol-2-one
6-Fluoro-3-{([3-fluoro-4-(2-morpholin-4-yl-ethylamino)-phenylamino]-methylene}-1,3-dihydro-indol-2-one
6-Fluoro-3-{[3-fluoro-4-(3-morpholin-4-yl-propylamino)-phenylamino]-methylene}-1,3-dihydro-indol-2-one
6-Fluoro-3-(3-fluoro-4-[(pyridin-3-ylmethyl)-amino]-phenylamino}-methylene)-1,3-dihydro-indol-2-one
6-Fluoro-3-{[3-fluoro-4-(2-piperidin-1-yl-ethylamino)-phenylamino]-methylene}-1,3-dihydro-indol-2-one
6-Fluoro-3-{[3-fluoro-4-(2-methoxy-1-methyl-ethylamino)-phenylamino]-methylene}-1,3-dihydro-indol-2-one
3-{[4-(2-Dimethylamino-ethylamino)-3-fluoro-phenylamino]-methylene}-6-fluoro-1,3-dihydro-indol-2-one
3-{[4-(3-Diethylamino-propylamino)-3-fluoro-phenylamino]-methylene}-6-fluoro-1,3-dihydro-indol-2-one
3-{[4-(2-Diisopropylamino-ethylamino)-3-fluoro-phenylamino]-methylene-6-fluoro-1,3-dihydro-indol-2-one
3-{[4-(1-Benzyl-pyrrolidin-3-ylamino)-3-fluoro-phenylamino]-methylene}-6-fluoro-1,3-dihydro-indol-2-one 6-Fluoro-3-({3-fluoro-4-[(5-methyl-pyrazin-2-ylmethyl)-amino]-phenylamino}-methylene)-1,3-dihydro-indol-2-one 3-({4-[(2,2-Dimethyl-[1,3]dioxolan-4-ylmethyl)-amino]-3-fluoro-phenylamino}-methylene)-6-fluoro-1,3-dihydro-indol-2-one 3-{2-Fluoro-4-[(6-fluoro-2-oxo-1,2-dihydro-indol-3-ylidenemethyl)-amino]-phenylaminol} pyrrolidine-1-carboxylic acid tert-butyl ester 6-Fluoro-3-{[3-fluoro-4-(1,2,2,6,6-pentamethyl-piperidin-4-ylamino)-phenylamino]-methylene}-1,3-dihydro-indol-2-one 6-Fluoro-3-({3-fluoro-4-[(tetrahydro-pyran-4-ylmethyl)-amino]-phenylamino}-methylene)-1,3-dihydro-indol-2-one 6-Fluoro-3-{[3-fluoro-4-(2-hydroxy-ethylamino)-phenylamino]-methylene-1,3-dihydro-indol-2-one 3-{[4-(2-Diethylamino-1-methyl-ethylamino)-3-fluoro-phenylamino]-methylene}-6-fluoro-1,3-dihydro-indol-2-one 3-[(3-Methyl-4-pyrrolidin-1-yl-phenylamino)-methylene]-1,3-dihydro-indol-2-one 3-({4-[(2-Methoxy-ethyl)-methyl-amino]-3-methyl-phenylamino}-methylene)-1,3-dihydro-indol-2-one 3-[(4-Azocan-1-yl-3-methyl-phenylamino)-methylene]-1,3-dihydro-indol-2-one 3-{([3-Methyl-4-(5-oxo-[1,4]diazepan-1-yl)-phenylamino]-methylene}-1,3-dihydro-indol-2-one 1-{2-Methyl-4-[(2-oxo-1,2-dihydro-indol-3-ylidenemethyl)-amino]-phenyl}-piperidine-4-carboxylic acid amide 3-({4-(4-Isopropyl-piperazin-1-yl)-3-methyl-phenylamino]-methylene}-1,3-dihydro-indol-2-one 3-([3-Methyl-4-(octahydro-isoquinolin-2-yl)-phenylamino]-methylene}-1,3-dihydro-indol-2-one 3-({4-(3-Diethylamino-pyrrolidin-1-yl)-3-methyl-phenylamino]-methylene}-1,3-dihydro-indol-2-one 3-([4-(3-Dimethylamino-propylamino)-3-methyl-phenylamino]-methylene}-1,3-dihydro-indol-2-one 3-([4-(1-Methoxymethyl-propylamino)-3-methyl-phenylamino]-methylene}-1,3-dihydro-indol-2-one 3-([4-(2-Diethylamino-ethylamino)-3-methyl-phenylamino]-methylene}-1,3-dihydro-indol-2-one 3-([3-Methyl-4-(2-morpholin-4-yl-ethylamino)-phenylamino]-methylene}-1,3-dihydro-indol-2-one 3-([3-Methyl-4-(3-morpholin-4-yl-propylamino)-phenylamino]-methylene-1,3-dihydro-indol-2-one 3-{[4-(2-Dimethylamino-ethylamino)-3-methyl-phenylamino]-methylene}-1,3-dihydro-indol-2-one 3-([4-(3-Diethylamino-propylamino)-3-methyl-phenylamino]-methylene}-1,3-dihydro-indol-2-one 3-{[4-(2-Diisopropylamino-ethylamino)-3-methyl-phenylamino]-methylene-1,3-dihydro-indol-2-one 3-(13-Methyl-4-[(5-methyl-pyrazin-2-ylmethyl)-amino]-phenylamino]-methylene)-1,3-dihydro-indol-2-one 3-{[3-Methyl-4-(1,2,2,6,6-pentamethyl-piperidin-4-ylamino)-phenylamino]-methylene}-1,3-dihydro-indol-2-one 3-({3-Methyl-4-[(tetrahydro-pyran-4-ylmethyl)-amino]-phenylamino}-methylene}-1,3-dihydro-indol-2-one 4-Methyl-3-([3-methyl-4-(3-methyl-piperidin-1-yl)-phenylamino]-methylene}-1,3-dihydro-indol-2-one 3-[(4-Azocan-1-yl-3-methyl-phenylamino)-methylene]-4-methyl-1,3-dihydro-indol-2-one 4-Methyl-3-[[3-methyl-4-(3-pyridin-2-yl-pyrrolidin-1-yl)-phenylamino]-methylene}-1,3-dihydro-indol-2-one 4-Methyl-3-({3-methyl-4-[methyl-(2-pyridin-2-yl-ethyl)-amino]-phenylamino}-methylene)-1,3-dihydro-indol-2-one 3-({4-[(2-[1,3]Dioxolan-2-yl-ethyl)-methyl-amino]-3-methyl-phenylamino]-methylene)-4-methyl-1,3-dihydro-indol-2-one N-Methyl-N-(1-(2-methyl-4-[(4-methyl-2-oxo-1,2-dihydro-indol-3-ylidenemethyl)-amino]-phenyl}-pyrrolidin-3-yl)-acetamide 3-{[4-(3-Dimethylamino-propylamino)-3-methyl-phenylamino]-methylene}-4-methyl-1,3-dihydro-indol-2-one 3-{[4-(2-Dimethylamino-1-methyl-ethylamino)-3-methyl-phenylamino]-methylene}-4-methyl-1,3-dihydro-indol-2-one 3-{[4-(1-Methoxymethyl-propylamino)-3-methyl-phenylamino]-methylene}-4-methyl-1,3-dihydro-indol-2-one 3-{[4-(2-Diethylamino-ethylamino)-3-methyl-phenylamino]-methylene}-4-methyl-1,3-dihydro-indol-2-one 4-Methyl-3-{[3-methyl-4-(2-pyridin-2-yl-ethylamino)-phenylamino]-methylene}-1,3-dihydro-indol-2-one 4-Methyl-3-{[3-methyl-4-(2-pyridin-4-yl-ethylamino)-phenylamino]-methylene}-1,3-dihydro-indol-2-one 4-Methyl-3-{[3-methyl-4-(2-morpholin-4-yl-ethylamino)-phenylamino]-methylene}-1,3-dihydro-indol-2-one 4-Methyl-3-{[3-methyl-4-(3-morpholin-4-yl-propylamino)-phenylamino]-methylene}-1,3-dihydro-indol-2-one 4-Methyl-3-{[3-methyl-4-(2-piperidin-1-yl-ethylamino)-phenylamino]-methylene}-1,3-dihydro-indol-2-one 3-{[4-(2-Methoxy-1-methyl-ethylamino)-3-methyl-phenylamino]-methylene}-4-methyl-1,3-dihydro-indol-2-one 3-{[4-(2-Dimethylamino-ethylamino)-3-methyl-phenylamino]-methylene}-4-methyl-1,3-dihydro-indol-2-one 3-{[4-(3-Diethylamino-propylamino)-3-methyl-phenylamino]-methylene}-4-methyl-1,3-dihydro-indol-2-one 3-{[4-(3-Imidazol-1-yl-propylamino)-3-methyl-phenylamino]-methylene}-4-methyl-1,3-dihydro-indol-2-one 3-{[4-(2-Diisopropylamino-ethylamino)-3-methyl-phenylamino]-methylene}-4-methyl-1,3-dihydro-indol-2-one 4-Methyl-3-({3-methyl-4-[(tetrahydro-pyran-4-ylmethyl)-amino]-phenylamino}-methylene)-1,3-dihydro-indol-2-one 4-Fluoro-3-[(3-methyl-4-pyrrolidin-1-yl-phenylamino)-methylene]-1,3-dihydro-indol-2-one 1-{4-[(4-Fluoro-2-oxo-1,2-dihydro-indol-3-ylidenemethyl)-amino]-2-methyl-phenyl}-piperidine-4-carboxylic acid methyl ester 4-Fluoro-3-{[3-methyl-4-(3-methyl-piperidin-1-yl)-phenylamino]-methylene}-1,3-dihydro-indol-2-one 4-Fluoro-3-{[3-methyl-4-(4-methyl-piperidin-1-yl)-phenylamino]-methylene}-1,3-dihydro-indol-2-one 3-[(4-Azepan-1-yl-3-methyl-phenylamino)-methylene]-4-fluoro-1,3-dihydro-indol-2-one 3-[(4-Dipropylamino-3-methyl-phenylamino)-methylene]-4-fluoro-1,3-dihydro-indol-2-one 3-({4-[Ethyl-(2-methoxy-ethyl)-amino]-3-methyl-phenylamino}-methylene)-4-fluoro-1,3-dihydro-indol-2-one 3-{[4-(3,5-Dimethyl-piperidin-1-yl)-3-methyl-phenylamino]-methylene}-4-fluoro-1,3-dihydro-indol-2-one 4-{4-[(4-Fluoro-2-oxo-1,2-dihydro-indol-3-ylidenemethyl)-amino]-2-methyl-phenyl}-piperazine-1-carbaldehyde 3-{[4-(3-Dimethylamino-pyrrolidin-1-yl)-3-methyl-phenylamino]-methylene}-4-fluoro-1,3-dihydro-indol-2-one 3-{[4-(2,6-Dimethyl-morpholin-4-yl)-3-methyl-phenylamino]-methylene}-4-fluoro-1,3-dihydro-indol-2-one 4-Fluoro-3-({4-[(2-methoxy-ethyl)-propyl-amino]-3-methyl-phenylamino}-methylene)-1,3-dihydro-indol-2-one 1-{4-[(4-Fluoro-2-oxo-1,2-dihydro-indol-3-ylidenemethyl)-amino]-2-methyl-phenyl}-piperidine-3-carboxylic acid amide 1-{4-[(4-Fluoro-2-oxo-1,2-dihydro-indol-3-ylidenemethyl)-amino]-2-methyl-phenyl}-piperidine-4-carboxylic acid amide 4-Fluoro-3-{[4-(4-isopropyl-piperazin-1-yl)-3-methyl-phenylamino]-methylene}-1,3-dihydro-indol-2-one 3-{[4-(4-sec-Butyl-piperazin-1-yl)-3-methyl-phenylamino]-methylene}-4-fluoro-1,3-dihydro-indol-2-one 3-{[4-(1,4-Dioxa-8-aza-spiro[4.5]dec-8-yl)-3-methyl-phenylamino]-methylene}-4-fluoro-1,3-dihydro-indol-2-one 4-Fluoro-3-{[3-methyl-4-(3-pyridin-2-yl-pyrrolidin-1-yl)-phenylamino]-methylene}-1,3-dihydro-indol-2-one 4-Fluoro-3-{[3-methyl-4-(3-pyridin-4-yl-pyrrolidin-1-yl)-phenylamino]-methylene}-1,3-dihydro-indol-2-one 4-Fluoro-3-{[3-methyl-4-(4-propyl-piperidin-1-yl)-phenylamino]-methylene}-1,3-dihydro-indol-2-one 4-Fluoro-3-{[3-methyl-4-(2,3,5,6-tetrahydro-[1,2']bipyrazinyl-4-yl)-phenylamino]-methylene}-1,3-dihydro-indol-2-one 3-{[4-([1,3]Dioxolan-2-ylmethyl-methyl-amino)-3-methyl-phenylamino]-methylene-4-fluoro-1,3-dihydro-indol-2-one 3-({4-[(2-[1,3]Dioxolan-2-yl-ethyl)-methyl-amino]-3-methyl-phenylamino}-methylene)-4-fluoro-1,3-dihydro-indol-2-one 4-Fluoro-3-{([4-(2-methoxy-ethylamino)-3-methyl-phenylamino]-methylene}-1,3-dihydro-indol-2-one 4-Fluoro-3-([3-methyl-4-(tetrahydro-pyran-4-ylamino)-phenylamino]-methylene}-1,3-dihydro-indol-2-one 3-{[4-(3-Dimethylamino-propylamino)-3-methyl-phenylamino]-methylene}-4-fluoro-1,3-dihydro-indol-2-one 4-Fluoro-3-{([4-(1-methoxymethyl-propylamino)-3-methyl-phenylamino]-methylene}-1,3-dihydro-indol-2-one 3-{[4-(2-Diethylamino-ethylamino)-3-methyl-phenylamino]-methylene}-4-fluoro-1,3-dihydro-indol-2-one 4-Fluoro-3-{[3-methyl-4-(2-pyridin-2-yl-ethylamino)-phenylamino]-methylene}-1,3-dihydro-indol-2-one 4-Fluoro-3-{[3-methyl-4-(2-pyridin-4-yl-ethylamino)-phenylamino]-methylene-1,3-dihydro-indol-2-one 4-Fluoro-3-{[3-methyl-4-(2-pyridin-3-yl-ethylamino)-phenylamino]-methylene-1,3-dihydro-indol-2-one 4-Fluoro-3-{[3-methyl-4-(3-morpholin-4-yl-propylamino)-phenylamino]-methylene}-1,3-dihydro-indol-2-one 4-Fluoro-3-({3-methyl-4-[(pyridin-2-ylmethyl)-amino]-phenylamino}-methylene)-1,3-dihydro-indol-2-one 4-Fluoro-3-({3-methyl-4-[(pyridin-3-ylmethyl)-amino]-phenylamino}-methylene)-1,3-dihydro-indol-2-one 4-Fluoro-3-{[3-methyl-4-(2-piperidin-1-yl-ethylamino)-phenylamino]-methylene}-1,3-dihydro-indol-2-one 4-Fluoro-3-({3-methyl-4-[3-(2-methyl-piperidin-1-yl)-propylamino]-phenylamino}-methylene)-1,3-dihydro-indol-2-one 4-Fluoro-3-{[4-(2-methoxy-1-methyl-ethylamino)-3-methyl-phenylamino]-methylene}-1,3-dihydro-indol-2-one 3-{[4-(3-Diethylamino-propylamino)-3-methyl-phenylamino]-methylene}-4-fluoro-1,3-dihydro-indol-2-one 4-Fluoro-3-({4-[2-(1H-imidazol-4-yl)-ethylamino]-3-methyl-phenylamino}-methylene)-1,3-dihydro-indol-2-one 3-{[4-(2-Diisopropylamino-ethylamino)-3-methyl-phenylamino]-methylene}-4-fluoro-1,3-dihydro-indol-2-one 4-Fluoro-3-({3-methyl-4-[(5-methyl-pyrazin-2-ylmethyl)-amino]-phenylamino}-methylene)-1,3-dihydro-indol-2-one 3-({4-[(2,2-Dimethyl-[1,3]dioxolan-4-ylmethyl)-amino]-3-methyl-phenylamino}-methylene)-4-fluoro-1,3-dihydro-indol-2-one 3-{4-[(4-Fluoro-2-oxo-1,2-dihydro-indol-3-ylidenemethyl)-amino]-2-methyl-phenylamino}-pyrrolidine-1-carboxylic acid tert-butyl ester 4-Fluoro-3-{([3-methyl-4-(1,2,2,6,6-pentamethyl-piperidin-4-ylamino)-phenylamino]-methylene}-1,3-dihydro-indol-2-one 4-Fluoro-3-({3-methyl-4-[(tetrahydro-pyran-4-ylmethyl)-amino]-phenylamino}-methylene)-1,3-dihydro-indol-2-one 4-Fluoro-3-{[4-(2-hydroxy-ethylamino)-3-methyl-phenylamino]-methylene}-1,3-dihydro-indol-2-one 3-{[4-(2-Diethylamino-1-methyl-ethylamino)-3-methyl-phenylamino]-methylene}-4-fluoro-1,3-dihydro-indol-2-one 5-Fluoro-3-[(3-methyl-4-pyrrolidin-1-yl-phenylamino)-methylene]-1,3-dihydro-indol-2-one 1-{4-[(5-Fluoro-2-oxo-1,2-dihydro-indol-3-ylidenemethyl)-amino]-2-methyl-phenyl}-piperidine-4-carboxylic acid methyl ester 5-Fluoro-3-{[3-methyl-4-(4-methyl-piperidin-1-yl)-phenylamino]-methylene}-1,3-dihydro-indol-2-one 3-[(4-Azocan-1-yl-3-methyl-phenylamino)-methylene]-5-fluoro-1,3-dihydro-indol-2-one 3-{[4-(3,5-Dimethyl-piperidin-1-yl)-3-methyl-phenylamino]-methylene}-5-fluoro-1,3-dihydro-indol-2-one 4-{4-[(5-Fluoro-2-oxo-1,2-dihydro-indol-3-ylidenemethyl)-amino]-2-methyl-phenyl}-piperazine-1-carbaldehyde 3-{[4-(3-Dimethylamino-pyrrolidin-1-yl)-3-methyl-phenylamino]-methylene}-5-fluoro-1,3-dihydro-indol-2-one 1-{4-[(5-Fluoro-2-oxo-1,2-dihydro-indol-3-ylidenemethyl)-amino]-2-methyl-phenyl}-piperidine-3-carboxylic acid amide 1-{4-[(5-Fluoro-2-oxo-1,2-dihydro-indol-3-ylidenemethyl)-amino]-2-methyl-phenyl-piperidine-4-carboxylic acid amide 5-Fluoro-3-{[3-methyl-4-(octahydro-isoquinolin-2-yl)-phenylamino]-methylene}-1,3-dihydro-indol-2-one 3-{[4-(4-Butyl-piperazin-1-yl)-3-methyl-phenylamino]-methylene}-5-fluoro-1,3-dihydro-indol-2-one 3-{[4-(4-sec-Butyl-piperazin-1-yl)-3-methyl-phenylamino]-methylene}-5-fluoro-1,3-dihydro-indol-2-one 3-{[4-(3-Diethylamino-pyrrolidin-1-yl)-3-methyl-phenylamino]-methylene}-5-fluoro-1,3-dihydro-indol-2-one 5-Fluoro-3-{[3-methyl-4-(3-pyridin-2-yl-pyrrolidin-1-yl)-phenylamino]-methylene}-1,3-dihydro-indol-2-one 5-Fluoro-3-{[3-methyl-4-(3-pyridin-4-yl-pyrrolidin-1-yl)-phenylamino]-methylene}-1,3-dihydro-indol-2-one 5-Fluoro-3-([3-methyl-4-(4-propyl-piperidin-1-yl)-phenylamino]-methylene}-1,3-dihydro-indol-2-one 3-{[4-(3-Dimethylamino-propylamino)-3-methyl-phenylamino]-methylene}-5-fluoro-1,3-dihydro-indol-2-one 3-{[4-(2-Dimethylamino-1-methyl-ethylamino)-3-methyl-phenylamino]-methylene}-5-fluoro-1,3-dihydro-indol-2-one 5-Fluoro-3-{[4-(1-methoxymethyl-propylamino)-3-methyl-phenylamino]-methylene}-1,3-dihydro-indol-2-one 3-{[4-(2-Diethylamino-ethylamino)-3-methyl-phenylamino]-methylene}-5-fluoro-1,3-dihydro-indol-2-one 5-Fluoro-3-{[3-methyl-4-(2-pyridin-4-yl-ethylamino)-phenylamino]-methylene}-1,3-dihydro-indol-2-one 5-Fluoro-3-{[3-methyl-4-(2-pyridin-3-yl-ethylamino)-phenylamino]-methylene}-1,3-dihydro-indol-2-one 5-Fluoro-3-{[3-methyl-4-(2-morpholin-4-yl-ethylamino)-phenylamino]-methylene}-1,3-dihydro-indol-2-one 5-Fluoro-3-{[3-methyl-4-(3-morpholin-4-yl-propylamino)-phenylamino]-methylene}-1,3-dihydro-indol-2-one
5-Fluoro-3-({3-methyl-4-[(pyridin-4-ylmethyl)-amino]-phenylamino}-methylene)-1,3-dihydro-indol-2-one
5-Fluoro-3-{[3-methyl-4-(2-piperidin-1-yl-ethylamino)-phenylamino]-methylene}-1,3-dihydro-indol-2-one
5-Fluoro-3-({3-methyl-4-[3-(2-methyl-piperidin-1-yl)-propylamino]-phenylamino}-methylene)-1,3-dihydro-indol-2-one
5-Fluoro-3-{[4-(2-methoxy-1-methyl-ethylamino)-3-methyl-phenylamino]-methylene}-1,3-dihydro-indol-2-one
3-{[4-(2-Dimethylamino-ethylamino)-3-methyl-phenylamino]-methylene}-5-fluoro-1,3-dihydro-indol-2-one
3-{[4-(3-Diethylamino-propylamino)-3-methyl-phenylamino]-methylene}-5-fluoro-1,3-dihydro-indol-2-one
5-Fluoro-3-{[4-(3-imidazol-1-yl-propylamino)-3-methyl-phenylamino]-methylene}-1,3-dihydro-indol-2-one
5-Fluoro-3-({4-[2-(1H-imidazol-4-yl)-ethylamino]-3-methyl-phenylamino}-methylene)-1,3-dihydro-indol-2-one
3-{[4-(2-Diisopropylamino-ethylamino)-3-methyl-phenylamino]-methylene}-5-fluoro-1,3-dihydro-indol-2-one
3-{[4-(1-Benzyl-pyrrolidin-3-ylamino)-3-methyl-phenylamino]-methylene}-5-fluoro-1,3-dihydro-indol-2-one
5-Fluoro-3-({3-methyl-4-[(5-methyl-pyrazin-2-ylmethyl)-amino]-phenylamino}-methylene)-1,3-dihydro-indol-2-one
3-({4-[(2,2-Dimethyl-[1,3]dioxolan-4-ylmethyl)-amino]-3-methyl-phenylamino}-methylene)-5-fluoro-1,3-dihydro-indol-2-one
5-Fluoro-3-{[3-methyl-4-(1,2,2,6,6-pentamethyl-piperidin-4-ylamino)-phenylamino]-methylene}-1,3-dihydro-indol-2-one
5-Fluoro-3-({3-methyl-4-[(tetrahydro-pyran-4-ylmethyl)-amino]-phenylamino}-methylene)-1,3-dihydro-indol-2-one
3-{[4-(2-Diethylamino-1-methyl-ethylamino)-3-methyl-phenylamino]-methylene}-5-fluoro-1,3-dihydro-indol-2-one
6-Fluoro-3-[(3-methyl-4-pyrrolidin-1-yl-phenylamino)-methylene]-1,3-dihydro-indol-2-one
1-{4-[(6-Fluoro-2-oxo-1,2-dihydro-indol-3-ylidenemethyl)-amino]-2-methyl-phenyl}-piperidine-4-carboxylic acid methyl ester
6-Fluoro-3-{[3-methyl-4-(4-methyl-piperidin-1-yl)-phenylamino]-methylene}-1,3-dihydro-indol-2-one
3-{[4-(3,5-Dimethyl-piperidin-1-yl)-3-methyl-phenylamino]-methylene}-6-fluoro-1,3-dihydro-indol-2-one
4-{4-[(6-Fluoro-2-oxo-1,2-dihydro-indol-3-ylidenemethyl)-amino]-2-methyl-phenyl}-piperazine-1-carbaldehyde
3-{[4-(3-Dimethylamino-pyrrolidin-1-yl)-3-methyl-phenylamino]-methylene}-6-fluoro-1,3-dihydro-indol-2-one
1-{4-[(6-Fluoro-2-oxo-1,2-dihydro-indol-3-ylidenemethyl)-amino]-2-methyl-phenyl}-piperidine-3-carboxylic acid amide
1-{4-[(6-Fluoro-2-oxo-1,2-dihydro-indol-3-ylidenemethyl)-amino]-2-methyl-phenyl}-piperidine-4-carboxylic acid amide
3-{[4-(4-Butyl-piperazin-1-yl)-3-methyl-phenylamino]-methylene}-6-fluoro-1,3-dihydro-indol-2-one
3-{[4-(4-sec-Butyl-piperazin-1-yl)-3-methyl-phenylamino]-methylene}-6-fluoro-1,3-dihydro-indol-2-one
3-{[4-(3-Diethylamino-pyrrolidin-1-yl)-3-methyl-phenylamino]-methylene}-6-fluoro-1,3-dihydro-indol-2-one
6-Fluoro-3-({4-[4-(2-methoxy-ethyl)-piperazin-1-yl]-3-methyl-phenylamino}-methylene)-1,3-dihydro-indol-2-one
6-Fluoro-3-[({3-methyl-4-(4-propyl-piperidin-1-yl)-phenylamino]-methylene}-1,3-dihydro-indol-2-one
6-Fluoro-3-{[3-methyl-4-(2,3,5,6-tetrahydro-[1,2']bipyrazinyl-4-yl)-phenylamino]-methylene}-1,3-dihydro-indol-2-one
3-({4-[(2-[1,3]Dioxolan-2-yl-ethyl)-methyl-amino]-3-methyl-phenylamino}-methylene)-6-fluoro-1,3-dihydro-indol-2-one
3-{[4-(3-Dimethylamino-propylamino)-3-methyl-phenylamino]-methylene}-6-fluoro-1,3-dihydro-indol-2-one
3-{[4-(2-Dimethylamino-1-methyl-ethylamino)-3-methyl-phenylamino]-methylene}-6-fluoro-1,3-dihydro-indol-2-one
6-Fluoro-3-{[4-(1-methoxymethyl-propylamino)-3-methyl-phenylamino]-methylene}-1,3-dihydro-indol-2-one
3-{[4-(2-Diethylamino-ethylamino)-3-methyl-phenylamino]-methylene}-6-fluoro-1,3-dihydro-indol-2-one
6-Fluoro-3-{[3-methyl-4-(2-pyridin-2-yl-ethylamino)-phenylamino]-methylene}-1,3-dihydro-indol-2-one
6-Fluoro-3-{[3-methyl-4-(2-morpholin-4-yl-ethylamino)-phenylamino]-methylene}-1,3-dihydro-indol-2-one
6-Fluoro-3-{[3-methyl-4-(3-morpholin-4-yl-propylamino)-phenylamino]-methylene}-1,3-dihydro-indol-2-one
6-Fluoro-3-({3-methyl-4-[(pyridin-2-ylmethyl)-amino]-phenylamino}-methylene)-1,3-dihydro-indol-2-one
6-Fluoro-3-({3-methyl-4-[(pyridin-4-ylmethyl)-amino]-phenylamino}-methylene)-1,3-dihydro-indol-2-one
6-Fluoro-3-{[3-methyl-4-(2-piperidin-1-yl-ethylamino)-phenylamino]-methylene}-1,3-dihydro-indol-2-one
6-Fluoro-3-({3-methyl-4-[3-(2-methyl-piperidin-1-yl)-propylamino]-phenylamino}-methylene)-1,3-dihydro-indol-2-one
6-Fluoro-3-{[4-(2-methoxy-1-methyl-ethylamino)-3-methyl-phenylamino]-methylene}-1,3-dihydro-indol-2-one
3-{[4-(2-Dimethylamino-ethylamino)-3-methyl-phenylamino]-methylene}-6-fluoro-1,3-dihydro-indol-2-one
3-{[4-(3-Diethylamino-propylamino)-3-methyl-phenylamino]-methylene}-6-fluoro-1,3-dihydro-indol-2-one
3-{[4-(2-Diisopropylamino-ethylamino)-3-methyl-phenylamino]-methylene}-6-fluoro-1,3-dihydro-indol-2-one
6-Fluoro-3-({3-methyl-4-[(5-methyl-pyrazin-2-ylmethyl)-amino]-phenylamino}-methylene)-1,3-dihydro-indol-2-one
3-({4-[(2,2-Dimethyl-[1,3]dioxolan-4-ylmethyl)-amino]-3-methyl-phenylamino}-methylene)-6-fluoro-1,3-dihydro-indol-2-one
6-Fluoro-3-{[3-methyl-4-(1,2,2,6,6-pentamethyl-piperidin-4-ylamino)-phenylamino]-methylene}-1,3-dihydro-indol-2-one
6-Fluoro-3-({3-methyl-4-[(tetrahydro-pyran-4-ylmethyl)-amino]-phenylamino}-methylene)-1,3-dihydro-indol-2-one
3-{[4-(2-Diethylamino-1-methyl-ethylamino)-3-methyl-phenylamino]-methylene}-6-fluoro-1,3-dihydro-indol-2-one
3-[(4-Pyrrolidin-1-yl-3-trifluoromethyl-phenylamino)-methylene]-1,3-dihydro-indol-2-one
1-{4-[(2-Oxo-1,2-dihydro-indol-3-ylidenemethyl)-amino]-2-trifluoromethyl-phenyl-piperidine-4-carboxylic acid methyl ester
3-{[4-(3,6-Dihydro-2H-pyridin-1-yl)-3-trifluoromethyl-phenylamino]-methylene}-1,3-dihydro-indol-2-one
3-[(4-Morpholin-4-yl-3-trifluoromethyl-phenylamino)-methylene]-1,3-dihydro-indol-2-one
3-({4-(3-Methyl-piperidin-1-yl)-3-trifluoromethyl-phenylamino]-methylene}-1,3-dihydro-indol-2-one
3-({4-(4-Methyl-piperidin-1-yl)-3-trifluoromethyl-phenylamino]-methylene}-1,3-dihydro-indol-2-one 3-[(4-Azepan-1-yl-3-trifluoromethyl-phenylamino)-methylene]-1,3-dihydro-indol-2-one
3-{[4-(4-Methyl-piperazin-1-yl)-3-trifluoromethyl-phenylamino]-methylene}-1,3-dihydro-indol-2-one
3-[(4-Azocan-1-yl-3-trifluoromethyl-phenylamino)-methylene]-1,3-dihydro-indol-2-one
3-{[4-(3,5-Dimethyl-piperidin-1-yl)-3-trifluoromethyl-phenylamino]-methylene}-1,3-dihydro-indol-2-one
4-{4-[(2-Oxo-1,2-dihydro-indol-3-ylidenemethyl)-amino]-2-trifluoromethyl-phenyl}-piperazine-1-carbaldehyde
3-{[4-(2,6-Dimethyl-morpholin-4-yl)-3-trifluoromethyl-phenylamino]-methylene}-1,3-dihydro-indol-2-one
3-{[4-(2,6-Dimethyl-morpholin-4-yl)-3-trifluoromethyl-phenylamino]-methylene}-1,3-dihydro-indol-2-one
3-({4-[(2-Methoxy-ethyl)-propyl-amino]-3-trifluoromethyl-phenylamino}-methylene)-1,3-dihydro-indol-2-one
3-{[4-(1,3-Dihydro-isoindol-2-yl)-3-trifluoromethyl-phenylamino]-methylene}-1,3-dihydro-indol-2-one
1-{4-[(2-Oxo-1,2-dihydro-indol-3-ylidenemethyl)-amino]-2-trifluoromethyl-phenyl}-piperidine-4-carboxylic acid amide
3-{[4-(4-Acetyl-piperazin-1-yl)-3-trifluoromethyl-phenylamino]-methylene}-1,3-dihydro-indol-2-one
3-{[4-(Octahydro-isoquinolin-2-yl)-3-trifluoromethyl-phenylamino]-methylene}-1,3-dihydro-indol-2-one
3-{[4-(4-sec-Butyl-piperazin-1-yl)-3-trifluoromethyl-phenylamino]-methylene}-1,3-dihydro-indol-2-one
3-{[4-(4-Pyrimidin-2-yl-piperazin-1-yl)-3-trifluoromethyl-phenylamino]-methylene}-1,3-dihydro-indol-2-one
3-{[4-([1,3]Dioxolan-2-ylmethyl-methyl-amino)-3-trifluoromethyl-phenylamino]-methylene}-1,3-dihydro-indol-2-one
N-Methyl-N-(1-{4-[(2-oxo-1,2-dihydro-indol-3-ylidenemethyl)-amino]-2-trifluoromethyl-phenyl}-pyrrolidin-3-yl)-acetamide
3-{[4-(2-Methoxy-ethylamino)-3-trifluoromethyl-phenylamino]-methylene}-1,3-dihydro-indol-2-one
3-({4-[(Tetrahydro-furan-2-ylmethyl)-amino]-3-trifluoromethyl-phenylamino}-methylene)-1,3-dihydro-indol-2-one
3-{[4-(Tetrahydro-pyran-4-ylamino)-3-trifluoromethyl-phenylamino]-methylene}-1,3-dihydro-indol-2-one
3-{[4-(3-Dimethylamino-propylamino)-3-trifluoromethyl-phenylamino]-methylene}-1,3-dihydro-indol-2-one
3-{[4-(2-Dimethylamino-1-methyl-ethylamino)-3-trifluoromethyl-phenylamino]-methylene}-1,3-dihydro-indol-2-one
3-{[4-(1-Methoxymethyl-propylamino)-3-trifluoromethyl-phenylamino]-methylene}-1,3-dihydro-indol-2-one
3-{[4-(2-Diethylamino-ethylamino)-3-trifluoromethyl-phenylamino]-methylene}-1,3-dihydro-indol-2-one
3-{[4-(2-Pyridin-2-yl-ethylamino)-3-trifluoromethyl-phenylamino]-methylene}-1,3-dihydro-indol-2-one
3-{[4-(2-Pyridin-4-yl-ethylamino)-3-trifluoromethyl-phenylamino]-methylene}-1,3-dihydro-indol-2-one
3-{[4-(2-Pyridin-3-yl-ethylamino)-3-trifluoromethyl-phenylamino]-methylene}-1,3-dihydro-indol-2-one
3-{[4-(2-Morpholin-4-yl-ethylamino)-3-trifluoromethyl-phenylamino]-methylene}-1,3-dihydro-indol-2-one
3-{[4-(3-Morpholin-4-yl-propylamino)-3-trifluoromethyl-phenylamino]-methylene}-1,3-dihydro-indol-2-one
3-({4-[(Pyridin-2-ylmethyl)-amino]-3-trifluoromethyl-phenylamino}-methylene)-1,3-dihydro-indol-2-one
3-({4-[(Pyridin-3-ylmethyl)-amino]-3-trifluoromethyl-phenylamino}-methylene)-1,3-dihydro-indol-2-one
3-{[4-(2-Piperidin-1-yl-ethylamino)-3-trifluoromethyl-phenylamino]-methylene}-1,3-dihydro-indol-2-one
3-({4-[3-(2-Methyl-piperidin-1-yl)-propylamino]-3-trifluoromethyl-phenylamino}-methylene)-1,3-dihydro-indol-2-one
3-{[4-(2-Methoxy-1-methyl-ethylamino)-3-trifluoromethyl-phenylamino]-methylene}-1,3-dihydro-indol-2-one
3-{[4-(2-Dimethylamino-ethylamino)-3-trifluoromethyl-phenylamino]-methylene}-1,3-dihydro-indol-2-one
3-{[4-(3-Diethylamino-propylamino)-3-trifluoromethyl-phenylamino]-methylene}-1,3-dihydro-indol-2-one
3-{[4-(2-Diisopropylamino-ethylamino)-3-trifluoromethyl-phenylamino]-methylene}-1,3-dihydro-indol-2-one
3-{[4-(1-Benzyl-pyrrolidin-3-ylamino)-3-trifluoromethyl-phenylamino]-methylene}-1,3-dihydro-indol-2-one
3-({4-[(5-Methyl-pyrazin-2-ylmethyl)-amino]-3-trifluoromethyl-phenylamino}-methylene)-1,3-dihydro-indol-2-one
3-({4-[(2,2-Dimethyl-[1,3]dioxolan-4-ylmethyl)-amino]-3-trifluoromethyl-phenylamino}-methylene)-1,3-dihydro-indol-2-one
3-{4-[(2-Oxo-1,2-dihydro-indol-3-ylidenemethyl)-amino]-2-trifluoromethyl-phenylamino}-pyrrolidine-1-carboxylic acid tert-butyl ester
3-({4-[(Tetrahydro-pyran-4-ylmethyl)-amino]-3-trifluoromethyl-phenylamino}-methylene)-1,3-dihydro-indol-2-one
3-{[4-(2-Hydroxy-ethylamino)-3-trifluoromethyl-phenylamino]-methylene-1,3-dihydro-indol-2-one
3-{[4-(2-Diethylamino-1-methyl-ethylamino)-3-trifluoromethyl-phenylamino]-methylene}-1,3-dihydro-indol-2-one
4-Methyl-3-[(4-pyrrolidin-1-yl-3-trifluoromethyl-phenylamino)-methylene]-1,3-dihydro-indol-2-one
3-({4-[(2-Methoxy-ethyl)-methyl-amino]-3-trifluoromethyl-phenylamino}-methylene)-4-methyl-1,3-dihydro-indol-2-one
4-Methyl-3-[(4-morpholin-4-yl-3-trifluoromethyl-phenylamino)-methylene]-1,3-dihydro-indol-2-one
3-[(4-Dipropylamino-3-trifluoromethyl-phenylamino)-methylene]-4-methyl-1,3-dihydro-indol-2-one
3-{[4-(Butyl-ethyl-amino)-3-trifluoromethyl-phenylamino]-methylene}-4-methyl-1,3-dihydro-indol-2-one
4-Methyl-3-[(4-thiomorpholin-4-yl-3-trifluoromethyl-phenylamino)-methylene]-1,3-dihydro-indol-2-one
3-[(4-Azocan-1-yl-3-trifluoromethyl-phenylamino)-methylene]-4-methyl-1,3-dihydro-indol-2-one
3-{[4-(2,6-Dimethyl-morpholin-4-yl)-3-trifluoromethyl-phenylamino]-methylene}-4-methyl-1,3-dihydro-indol-2-one
3-{[4-(2,6-Dimethyl-morpholin-4-yl)-3-trifluoromethyl-phenylamino]-methylene}-4-methyl-1,3-dihydro-indol-2-one
3-{[4-(1,3-Dihydro-isoindol-2-yl)-3-trifluoromethyl-phenylamino]-methylene}-4-methyl-1,3-dihydro-indol-2-one
3-{[4-(4-Acetyl-piperazin-1-yl)-3-trifluoromethyl-phenylamino]-methylene}-4-methyl-1,3-dihydro-indol-2-one
4-Methyl-3-{[4-(octahydro-isoquinolin-2-yl)-3-trifluoromethyl-phenylamino]-methylene}-1,3-dihydro-indol-2-one
4-Methyl-3-{[4-(octahydro-isoquinolin-2-yl)-3-trifluoromethyl-phenylamino]-methylene}-1,3-dihydro-indol-2-one
3-{[4-(1,4-Dioxa-8-aza-spiro[4.5]dec-8-yl)-3-trifluoromethyl-phenylamino]-methylene}-4-methyl-1,3-dihydro-indol-2-one
4-Methyl-3-{[4-(3-pyridin-2-yl-pyrrolidin-1-yl)-3-trifluoromethyl-phenylamino]-methylene}-1,3-dihydro-indol-2-one
3-{[4-(2-Methoxy-ethylamino)-3-trifluoromethyl-phenylamino]-methylene}-4-methyl-1,3-dihydro-indol-2-one
4-Methyl-3-{[4-(tetrahydro-pyran-4-ylamino)-3-trifluoromethyl-phenylamino]-methylene}-1,3-dihydro-indol-2-one 3-{[4-(1-Methoxymethyl-propylamino)-3-trifluoromethyl-phenylamino]-methylene}-4-methyl-1,3-dihydro-indol-2-one
4-Methyl-3-{[4-(2-pyridin-2-yl-ethylamino)-3-trifluoromethyl-phenylamino]-methylene}-1,3-dihydro-indol-2-one
4-Methyl-3-{[4-(2-pyridin-4-yl-ethylamino)-3-trifluoromethyl-phenylamino]-methylene)-1,3-dihydro-indol-2-one
3-{[4-(2-Methoxy-1-methyl-ethylamino)-3-trifluoromethyl-phenylamino]-methylene}-4-methyl-1,3-dihydro-indol-2-one
3-({4-[(2,2-Dimethyl-[1,3]dioxolan-4-ylmethyl)-amino]-3-trifluoromethyl-phenylamino}-methylene)-4-methyl-1,3-dihydro-indol-2-one
4-Fluoro-3-[(4-morpholin-4-yl-3-trifluoromethyl-phenylamino)-methylene]-1,3-dihydro-indol-2-one
4-Fluoro-3-{[4-(3-methyl-piperidin-1-yl)-3-trifluoromethyl-phenylamino]-methylene}-1,3-dihydro-indol-2-one
4-Fluoro-3-{[4-(4-methyl-piperidin-1-yl)-3-trifluoromethyl-phenylamino]-methylene}-1,3-dihydro-indol-2-one
3-[(4-Azepan-1-yl-3-trifluoromethyl-phenylamino)-methylene]-4-fluoro-1,3-dihydro-indol-2-one
4-Fluoro-3-{[4-(4-methyl-piperazin-1-yl)-3-trifluoromethyl-phenylamino]-methylene}-1,3-dihydro-indol-2-one
3-[(4-Dipropylamino-3-trifluoromethyl-phenylamino)-methylene]-4-fluoro-1,3-dihydro-indol-2-one
3-{[4-(Butyl-ethyl-amino)-3-trifluoromethyl-phenylamino]-methylene}-4-fluoro-1,3-dihydro-indol-2-one
3-({4-[Ethyl-(2-methoxy-ethyl)-amino]-3-trifluoromethyl-phenylamino}-methylene)-4-fluoro-1,3-dihydro-indol-2-one
4-Fluoro-3-[(4-thiomorpholin-4-yl-3-trifluoromethyl-phenylamino)-methylene]-1,3-dihydro-indol-2-one
3-[({4-(Cyclopropylmethyl-propyl-amino)-3-trifluoromethyl-phenylamino]-methylene}-4-fluoro-1,3-dihydro-indol-2-one
3-[(4-Azocan-1-yl-3-trifluoromethyl-phenylamino)-methylene]-4-fluoro-1,3-dihydro-indol-2-one
3-{[4-(3,5-Dimethyl-piperidin-1-yl)-3-trifluoromethyl-phenylamino]-methylene}-4-fluoro-1,3-dihydro-indol-2-one
3-{[4-(3,5-Dimethyl-piperazin-1-yl)-3-trifluoromethyl-phenylamino]-methylene}-4-fluoro-1,3-dihydro-indol-2-one
3-{[4-(4-Ethyl-piperazin-1-yl)-3-trifluoromethyl-phenylamino]-methylene}-4-fluoro-1,3-dihydro-indol-2-one
3-{[4-(2,6-Dimethyl-morpholin-4-yl)-3-trifluoromethyl-phenylamino]-methylene}-4-fluoro-1,3-dihydro-indol-2-one
3-{[4-(2,6-Dimethyl-morpholin-4-yl)-3-trifluoromethyl-phenylamino]-methylene}-4-fluoro-1,3-dihydro-indol-2-one
3-{[4-(1,3-Dihydro-isoindol-2-yl)-3-trifluoromethyl-phenylamino]-methylene}-4-fluoro-1,3-dihydro-indol-2-one
3-{[4-(4-Acetyl-piperazin-1-yl)-3-trifluoromethyl-phenylamino]-methylene}-4-fluoro-1,3-dihydro-indol-2-one
4-Fluoro-3-{[4-(4-isopropyl-piperazin-1-yl)-3-trifluoromethyl-phenylamino]-methylene}-1,3-dihydro-indol-2-one
4-Fluoro-3-[4-(octahydro-isoquinolin-2-yl)-3-trifluoromethyl-phenylamino]-methylene}-1,3-dihydro-indol-2-one
4-Fluoro-3-{[4-(octahydro-isoquinolin-2-yl)-3-trifluoromethyl-phenylamino]-methylene}-1,3-dihydro-indol-2-one
4-Fluoro-3-({4-[4-(2-methoxy-ethyl)-piperazin-1-yl]-3-trifluoromethyl-phenylamino}-methylene)-1,3-dihydro-indol-2-one
4-Fluoro-3-{[4-(3-pyridin-2-yl-pyrrolidin-1-yl)-3-trifluoromethyl-phenylamino]-methylene}-1,3-dihydro-indol-2-one
4-Fluoro-3-{[4-(4-propyl-piperidin-1-yl)-3-trifluoromethyl-phenylamino]-methylene}-1,3-dihydro-indol-2-one
3-{[4-([1,3]Dioxolan-2-ylmethyl-methyl-amino)-3-trifluoromethyl-phenylamino]-methylene}-4-fluoro-1,3-dihydro-indol-2-one
4-Fluoro-3-{[4-(2-methoxy-ethylamino)-3-trifluoromethyl-phenylamino]-methylene}-1,3-dihydro-indol-2-one
4-Fluoro-3-({4-[(tetrahydro-furan-2-ylmethyl)-amino]-3-trifluoromethyl-phenylamino}-methylene)-1,3-dihydro-indol-2-one
4-Fluoro-3-{[4-(tetrahydro-pyran-4-ylamino)-3-trifluoromethyl-phenylamino]-methylene}-1,3-dihydro-indol-2-one
3-{[4-(3-Dimethylamino-propylamino)-3-trifluoromethyl-phenylamino]-methylene}-4-fluoro-1,3-dihydro-indol-2-one
3-{[4-(2-Dimethylamino-1-methyl-ethylamino)-3-trifluoromethyl-phenylamino]-methylene}-4-fluoro-1,3-dihydro-indol-2-one
4-Fluoro-3-{[4-(1-methoxymethyl-propylamino)-3-trifluoromethyl-phenylamino]-methylene}-1,3-dihydro-indol-2-one
4-Fluoro-3-{[4-(2-pyridin-4-yl-ethylamino)-3-trifluoromethyl-phenylamino]-methylene}-1,3-dihydro-indol-2-one
4-Fluoro-3-{[4-(2-piperidin-1-yl-ethylamino)-3-trifluoromethyl-phenylamino]-methylene}-1,3-dihydro-indol-2-one
4-Fluoro-3-({4-[3-(2-methyl-piperidin-1-yl)-propylamino]-3-trifluoromethyl-phenylamino}-methylene)-1,3-dihydro-indol-2-one
4-Fluoro-3-{[4-(2-methoxy-1-methyl-ethylamino)-3-trifluoromethyl-phenylamino]-methylene}-1,3-dihydro-indol-2-one
3-{[4-(2-Dimethylamino-ethylamino)-3-trifluoromethyl-phenylamino]-methylene}-4-fluoro-1,3-dihydro-indol-2-one
3-{[4-(3-Diethylamino-propylamino)-3-trifluoromethyl-phenylamino]-methylene}-4-fluoro-1,3-dihydro-indol-2-one
3-{[4-(2-Diisopropylamino-ethylamino)-3-trifluoromethyl-phenylamino]-methylene}-4-fluoro-1,3-dihydro-indol-2-one
3-{[4-(2-Diisopropylamino-ethylamino)-3-trifluoromethyl-phenylamino]-methylene}-4-fluoro-1,3-dihydro-indol-2-one
4-Fluoro-3-({4-[(5-methyl-pyrazin-2-ylmethyl)-amino]-3-trifluoromethyl-phenylamino}-methylene)-1,3-dihydro-indol-2-one
3-({4-[(2,2-Dimethyl-[1,3]dioxolan-4-ylmethyl)-amino]-3-trifluoromethyl-phenylamino}-methylene)-4-fluoro-1,3-dihydro-indol-2-one
4-Fluoro-3-({4-[(tetrahydro-pyran-4-ylmethyl)-amino]-3-trifluoromethyl-phenylamino}-methylene)-1,3-dihydro-indol-2-one
3-{[4-(2-Diethylamino-1-methyl-ethylamino)-3-trifluoromethyl-phenylamino]-methylene}-4-fluoro-1,3-dihydro-indol-2-one
3-{[4-(3,6-Dihydro-2H-pyridin-1-yl)-3-trifluoromethyl-phenylamino]-methylene}-5-fluoro-1,3-dihydro-indol-2-one
5-Fluoro-3-[(4-morpholin-4-yl-3-trifluoromethyl-phenylamino)-methylene]-1,3-dihydro-indol-2-one
3-[(4-Azepan-1-yl-3-trifluoromethyl-phenylamino)-methylene]-5-fluoro-1,3-dihydro-indol-2-one
5-Fluoro-3-{[4-(4-methyl-piperazin-1-yl)-3-trifluoromethyl-phenylamino]-methylene}-1,3-dihydro-indol-2-one
3-[(4-Dipropylamino-3-trifluoromethyl-phenylamino)-methylene]-5-fluoro-1,3-dihydro-indol-2-one
3-{[4-(Butyl-ethyl-amino)-3-trifluoromethyl-phenylamino]-methylene}-5-fluoro-1,3-dihydro-indol-2-one 3-({4-[Ethyl-(2-methoxy-ethyl)-amino]-3-trifluoromethyl-phenylamino}-methylene)-5-fluoro-1,3-dihydro-indol-2-one
3-{[4-(Cyclopropylmethyl-propyl-amino)-3-trifluoromethyl-phenylamino]-methylene}-5-fluoro-1,3-dihydro-indol-2-one
3-[(4-Azocan-1-yl-3-trifluoromethyl-phenylamino)-methylene]-5-fluoro-1,3-dihydro-indol-2-one
3-{[4-(3,5-Dimethyl-piperidin-1-yl)-3-trifluoromethyl-phenylamino]-methylene}-5-fluoro-1,3-dihydro-indol-2-one
5-Fluoro-3-{[4-(5-oxo-[1,4]diazepan-1-yl)-3-trifluoromethyl-phenylamino]-methylene}-1,3-dihydro-indol-2-one
5-Fluoro-3-{[4-(4-methyl-[1,4]diazepan-1-yl)-3-trifluoromethyl-phenylamino]-methylene}-1,3-dihydro-indol-2-one
3-{[4-(4-Ethyl-piperazin-1-yl)-3-trifluoromethyl-phenylamino]-methylene}-5-fluoro-1,3-dihydro-indol-2-one
3-{[4-(3-Dimethylamino-pyrrolidin-1-yl)-3-trifluoromethyl-phenylamino]-methylene}-5-fluoro-1,3-dihydro-indol-2-one
3-{[4-(2,6-Dimethyl-morpholin-4-yl)-3-trifluoromethyl-phenylamino]-methylene}-5-fluoro-1,3-dihydro-indol-2-one
3-{[4-(2,6-Dimethyl-morpholin-4-yl)-3-trifluoromethyl-phenylamino]-methylene}-5-fluoro-1,3-dihydro-indol-2-one
3-{[4-(1,3-Dihydro-isoindol-2-yl)-3-trifluoromethyl-phenylamino]-methylene}-5-fluoro-1,3-dihydro-indol-2-one
3-{[4-(4-Acetyl-piperazin-1-yl)-3-trifluoromethyl-phenylamino]-methylene}-5-fluoro-1,3-dihydro-indol-2-one
3-{[4-(4-Butyl-piperazin-1-yl)-3-trifluoromethyl-phenylamino]-methylene}-5-fluoro-1,3-dihydro-indol-2-one
3-{[4-(1,4-Dioxa-8-aza-spiro[4.5]dec-8-yl)-3-trifluoromethyl-phenylamino]-methylene}-5-fluoro-1,3-dihydro-indol-2-one
5-Fluoro-3-{[4-(2-methoxy-ethylamino)-3-trifluoromethyl-phenylamino]-methylene}-1,3-dihydro-indol-2-one
5-Fluoro-3-{[4-(tetrahydro-pyran-4-ylamino)-3-trifluoromethyl-phenylamino]-methylene}-1,3-dihydro-indol-2-one
3-{[4-(2-Dimethylamino-1-methyl-ethylamino)-3-trifluoromethyl-phenylamino]-methylene}-5-fluoro-1,3-dihydro-indol-2-one
5-Fluoro-3-{[4-(1-methoxymethyl-propylamino)-3-trifluoromethyl-phenylamino]-methylene}-1,3-dihydro-indol-2-one
3-{[4-(2-Diethylamino-ethylamino)-3-trifluoromethyl-phenylamino]-methylene}-5-fluoro-1,3-dihydro-indol-2-one
5-Fluoro-3-{[4-(3-morpholin-4-yl-propylamino)-3-trifluoromethyl-phenylamino]-methylene}-1,3-dihydro-indol-2-one
5-Fluoro-3-{[4-(2-piperidin-1-yl-ethylamino)-3-trifluoromethyl-phenylamino]-methylene}-1,3-dihydro-indol-2-one
3-{[4-(3-Diethylamino-propylamino)-3-trifluoromethyl-phenylamino]-methylene}-5-fluoro-1,3-dihydro-indol-2-one
3-{[4-(1-Benzyl-pyrrolidin-3-ylamino)-3-trifluoromethyl-phenylamino]-methylene}-5-fluoro-1,3-dihydro-indol-2-one
5-Fluoro-3-({4-[(5-methyl-pyrazin-2-ylmethyl)-amino]-3-trifluoromethyl-phenylamino}-methylene)-1,3-dihydro-indol-2-one
5-Fluoro-3-({4-[(tetrahydro-pyran-4-ylmethyl)-amino]-3-trifluoromethyl-phenylamino}-methylene)-1,3-dihydro-indol-2-one
3-{[4-(2-Diethylamino-1-methyl-ethylamino)-3-trifluoromethyl-phenylamino]-methylene}-5-fluoro-1,3-dihydro-indol-2-one
6-Fluoro-3-[(4-morpholin-4-yl-3-trifluoromethyl-phenylamino)-methylene]-1,3-dihydro-indol-2-one
3-[(4-Azepan-1-yl-3-trifluoromethyl-phenylamino)-methylene]-6-fluoro-1,3-dihydro-indol-2-one
6-Fluoro-3-{[4-(4-methyl-piperazin-1-yl)-3-trifluoromethyl-phenylamino]-methylene}-1,3-dihydro-indol-2-one
3-{[4-(2,6-Dimethyl-morpholin-4-yl)-3-trifluoromethyl-phenylamino]-methylene}-6-fluoro-1,3-dihydro-indol-2-one
3-{[4-(2,6-Dimethyl-morpholin-4-yl)-3-trifluoromethyl-phenylamino]-methylene}-6-fluoro-1,3-dihydro-indol-2-one
3-{[4-(1,3-Dihydro-isoindol-2-yl)-3-trifluoromethyl-phenylamino]-methylene}-6-fluoro-1,3-dihydro-indol-2-one
3-{[4-(4-Acetyl-piperazin-1-yl)-3-trifluoromethyl-phenylamino]-methylene}-6-fluoro-1,3-dihydro-indol-2-one
N-(1-{4-[(6-Fluoro-2-oxo-1,2-dihydro-indol-3-ylidenemethyl)-amino]-2-trifluoromethyl-phenyl}-pyrrolidin-3-yl)-acetamide
6-Fluoro-3-{[4-(3-methanesulfonyl-pyrrolidin-1-yl)-3-trifluoromethyl-phenylamino]-methylene}-1,3-dihydro-indol-2-one
6-Fluoro-3-{[4-(2-methoxy-ethylamino)-3-trifluoromethyl-phenylamino]-methylene}-1,3-dihydro-indol-2-one
6-Fluoro-3-{[4-(tetrahydro-pyran-4-ylamino)-3-trifluoromethyl-phenylamino]-methylene}-1,3-dihydro-indol-2-one
3-{[4-(2-Dimethylamino-1-methyl-ethylamino)-3-trifluoromethyl-phenylamino]-methylene}-6-fluoro-1,3-dihydro-indol-2-one
6-Fluoro-3-{[4-(1-methoxymethyl-propylamino)-3-trifluoromethyl-phenylamino]-methylene}-1,3-dihydro-indol-2-one
3-{[4-(2-Diethylamino-ethylamino)-3-trifluoromethyl-phenylamino]-methylene}-6-fluoro-1,3-dihydro-indol-2-one
6-Fluoro-3-{[4-(2-pyridin-2-yl-ethylamino)-3-trifluoromethyl-phenylamino]-methylene}-1,3-dihydro-indol-2-one
6-Fluoro-3-{[4-(2-pyridin-3-yl-ethylamino)-3-trifluoromethyl-phenylamino]-methylene}-1,3-dihydro-indol-2-one
6-Fluoro-3-({4-[(pyridin-2-ylmethyl)-amino]-3-trifluoromethyl-phenylamino}-methylene)-1,3-dihydro-indol-2-one
6-Fluoro-3-{[4-(2-piperidin-1-yl-ethylamino)-3-trifluoromethyl-phenylamino]-methylene}-1,3-dihydro-indol-2-one
6-Fluoro-3-({4-[3-(2-methyl-piperidin-1-yl)-propylamino]-3-trifluoromethyl-phenylamino}-methylene)-1,3-dihydro-indol-2-one
6-Fluoro-3-{[4-(2-methoxy-1-methyl-ethylamino)-3-trifluoromethyl-phenylamino]-methylene}-1,3-dihydro-indol-2-one
3-{[4-(2-Dimethylamino-ethylamino)-3-trifluoromethyl-phenylamino]-methylene}-6-fluoro-1,3-dihydro-indol-2-one
3-{[4-(3-Diethylamino-propylamino)-3-trifluoromethyl-phenylamino]-methylene}-6-fluoro-1,3-dihydro-indol-2-one
6-Fluoro-3-{[4-(3-imidazol-1-yl-propylamino)-3-trifluoromethyl-phenylamino]-methylene}-1,3-dihydro-indol-2-one
3-{[4-(2-Diisopropylamino-ethylamino)-3-trifluoromethyl-phenylamino]-methylene}-6-fluoro-1,3-dihydro-indol-2-one
6-Fluoro-3-({4-[(tetrahydro-pyran-4-ylmethyl)-amino]-3-trifluoromethyl-phenylamino}-methylene)-1,3-dihydro-indol-2-one
3-{[4-(2-Diethyl amino)-3-trifluoromethyl-phenylamino]-methylene-6-fluoro-1,3-dihydro-indol-2-one
6-Fluoro-3-({4-[2-(3-fluoro-pyrrolidin-1-yl)-ethoxy]-phenylamino}-methylene)-1,3-dihydro-indol-2-one 5-Fluoro-3-({4-[2-(3-fluoro-pyrrolidin-1-yl)-ethoxy]-phenylamino}-methylene)-1,3-dihydro-indol-2-one
3-({4-[2-(3-Fluoro-pyrrolidin-1-yl)-ethoxy]-phenylamino}-methylene)-1,3-dihydro-indol-2-one
5-Chloro-3-({4-[2-(3-fluoro-pyrrolidin-1-yl)-ethoxy]-phenylamino}-methylene)-1,3-dihydro-indol-2-one
3-({4-[2-(3-Fluoro-pyrrolidin-1-yl)-ethoxy]-phenylamino}-methylene)-4-methyl-1,3-dihydro-indol-2-one
4-Fluoro-3-({4-[2-(3-fluoro-pyrrolidin-1-yl)-ethoxy]-phenylamino}-methylene)-1,3-dihydro-indol-2-one
3-({4-[2-(3-Fluoro-pyrrolidin-1-yl)-ethoxy]-phenylamino}-methylene)-1-piperidin-4-yl-1,3-dihydro-indol-2-one
6-Fluoro-3-({4-[3-(3-fluoro-pyrrolidin-1-yl)-propoxy]-phenylamino}-methylene)-1,3-dihydro-indol-2-one
5-Fluoro-3-({4-[3-(3-fluoro-pyrrolidin-1-yl)-propoxy]-phenylamino}-methylene)-1,3-dihydro-indol-2-one
5-Chloro-3-({4-[3-(3-fluoro-pyrrolidin-1-yl)-propoxy]-phenylamino}-methylene)-1,3-dihydro-indol-2-one
3-({4-[3-(3-Fluoro-pyrrolidin-1-yl)-propoxy]-phenylamino}-methylene)-4-methyl-1,3-dihydro-indol-2one
4-Fluoro-3-(4-[3-(3-fluoro-pyrrolidin-1-yl)-propoxy]-phenylamino}-methylene)-1,3-dihydro-indol-2-one
3-({4-[3-(3-Fluoro-pyrrolidin-1-yl)-propoxy]-phenylamino}-methylene)-1-piperidin-4-yl-1,3-dihydroindol-2-one The present invention is not to be limited in scope by the exemplified embodiments which are intended as illustrations of single aspects of the invention only. Indeed, various modifications of the invention in addition to those described herein will become apparent to those skilled in the art from the foregoing description. For example novel compounds of formula II, below may be utilized in the method of treating diseases described above.

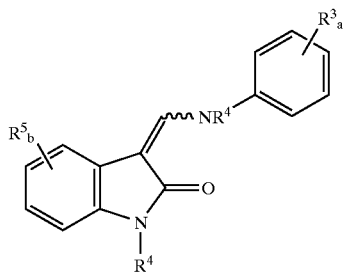

wherein $R^5$ is selected from the group consisting of halogen, nitro, hydroxy, hydrocarbyl, substituted hydrocarbyl, amide, thioamide, amine, thioether and sulfonyl; $R^3$ is selected from the group consisting of D, halogen, nitro, hydroxy, hydrocarbyl, substituted hydrocarbyl, amide, thioamide, amine, thioether and sulfonyl and phosphonic acid; $R^4$ is selected from the group consisting of hydrogen, hydrocarbyl and substituted hydrocarbyl; b is 0 or an integer from 1 to 3; a is 0 or an integer of from 1 to 5; the wavy line represents a E or Z bond and pharmaceutically acceptable salts thereof. Said hydrocarbyl and/or substituted hydrocarbyl may be alkyl, alkenyl, alkynyl, aryl (including carbocylic aryl and heterocyclic aryl) and alkaryl.

Such modifications are intended to fall within the scope of the appended claims.

All references cited herein are hereby incorporated by reference in their entirety.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

The invention claimed is:
1. A compound represented by the general formula I

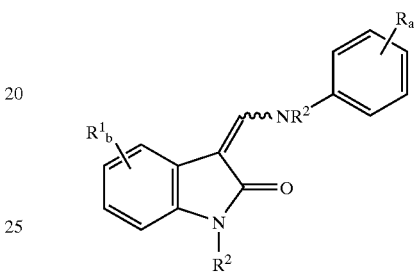

wherein $R^1$ is selected from the group consisting of fluoro, chloro, CN, $C_1$ to $C_4$alkyl and aryl; $R^2$ is selected from the group consisting of hydrogen, $C_1$ to $C_8$ alkyl, $COCH_3$, $CH_2CH_2OH$ and $CH_2CH_2CH_2OH$; R is selected from the group consisting of D, halogen, $C_1$ to $C_8$ alkyl, $CF_3$, $OCF_3$, $OCF_2H$, $CH_2CN$, CN, $SR^2$, $(CR_7R_8)_cC(O)OR^2$, $C(O)N(R^2)_2$, $(CR_7R_8)_cOR^2$, $HNC(O)R^2$, HN—C(O)$OR^2$, $(CR_7R_8)_cN(R^2)_2$, $SO_2$ $(CR_7R_8)_cN(R^2)_2$, $OP(O)(OR^2)_2$, $OC(O)OR^2$, $OCH_2O$, HN—CH=CH, —N(COR$^2$)CH$_2$CH$_2$, HC=N—NH, N=CH—S, $(CR_7R_8)_c$—$R^6$ and $NR_2(CR^7R^8)_dR^6$ wherein $R^6$ is selected from the group consisting of halogen, dilower alkylamino, piperidinyl, 3-fluoropyrrolidinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-petrahydro-(1H)-1,4-diazepinyl-5(4H)-one, N-methylhomopiperazinyl, (dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl N-acetylhomopiperazinyl, 3-(diethylamino)pyrrolidinyl, 1,4-dioxa-8-azaspiro[4.5]decanyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histaminyl, N,N-diisopropylethylenediaminyl, 1-benzyl-3-aminopyrrolidyl 2-(aminomethyl)-5-methylpyrazinyl, 2,2- dimethyl-1,3-dioxolane-4-methanaminyl, (R)-3-amino-1-N-BOC-pyrrolidinyl, 4-Amino-1,2,2,6,6-pentamethylpiperidinyl, 4-aminomethyltetrahydropyran, ethanolamine and lower alkyl-substituted derivatives thereof and wherein when c is 1 said CH$_2$ may be

and CH$_2$CH$_2$CH$_2$; provided said alkyl or phenyl radicals may be substituted with one or two halo, hydroxy or lower alkyl amino radicals and wherein R$^7$ and R$^8$ are selected from the group consisting of H, F and C$_1$–C$_4$ alkyl or CR$^7$R$^8$ may represent a carbocyclic ring of from 3 to 6 carbons;
  b is 0 or an integer of from 1 to 3;
  a is 0 or an integer of from 1 to 5;
  c is 0 or an integer of from 1 to 4;
  d is an integer of from 1 to 5;
  the wavy line represents a E or Z bond and pharmaceutically acceptable salts thereof; provided however said compound is not
3-Phenylaminomethylene-1,3-dihydro-indol-2-one
3-[(3-Bromo-phenylamino)-methylene]-1,3-dihydro-indol-2-one,
3-[(4-Bromo-phenylamino)-methyl]-1,3-dihydro-indol-2-one,
3-[(3-Bromo-phenylamino)-methyl]-1,3-dihydro-indol-2-one,
3-[(4-Ethyl-phenylamino)-methylene]-1,3-dihydro-indol-2-one,
3-Ethyl-phenylamino)-methylene]-1,3-dihydro-indol-2-one,
3-[(4-Methoxy-phenylamino)-methylene]-1,3-dihydro-indol-2-one,
4-[(2-Oxo-1,3-dihydro-indol-3-ylidenemethyl)-amino]-benzoic acid ethyl ester,
3-[(2-Ethyl-phenylamino)-methylene}-1,3-dihydro-indol-2-one,
3-[(3-Fluoro-4-methyl-phenylamino)-methylene]-1,3-dihydro-indol-2-one,
3-[(3-Fluoro-2-methyl-phenylamino)-methylene]-1,3-dihydro-indol-2-one,
3-[(4-Hydroxy-phenylamino)-methylene]-1,3-dihydro-indol-2-one,
3-[(3-Chloro-4-hydroxy-phenylamino)-methylene]-1,3-dihydro-indol-2-one or
3-[(4-Fluoro-2-methyl-phenylamino)-methylene]-1,3-dihydro-indol-2-one.

2. The compound of claim 1 wherein R$^1$ is selected from the group consisting of CH$_3$, F and Cl.

3. The compound of claim 1 wherein a is 0.

4. The compound of claim 1 wherein R$^2$ is H.

5. The compound of claim 1 wherein R is selected from the group consisting of CH$_3$, CH$_2$CH$_3$, OCH$_3$, OH, t-butyl, F, CN, C(O)NH$_2$, N C(O)CH$_3$, CH$_2$C(O)OH, SO$_2$NH$_2$, C(O)OH, OCF$_2$H, isopropyl, C$_2$H$_5$OH, C(O)OCH$_3$, CH$_2$OH, NH—CH=CH, HC=N—N—H, N=CH—S, morpholinyl and CH$_2$N(CH$_3$)$_2$.

6. The compound of claim 3 wherein b is 0 and R$^2$ is H.

7. The compound of claim 4 wherein a is 1, R$^2$ is H and R is m-ethyl.

8. The compound of claim 4 wherein a is 1, and R is p-methoxy.

9. The compound of claim 4 wherein a is 1, and R is p-hydroxy.

10. The compound of claim 4 wherein a is 1, b is 0 and R is m-hydroxy.

11. The compound of claim 4 wherein a is 1, b is 0 and R is p-cyano.

12. The compound of claim 4 wherein a is 1, b is 0 and R is m-C(O)NH$_2$.

13. The compound of claim 4 wherein a is 1, b is 0 and R is p-NC(O)CH$_3$.

14. The compound of claim 4 wherein a is 1, b is 0 and R is p-CH$_2$C(O)OH.

15. The compound of claim 4 wherein a is 1, b is 0 and R is p-SO$_2$NH$_2$.

16. The compound of claim 4 wherein a is 1, b is 0 and R is p-CH$_2$OH.

17. The compound of claim 4 wherein a is 1, b is 0 and R is m-methoxy.

18. The compound of claim 4 wherein R is p-CH$_2$CH$_2$OH.

19. The compound of claim 4 wherein a is 1, b is 0 and R is HN—CH=CH.

20. The compound of claim 4 wherein a is 1, b is 0 and R is HC=N—NH.

21. The compound of claim 4 wherein a is 1, b is 0 and R is p-N-morpholinyl.

22. The compound of claim 4 wherein a is 1, b is 0 and R is N—CH—S.

23. The compound of claim 4 wherein a is 1, b is 0 and R is p-OCHF$_2$.

24. The compound of claim 4 wherein a is 2 and R is m-hydroxy and p-COOH.

25. The compound of claim 4 wherein a is 2 and R is m-hydroxy and p-CH$_3$.

26. The compound of claim 4 wherein a is 2 and R is m-hydroxy and p-OCH$_3$.

27. The compound of claim 4 wherein a is 2 and R is m-F and p-OCH$_3$.

28. The compound of claim 4 wherein b is 1 and R$^1$ is CH$_3$, a is 1 and R is m-hydroxy.

29. The compound of claim 4 wherein b is 1, R is CH$_3$, a is 1 and R is NH—N=CH.

30. The compound of claim 4 wherein b is 1, R is CH$_3$, a is 2 and R is N—CH=CH.

31. The compound of claim 4 wherein b is 1, R is CH$_3$, a is 1 and R is S—CH=N.

32. The compound of claim 4 wherein b is 1, R$^1$ is CH$_3$, a is 1 and R is p-hydroxy.

33. The compound of claim 4 wherein b is 1, R$^1$ is CH$_3$, a is 1 and R is p-CH$_2$OH.

34. The compound of claim 4 wherein b is 1, R$^1$ is CH$_3$, a is 2 and R is m-F and p-OCH$_3$.

35. The compound of claim 4 wherein b is 1, R$^1$ is Cl, a is 2 and R is m-hydroxy and p-OCH$_3$.

36. The compound of claim 4 wherein b is 1, R$^1$ is Cl, a is 2 and R is m, p-di-OCH$_3$.

37. The compound of claim 4 wherein b is 1, R$^1$ is Cl, a is 1 and R is HN—N=CH.

38. The compound of claim 4 wherein b is 1, R$^1$ is Cl, a is 1 and R is p-N-morpholinyl.

39. The compound of claim 4 wherein b is 1, R$^1$ is Cl, a is 2 and R is m-CH$_2$N(C$_2$H$_5$)$_2$ and p-hydroxy.

40. The compound of claim 4 wherein b is 1, R$^1$ is Cl, a is 1 and R is p-CH$_2$OH.

41. A pharmaceutical composition comprising a pharmaceutically acceptable carrier or excipient and a compound according to claim 1.

42. The compound of claim 1 wherein R is selected from the group consisting of fluoro, methyl, $NR_2(CR^7R^8)_dR^6$ and $(CR^7R^8)_c$—$R^6$, wherein $R^6$ is selected from the group consisting of diloweralkylamino, piperidinyl, 3-fluoropyrrolidinyl, 3-fluoropiperidinyl, 2-pyridinyl, 3-pyridinyl, 4-pyridinyl, piperdinyl 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (dimethylamino)pyrrolidinyl, N-(2-methoxyethyl)-N-propylaminyl, Isoindolinyl, Nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N-BOC-pyrrolidinyl, 4-amino-1,2,2,6,6-pentamethylpiperidinyl, 4-aminomethyltetrahydropyranyl, ethanolamine and alkyl-substituted derivatives thereof.

43. The compound of claim 42 wherein $R^6$ is selected from the group consisting of dimethylamino, diethylamino, 3-fluoropyrrolidinyl, 3-fluoropiperidinyl, 3-pyridinyl, 4-pyridinyl, pyrrolidinyl, morpholinyl, piperazinyl, heptamethyleneiminyl, tetrahydrofurfurylaminyl, 4-aminotetrahydropyranyl, N,N-diisopropylethylenediaminyl and 4-aminomethyltetrahydropyranyl.

44. The compound of claim 43 wherein $R^6$ is unsubstituted or mono or di-methyl substituted morpholinyl, pyrrolidinyl, piperazinyl or piperidinyl.

45. The compound of claim 44 wherein $R^6$ is morpholinyl.

* * * * *